US010213492B2

(12) United States Patent
Bax et al.

(10) Patent No.: US 10,213,492 B2
(45) Date of Patent: Feb. 26, 2019

(54) TREATMENT FOR MITOCHONDRIAL NEUROGASTROINTESTINAL ENCEPHALOMYOPATHY (MNGIE)

(75) Inventors: Bridget Bax, Greater London (GB); Murray Bain, Greater London (GB)

(73) Assignee: St. George's Hospital Medical School, Greater London (GB)

(*) Notice: Subject to any disclaimer, the term of this patent is extended or adjusted under 35 U.S.C. 154(b) by 90 days.

(21) Appl. No.: 14/347,635

(22) PCT Filed: Sep. 3, 2012

(86) PCT No.: PCT/GB2012/052157
§ 371 (c)(1),
(2), (4) Date: Mar. 26, 2014

(87) PCT Pub. No.: WO2013/045885
PCT Pub. Date: Apr. 4, 2013

(65) Prior Publication Data
US 2014/0219980 A1    Aug. 7, 2014

(30) Foreign Application Priority Data
Sep. 28, 2011 (GB) .................................. 1116767.3

(51) Int. Cl.
A61K 38/45    (2006.01)
A61K 38/47    (2006.01)
A61K 38/43    (2006.01)
A61K 35/18    (2015.01)

(52) U.S. Cl.
CPC .............. *A61K 38/45* (2013.01); *A61K 35/18* (2013.01); *A61K 38/47* (2013.01)

(58) Field of Classification Search
None
See application file for complete search history.

(56) References Cited

U.S. PATENT DOCUMENTS

| | | | |
|---|---|---|---|
| 5,830,735 A * | 11/1998 | Andreoli | C12N 9/20 435/198 |
| 5,834,210 A | 11/1998 | Liu | |
| 6,054,305 A | 4/2000 | Tatsumi | |
| 2006/0121031 A1 | 6/2006 | McKenzie | |

FOREIGN PATENT DOCUMENTS

| | | |
|---|---|---|
| EP | 1457568 | 9/2004 |
| GB | 2317892 | 4/1998 |
| WO | 93/08273 | 4/1993 |
| WO | 01/70955 | 9/2001 |

OTHER PUBLICATIONS

Krenitsky, T.A. et al. 1981. Purine nucleoside synthesis, an efficient method employing nucleoside phosphorylases. Biochemistry 20: 3615-3621. specif. pp. 3615, 3617.*
Restani, P. et al. 2004. Characterization of bovine serium albumin epitopes and their role in allergic reactions. Allergy 59 (Suppl. 78: 21-24. specif. 21.*
Liu, S. et al. 1997. Removal of endotoxin from recombinant protein preparations. Clinical Biochemistry 30(6): 455-463. specif. pp. 455, 458, 460.*
Lara, M.C. et al. 2007. Mitochondrial neurogastrointestinal encephalomyopathy (MNGIE): Biochemical features and therapeutic approaches. Bioscience Reports 27: 151-163. specif. pp. 151, 159, 160.*
Millan, C.G. et al. 2004. Drug, enzyme and peptide delivery using erythrocyte as carriers. Journal of Controlled Release 95: 27-49. specif. pp. 37, 41.*
Richards, S. et al. 2008. Development of defined media for the serum-free expansion of primary keratinocytes and human embryonic cells. Tissue Engineering: Part C 14(3): 221-232. specif. pp. 221.*
Aksoy et al., (2005) A previously diagnosed mitochondrial neurogastrointestinal encephalomyopathy patient presenting with perforated ileal diverticulitis. Turk J Gastroenterol 16(4): 228-31.
Altschul (1993) A protein alignment scoring system sensitive at all evolutionary distances. J Mol Evol 36(3): 290-300.
Altschul et al., (1990) Basic local alignment search tool. J Mol Biol 215(3): 403-10.
Angervall and Carlström (1963) Theoretical criteria for the use of relative organ weights and similar ratios in biology. J Theor Biol 4(3): 254-9.
Bariş et al., (2010) Mitochondrial neurogastrointestinal encephalomyopathy (MNGIE): case report with a new mutation. Eur J Pediatr 169(11): 1375-8.
Bartlett (1937) Properties of sufficiency and statistical tests. Proceedings of the Royal Society of London. Series A, Mathematical and Physical Sciences 160(901): 268-282.
Barton et al., (1992) Human platelet-derived endothelial cell growth factor is homologous to *Escherichia coli* thymidine phosphorylase. Protein Sci 1(5): 688-90.
Bax et al., (1999) Survival of human carrier erythrocytes in vivo. Clin Sci (Lond) 96(2): 171-8.
Bax et al., (2000) In vitro and in vivo studies with human carrier erythrocytes loaded with polyethylene glycol-conjugated and native adenosine deaminase. Br J Haematol 109(3): 549-54.
Bax et al., (2007) A 9-yr evaluation of carrier erythrocyte encapsulated adenosine deaminase (ADA) therapy in a patient with adult-type ADA deficiency. Eur J Haematol 79(4) 338-48.

(Continued)

*Primary Examiner* — Renee Claytor
*Assistant Examiner* — Sharon M. Papciak
(74) *Attorney, Agent, or Firm* — Rodney J. Fuller; Booth Udall Fuller, PLC

(57) ABSTRACT

The invention provides a method of treating mitochondrial neurogastrointestinal encephalomyopathy (MNGIE) in a patient, comprising administering to the patient autologous erythrocytes that contain thymidine phosphorylase and are free of animal proteins other than proteins derived from the patient. The erythrocytes generally contain a low amount of endotoxin.

16 Claims, 12 Drawing Sheets

Specification includes a Sequence Listing.

(56) References Cited

OTHER PUBLICATIONS

Brito and Singh (2011) Acceptable levels of endotoxin in vaccine formulations during preclinical research. J Pharm Sci 100(1): 34-7.
Cardaioli et al., (2010) A second MNGIE patient without typical mitochondrial skeletal muscle involvement. Neurol Sci 31(4): 491-4.
Celebi et al., (2006) Abdominal pain related to mitochondrial neurogastrointestinal encephalomyopathy syndrome may benefit from splanchnic nerve blockade. Paediatr Anaesth 16(10): 1073-6.
Chalmers (1985) Comparison and potential of hypo-osmotic and iso-osmotic erythrocyte ghosts and carrier erythrocytes as drug and enzyme carriers. Bibl Haematol 51: 15-24.
Chinnery and Turnbull (2001) Epidemiology and treatment of mitochondrial disorders. Am J Med Genet 106(1): 94-101.
Devereux et al., (1984) A comprehensive set of sequence analysis programs for the VAX. Nucleic Acids Res 12(1 Pt 1): 387-95.
Eccleston et al., (1995) Neurons of the peripheral nervous system express thymidine phosphorylase. Neurosci Lett 192(2): 137-41.
Fisher RA (1973) Statistical Methods for Research Workers, 14th EDN., p. 96. Hafner Publishing Company, New York, USA.
Giordano et al., (2008) Gastrointestinal dysmotility in mitochondrial neurogastrointestinal encephalomyopathy is caused by mitochondrial DNA depletion. Am J Pathol 173(4): 1120-8.
Halter et al., (2011) Allogeneic hematopoietic SCT as treatment option for patients with mitochondrial neurogastrointestinal encephalomyopathy (MNGIE): a consensus conference proposal for a standardized approach. Bone Marrow Transplant 46(3): 330-7.
Harris et al., (1957) The relationship of abnormal red cells to the normal spleen. Clin Sci (Lond) 16(2): 223-30.
Hirano et al., (1994) Mitochondrial neurogastrointestinal encephalomyopathy (MNGIE): clinical, biochemical, and genetic features of an autosomal recessive mitochondrial disorder. Neurology 44(4): 721-7.
Hirano et al., (2004) Mitochondrial neurogastrointestinal encephalomyopathy (MNGIE): a disease of two genomes. Neurologist 10(1): 8-17.
Hirano et al., (2006) Allogeneic stem cell transplantation corrects biochemical derangements in MNGIE. Neurology 67(8): 1458-60.
Hirano et al., (2008) Sustained biochemical and clinical improvements two years post-allogeneic stem cell transplantation in patient with MNGIE. American Academy of Neurology Annual Meeting Abstract S48.002.
Ihler et al., (1973) Enzyme loading of erythrocytes. Proc Natl Acad Sci U S A 70(9): 2663-6.
la Marca et al., (2006) Pre- and post-dialysis quantitative dosage of thymidine in urine and plasma of a MNGIE patient by using HPLC-ESI-MS/MS. J Mass Spectrom 41(5): 586-92.
Lara et al., (2006) Infusion of platelets transiently reduces nucleoside overload in MNGIE. Neurology 67(8): 1461-3.
Martí et al., (2003) Elevated plasma deoxyuridine in patients with thymidine phosphorylase deficiency. Biochem Biophys Res Commun 303(1): 14-8.
Martí et al., (2004) Definitive diagnosis of mitochondrial neurogastrointestinal encephalomyopathy by biochemical assays. Clin Chem 50(1): 120-4.
Matsukawa et al., (1996) Tissue distribution of human gliostatin/platelet-derived endothelial cell growth factor (PD-ECGF) and its drug-induced expression. Biochim Biophys Acta 1314(1-2): 71-82.
Miller et al., (2001) Workshop on bioanalytical methods validation for macromolecules: summary report. Pharm Res 18(9): 1373-83.
Mire-Sluis et al., (2004) Recommendations for the design and optimization of immunoassays used in the detection of host antibodies against biotechnology products. J Immunol Methods 289(1-2): 1-16.
Moran et al., (2008) Carrier erythrocyte entrapped thymidine phosphorylase therapy for MNGIE. Neurology 71(9): 686-8.
Murray et al., (2006) The mouse immune response to carrier erythrocyte entrapped antigens. Vaccine 24(35-36): 6129-39.
Nishigaki et al., (2003) Site-specific somatic mitochondrial DNA point mutations in patients with thymidine phosphorylase deficiency. J Clin Invest 111(12): 1913-21.
Nishigaki et al., (2004) ND5 is a hot-spot for multiple atypical mitochondrial DNA deletions in mitochondrial neurogastrointestinal encephalomyopathy. Hum Mol Genet 13(1): 91-101.
Nishino et al., (1999) Thymidine phosphorylase gene mutations in MNGIE, a human mitochondrial disorder. Science 283(5402): 689-92.
Nishino et al., (2000) Mitochondrial neurogastrointestinal encephalomyopathy: an autosomal recessive disorder due to thymidine phosphorylase mutations. Ann Neurol 47(6): 792-800.
Nishino et al., (2001) MNGIE: from nuclear DNA to mitochondrial DNA. Neuromuscul Disord 11(1): 7-10.
Papadimitriou et al., (1998) Partial depletion and multiple deletions of muscle mtDNA in familial MNGIE syndrome. Neurology 51(4): 1086-92.
Pearse (2006) Histopathology of the thymus. Toxicol Pathol 34(5): 515-47.
Said et al., (2005) Clinicopathological aspects of the neuropathy of neurogastrointestinal encephalomyopathy (MNGIE) in four patients including two with a Charcot-Marie-Tooth presentation. J Neurol 252(6): 655-62.
Schellekens (2002) Immunogenicity of therapeutic proteins: clinical implications and future prospects. Clin Ther 24(11): 1720-40; discussion 1719.
Shankar et al., (2008) Recommendations for the validation of immunoassays used for detection of host antibodies against biotechnology products. J Pharm Biomed Anal 48(5): 1267-81.
Shapiro and Wilk (1965) An analysis of variance test for normality (complete samples). Biometrika 52 (3-4): 591-611.
Shoffner (2010) Mitochondrial Neurogastrointestinal Encephalopathy Disease. In: Pagon RA, Bird TC, Dolan CR, Stephens K, editors. GeneReviews. Seattle (WA): University of Washington, Seattle; 1993-2005 (updated 2010).
Spinazzola et al., (2002) Altered thymidine metabolism due to defects of thymidine phosphorylase. J Biol Chem 277(6): 4128-33.
Sprandel (1981) Morphology of haemoglobin-containing human erythrocyte 'ghosts'. Micron (1969) 12(1): 29-36.
Sprandel et al., (1979) In vitro studies on resealed erythrocyte ghosts as protein carriers. Res Exp Med (Berl 175(3): 239-45.
Usuki et al., (1990) Localization of platelet-derived endothelial cell growth factor in human placenta and purification of an alternatively processed form. Cell Regul 1(8): 577-96.
Valentino et al., (2007) Thymidine and deoxyuridine accumulate in tissues of patients with mitochondrial neurogastrointestinal encephalomyopathy (MNGIE). FEBS Lett 581(18): 3410-4.
Wilcoxon (1945) Individual comparisons by ranking methods. Biometrics Bulletin 1(6): 80-83.
Yavuz et al., (2007) Treatment of mitochondrial neurogastrointestinal encephalomyopathy with dialysis. Arch Neurol 64(3): 435-8.
EC Commission Directive 2004/10/EC of Feb. 11, 2004 (Official Journal No. L 50/44).
EMEA, 2006. Committee for Medicinal Products for Human Use (CHMP). The Guideline on Immunogenicity Assessment of Biotechnology-Derived Therapeutic Proteins. (Effective Apr. 2008), EMEA/CHMP/BMWP/14327/2006. Available from: http://www.ema.europa.eu/docs/en_GB/document_library/Scientific_guideline/2009/09/WC500003946.pdf.
FDA, 2001. Centre for Drug Evaluation and Research. Centre for Veterinary Medicine. Guidance for Industry: Bioanalytical Methods Validation. Available from: http://www.fda.gov/downloads/drugs/guidancecomplianceregulatoryinformation/guidances/ucm070107.
FDA, 2009. Centre for Drug Evaluation and Research. Centre for Biologics Evaluation and Research. Draft Guidance for Industry: Assay Development for Immunogenicity Testing of Therapeutic Proteins. Available from: http://www.fda.gov/downloads/drugs/guidancecomplianceregulatoryinformation/guidances/ucm192750.
OECD Principles of Good Laboratory Practice ENV/MC/CHEM(98)17 (1998).

(56) References Cited

OTHER PUBLICATIONS

The UK Good Laboratory Practice Regulations (Statutory Instrument 1999 No. 3106, as amended by Statutory Instrument 2004 No. 994).

* cited by examiner

Product thymidine deoxyribose
1-phosphate thymine deoxyuridine deoxyribose
1-phosphate uracil

| Tris buffer | 0.1% Triton X-100 | Tris buffer | 45 mM NaCl | I, II, III 200 mM NaCl | 2 M NaCl |

A

B
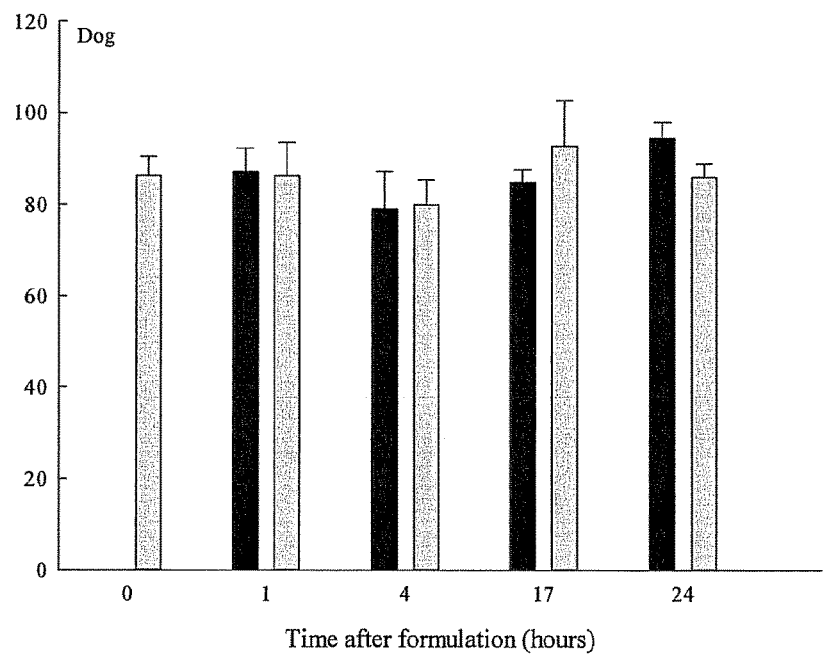
Fig. 17
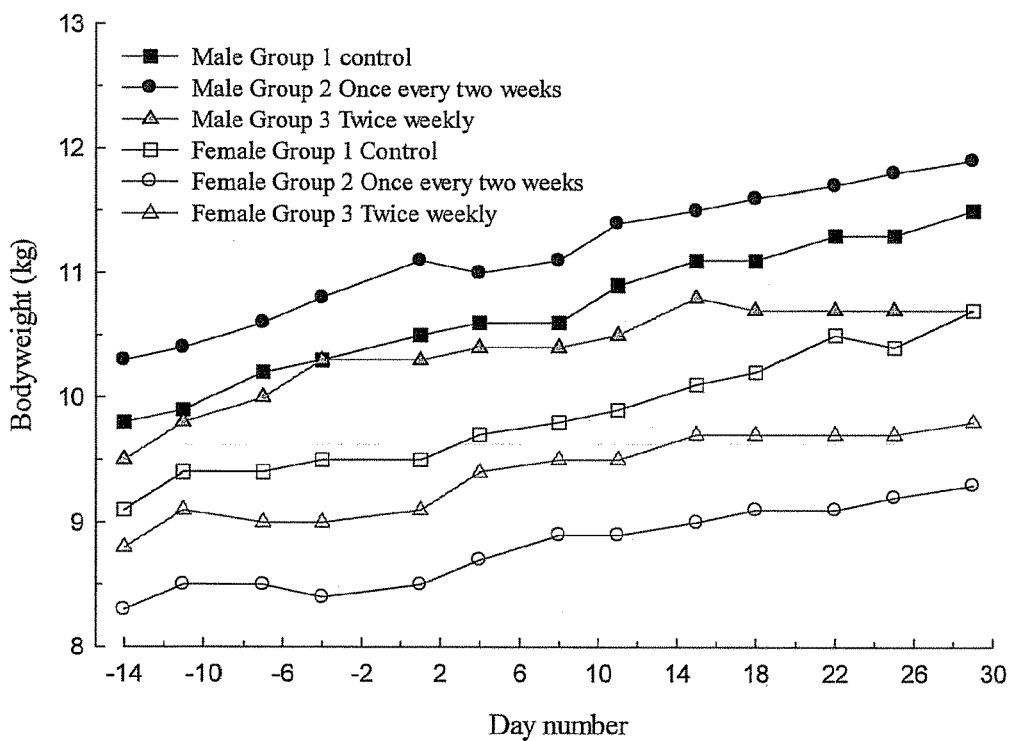

A

B

C

SEQUENCE LISTING

<160> NUMBER OF SEQ ID NOS: 1

<210> SEQ ID NO 1
<211> LENGTH: 440
<212> TYPE: PRT
<213> ORGANISM: Escherichia coli

<400> SEQUENCE: 1

```
Met Phe Leu Ala Gln Glu Ile Ile Arg Lys Lys Arg Asp Gly His Ala
1               5                   10                  15

Leu Ser Asp Glu Glu Ile Arg Phe Phe Ile Asn Gly Ile Arg Asp Asn
                20                  25                  30

Thr Ile Ser Glu Gly Gln Ile Ala Ala Leu Ala Met Thr Ile Phe Phe
            35                  40                  45

His Asp Met Thr Met Pro Glu Arg Val Ser Leu Thr Met Ala Met Arg
50                  55                  60

Asp Ser Gly Thr Val Leu Asp Trp Lys Ser Leu His Leu Asn Gly Pro
65                  70                  75                  80

Ile Val Asp Lys His Ser Thr Gly Gly Val Gly Asp Val Thr Ser Leu
                85                  90                  95

Met Leu Gly Pro Met Val Ala Ala Cys Gly Gly Tyr Ile Pro Met Ile
            100                 105                 110

Ser Gly Arg Gly Leu Gly His Thr Gly Gly Thr Leu Asp Lys Leu Glu
        115                 120                 125

Ser Ile Pro Gly Phe Asp Ile Phe Pro Asp Asp Asn Arg Phe Arg Glu
    130                 135                 140

Ile Ile Lys Asp Val Gly Val Ala Ile Ile Gly Gln Thr Ser Ser Leu
145                 150                 155                 160

Ala Pro Ala Asp Lys Arg Phe Tyr Ala Thr Arg Asp Ile Thr Ala Thr
                165                 170                 175

Val Asp Ser Ile Pro Leu Ile Thr Ala Ser Ile Leu Ala Lys Lys Leu
            180                 185                 190

Ala Glu Gly Leu Asp Ala Leu Val Met Asp Val Lys Val Gly Ser Gly
        195                 200                 205

Ala Phe Met Pro Thr Tyr Glu Leu Ser Glu Ala Leu Ala Glu Ala Ile
    210                 215                 220

Val Gly Val Ala Asn Gly Ala Gly Val Arg Thr Thr Ala Leu Leu Thr
225                 230                 235                 240

Asp Met Asn Gln Val Leu Ala Ser Ser Ala Gly Asn Ala Val Glu Val
                245                 250                 255

Arg Glu Ala Val Gln Phe Leu Thr Gly Glu Tyr Arg Asn Pro Arg Leu
            260                 265                 270

Phe Asp Val Thr Met Ala Leu Cys Val Glu Met Leu Ile Ser Gly Lys
        275                 280                 285
```

-continued

```
Leu Ala Lys Asp Asp Ala Glu Ala Arg Ala Lys Leu Gln Ala Val Leu
    290                 295                 300

Asp Asn Gly Lys Ala Ala Glu Val Phe Gly Arg Met Val Ala Ala Gln
305                 310                 315                 320

Lys Gly Pro Thr Asp Phe Val Glu Asn Tyr Ala Lys Tyr Leu Pro Thr
                325                 330                 335

Ala Met Leu Thr Lys Ala Val Tyr Ala Asp Thr Glu Gly Phe Val Ser
            340                 345                 350

Glu Met Asp Thr Arg Ala Leu Gly Met Ala Val Val Ala Met Gly Gly
                355                 360                 365

Gly Arg Arg Gln Ala Ser Asp Thr Ile Asp Tyr Ser Val Gly Phe Thr
    370                 375                 380

Asp Met Ala Arg Leu Gly Asp Gln Val Asp Gly Gln Arg Pro Leu Ala
385                 390                 395                 400

Val Ile His Ala Lys Asp Glu Asn Asn Trp Gln Glu Ala Ala Lys Ala
                405                 410                 415

Val Lys Ala Ala Ile Lys Leu Ala Asp Lys Ala Pro Glu Ser Thr Pro
            420                 425                 430

Thr Val Tyr Arg Arg Ile Ser Glu
            435                 440
```

TREATMENT FOR MITOCHONDRIAL NEUROGASTROINTESTINAL ENCEPHALOMYOPATHY (MNGIE)

RELATED APPLICATION DATA

This application is the U.S. National Stage of International Application No. PCT/GB2012/052157 filed Sep. 3, 2012, which claims priority to Great Britain Patent Application No. 1116767.3 filed Sep. 28, 2011. Each of the foregoing applications is hereby incorporated by reference in its entirety for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 4,114 byte ASCII (text) file named "Seq_List" created on Mar. 26, 2014.

FIELD OF THE INVENTION

The present invention relates to treating mitochondrial neurogastrointestinal encephalomyopathy (MNGIE).

BACKGROUND OF THE INVENTION

Mitochondrial Neurogastrointestinal Encephalomyopathy

Mitochondrial neurogastrointestinal encephalomyopathy (MNGIE, Mendelian Inheritance in Man #603041, Genome Database accession #9835128) is a fatal inherited metabolic disorder caused by mutations in a nuclear gene controlling the replication and expression of the mitochondrial genome (Nishino et al., 1999; Hirano et al., 2004). In the past the disorder has also been referred to as:
polyneuropathy, ophthalmoplegia, leukoencephalopathy, and intestinal pseudo-obstruction (POLIP);
myoneurogastrointestinal encephalopathy (MNGIE);
oculogastrointestinal muscular dystrophy (OGIMD);
mitochondrial neurogastrointestinal encephalopathy syndrome;
mitochondrial encepalomyopathy with sensorimotor polyneuropathy, ophthalmoplegia, and pseudo-obstruction (MEPOP);
oculogastrointestinal muscular dystrophy (OGIMD);
thymidine phosphorylase deficiency; and
mitochondrial neurogastrointestinal encephalopathy syndrome.

In 1994 the name mitochondrial neurogastrointestinal encephalomyopathy was proposed, with the aim of preserving the acronym MNGIE, but to emphasize the mitochondrial abnormalities which are central to the pathogenic mechanism of this disorder (Hirano et al., 1994).

MNGIE is an autosomal recessive disorder of nucleotide metabolism caused by mutations in the nuclear TYMP gene (previously known as ECGF1). This gene encodes thymidine phosphorylase (EC 2.4.2.4), the enzyme required for the normal metabolism of the pyrimidine deoxynucleosides thymidine and deoxyuridine (Hirano et al., 2004). Mutations in the TYMP gene result in a complete or partial absence of thymidine phosphorylase activity, leading to a dramatic accumulation of thymidine and deoxyuridine in tissues and body fluids (Nishino et al., 1999; 2000; Hirano et al., 1994; Spinazzola et al., 2002 Marti et al., 2003; Valentino et al., 2007). Elevated systemic concentrations of these deoxynucleosides is mirrored by elevated intracellular concentrations of their corresponding triphosphates. This perturbs the physiological equilibrium of the four deoxynucleoside triphosphates within the mitochondria, thereby interfering with the normal replication of mtDNA, leading to multiple deletions, somatic point mutations and depletion of mtDNA (Hirano et al., 1994; Marti et al., 2003; Nishigaki et al., 2003; 2004) and ultimately mitochondrial failure (Hirano et al., 1994; Spinazzola et al., 2002; Marti et al., 2003). mtDNA codes for polypeptides, transfer RNA (tRNA) and ribosomal RNA (rRNA) required for the synthesis of enzymes involved in oxidative phosphorylation. The consequent failure of cellular energy production is believed to directly cause the central clinical manifestation, the degeneration of the peripheral nervous system.

Patients with MNGIE usually present during the second decade of life, though patients have presented as early as five months and as late as the fifth decade; the average age is 18.5 years (Nishino et al., 2001). The relatively late-onset is thought to be due to the progressive accumulation of mtDNA defects, with disease becoming apparent once the number of affected mitochondria reaches a critical threshold level. The disease has a homogeneous clinical presentation with gastrointestinal symptoms including early satiety, nausea, chronic abdominal pain, diarrhoea and weight loss. These symptoms are secondary to alimentary dysmotility caused by degeneration of the alimentary peripheral nervous system. Patients generally have a thin body habitus with reduced muscle mass, and cachexia may develop. Episodes of frank intestinal pseudo-obstruction may occur. Some patients develop a hepatopathy with liver steatosis and cirrhosis. Progressive external ophthalmoplegia and peripheral sensorimotor polyneuropathy are invariable. The latter affects the lower limbs initially. On magnetic resonance imaging (MRI) there is, in most cases, diffuse increased T2 signal in the deep white matter of the cerebral hemispheres, but this is usually asymptomatic (Hirano et al., 1994).

Skeletal muscle biopsy may show ragged-red fibres (due to abnormal proliferation of mitochondria in response to defective oxidative phosphorylation), ultrastructurally abnormal mitochondria, and abnormalities of both mitochondrial DNA (mtDNA) and mitochondrial electron transport chain enzymes activities on enzyme analysis (Papadimitriou et al., 1998).

Biochemical studies may show lactic acidosis, indicative of an oxidative phosphorylation defect. Plasma thymidine and deoxyuridine levels are increased to >3 µmo/l and 5 µmol/l, respectively, compared to undetectable levels in healthy unaffected controls (Marti et al., 2003; 2004). Urine concentrations of thymidine and deoxyuridine are also increased (Spinazzola et al., 2002). Thymidine phosphorylase activity in leukocytes of patients with MNGIE is severely reduced, showing little (<10% of healthy unaffected controls) or no activity (Spinazzola et al., 2002; Marti et al., 2004).

The molecular basis of MNGIE has been determined by PCR amplification and DNA sequence analysis; 52 different mutations in the TYMP gene have been identified since its first description and no predominant one has been reported [The Human Gene Mutation Database (HGMD) at the Institute of Medical Genetics in Cardiff]. A majority of these mutations are missense or nonsense, the others being small deletions, small insertions, and splice-site mutations. Patients are either homozygous or compound heterozygous for the TYMP mutation. Heterozygous carriers of TYMP mutations have 26 to 35% of residual thymidine phosphorylase activity, are asymptomatic and have undetectable levels of plasma thymidine and deoxyuridine (Nishino et al., 1999; Spinazzola et al., 2002).

MNGIE is a relentlessly progressive, degenerative disease with a poor prognosis, and causes a great deal of suffering to affected individuals. Gastrointestinal dysmotility caused by degeneration of the alimentary peripheral nervous system occurs in nearly all patients. The resulting digestive problems include early satiety, problems with swallowing (dysphagia), nausea and vomiting after eating, episodic abdominal distention and pain, and diarrhea. These gastrointestinal problems lead to severe weight loss and a reduced muscle mass. Disability results from the peripheral neuropathy; patients experience weakness of the lower extremities, particularly in hands and feet, numbness and tingling sensations. Other symptoms include ptosis (droopy eyelids), ophthalmoplegia (weakness of muscles which control eye movement), and hearing loss.

At present, there is no recognized specific treatment to prevent or reverse the inexorable clinical deterioration, and clinical management of the symptoms is non-specific and supportive. Survival is generally related to the degree of gastrointestinal involvement, with patients often dying as a result of cachexia, peritonitis, esophageal bleeding, intestinal rupture, or aspiration pneumonia.

In order to assess the mortality of MNGIE, the English language literature on the condition published between October 2005 to October 2010 was searched [Pubmed using search terms: MNGIE; Mitochondrial neurogastrointestinal encephalomyopathy; Chronic intestinal pseudo-obstruction]. The age of death could be determined in nineteen cases, for which the mean was 30.2 years, range 18 to 39 years (Aksoy et al., 2005; Said et al., 2005; Hirano et al., 2006; la Marca et al., 2006; Moran et al., 2006; Valentino et al., 2007; Giordano et al., 2008; Baris et al., 2010; Cardaioli et al., 2010). This compares with Nishino et al (2000) who estimated the mean age of death as 37.6 years; with a range of 26 to 58 years.

Treatments for MNGIE

MNGIE is a rare inherited metabolic disease for which at present there are no EMEA- or FDA-approved therapies. There is a critical requirement to develop a treatment that may prove beneficial.

There are no proven specific treatments for MNGIE. Current treatment is, therefore, symptomatic. Abdominal pain and nausea/vomiting secondary to gastrointestinal dysmotility are almost invariable. These symptoms are treated symptomatically with analgesics, bowel motility-stimulant drugs, anti-emetics and antibiotics for intestinal bacterial overgrowth. In intractable pain, splanchnic nerve or coeliac plexus blockade with bupivicaine has been reported to be helpful (Celebi et al, 2006; Shoffner, 2010). Pain may also occur in the limbs due to peripheral polyneuropathy. Such neuropathic pain is generally treated with centrally acting agents such as amitriptyline or pregabalin. In individuals with MNGIE there is an increased incidence of perforation of the gut. This generally requires emergency abdominal surgery. Malnutrition is a major problem in most individuals with MNGIE. Various forms of parenteral nutrition, including total parenteral nutrition, are frequently required.

Portal hypertension may occur and be complicated by ascites and oesophageal varices. These conditions are treated in the same way as when they occur in other conditions. Drugs that interfere with mitochondrial function should be avoided in individuals with MNGIE. Hepatically metabolized drugs should be administered with care or may be contraindicated depending on liver function. Physiotherapy and occupational therapy input is usually required, particularly to address the neurological aspects of the condition. In children special schooling arrangements may be necessary (Shoffner, 2010). MNGIE is a hereditary condition and individuals with the condition should be offered genetic counseling.

Thymidine and deoxyuridine are freely diffusible across cell membranes and exist in a state of equilibrium between the cellular and plasma compartments, and thus therapeutic strategies which aim to reduce or eliminate the pathological concentrations of plasma thymidine and deoxyuridine may be beneficial to patients with MNGIE. Haemodialysis and continuous ambulatory peritoneal dialysis have been used in an attempt to remove the toxic metabolites (Spinazzola et al., 2002; la Marca et al., 2006; Yavuz et al., 2007); haemodialysis was able to lower plasma nucleoside levels, but there was a rapid re-accumulation to pre-dialysis levels between dialysis sessions (la Marca et al., 2006).

Although peritoneal dialysis was unable to demonstrate a decrease in plasma metabolites, an improvement of clinical symptoms was noted. Infusions of platelets, which contain thymidine phosphorylase, have been shown to reduce circulating levels of thymidine and deoxyuridine in two patients (Lara et al., 2006). However, long-term platelet therapy is not a feasible option due to the short lifespan of transfused platelets, and risks of developing immune reactions and transmission of viral infections.

More recently allogenic stem cell transplantation has demonstrated a partial restoration of white cell thymidine phosphorylase activity, and a reduction or disappearance of plasma thymidine concentrations in patients who successfully engrafted (Hirano et al., 2006). Evidence that clinical benefit can be achieved by correction of the biochemical abnormalities has been shown in a single patient; thirty months post engraftment, it was noted that previously absent tendon reflexes had returned, and an improvement in nerve conduction. Total parenteral nutrition was replaced by a normal diet of 3,000 calories daily and bowel movements had normalised (Hirano et al., 2008).

Allogenic haematopoietic stem cell transplantation (HSCT) offers the possibility of a permanent correction of thymidine phosphorylase deficiency. To date, nine patients world-wide have received 12 allogenic HSCT; a second HSCT being performed in three patients (Halter et al., 2010). The graft sources employed were peripheral blood stem cells, bone marrow and cord blood. Four patients died, two due to transplant related mortality, and two from their disease. The remaining five patients were alive 8-48 months post-transplant and all demonstrated reduction or disappearance of plasma thymidine and deoxyuridine. An improvement of gastrointestinal symptoms and slight improvement of neurological symptoms has been observed in two patients.

Allogenic HSCT is still highly experimental and carries a 44% mortality risk. HSCT can potentially cure, but is limited by the availability of a matched donor. Patients are in a poor clinical condition with a restricted capacity to tolerate transplant-related problems. The administration of HSCT to these patients presents pharmacological challenges in terms of administering drugs with possible mitochondrial toxicity, and the requirement for parental administration due to disturbed gastrointestinal function and impairment of absorption. A published consensus proposal for standardising an approach to allogenic HSCT in MNGIE recommends restricting the recruitment of patients with an optimal donor to those without irreversible end-stage disease (Halter et al., 2010). Thus, for many patients there is no treatment option and clinical management is based on symptom relief and palliation.

The last two decades has seen the introduction of enzyme replacement therapies for the successful treatment of inherited metabolic diseases, including adenosine deaminase deficiency, Gaucher disease and other lysosomal storage disorders. The administration of the missing enzyme, usually by injection, enables the elimination of the pathological substrates which accumulate in these metabolic disorders, translating into clinical benefit. Chemical modifications of the native enzyme are often employed in the manufacturing process to increase protein stability, decrease immunogenicity, and to enable targeting of enzyme to the appropriate cellular compartment. The development of recombinant DNA techniques and over-expressing cells has made it possible to produce quantities of pure enzyme on a commercial scale.

The encapsulation of therapeutic enzymes within autologous erythrocytes is an alternative therapeutic approach for enzyme replacement therapy, and is applicable to disorders where the pathological plasma metabolite is able to permeate the erythrocyte membrane (FIG. 1). Erythrocyte encapsulated enzyme replacement therapy has the advantage of prolonging the circulatory half-life of the enzyme and maintaining therapeutic blood levels, reducing the dosage and frequency of therapeutic interventions, and negating the need for expensive chemical modification.

In July 2006, a single dose of erythrocyte encapsulated thymidine phosphorylase was administered to a seriously ill patient with MNGIE for whom there was no other treatment. The patient was administered 1020 units thymidine phosphorylase encapsulated within $20.25 \times 10^{10}$ erythrocytes. At 3 days post infusion, the urinary excretion of thymidine and deoxyuridine decreased to 6% and 13%, respectively of the amounts excreted pre-therapy. In parallel, the plasma concentrations of these metabolites decreased during the first 3 days after infusion. Sadly, the patient died from pneumonia 21 days later. The results of this single compassionate use of this therapeutic approach are published (Moran et al., 2008).

SUMMARY OF THE INVENTION

The present invention provides significant improvements in the method used in Moran et al, 2008.

In one aspect, the invention provides a method of treating MNGIE in a patient, comprising administering to the patient autologous erythrocytes that contain thymidine phosphorylase and are free of animal proteins other than proteins derived from the patient. In particular, the erythrocytes are free from bovine serum albumin (BSA). The thymidine phosphorylase may be produced in bacteria and purified in a way that results in a very low endotoxin content. The autologous erythrocytes are typically produced by loading them with a composition comprising less than 200 EU of endotoxin per mg of thymidine phosphorylase.

The invention includes a method of producing thymidine phosphorylase that is free of animal protein, comprising releasing the thymidine phosphorylase from bacterial cells by contacting the cells with an enzyme that damages the cell wall and that is free of animal protein, typically lysozyme. The method may further comprise removing endotoxin from the thymidine phosphorylase as extracted from the cells by treating the thymidine phosphorylase extract with a detergent, forming a detergent-rich phase and a water-rich phase wherein the endotoxin partitions into the detergent-rich phase, and removing and discarding the detergent-rich phase. Steps (a), (b) and (c) are optionally repeated two or more times.

The thymidine phosphorylase is typically a bacterial thymidine phosphorylase, such as an *E. coli* thymidine phosphorylase. The *E. coli* thymidine phosphorylase may comprise the sequence of SEQ ID NO: 1 or a variant thereof.

The present invention also provides specific dosage regimes for administering autologous erythrocytes loaded with thymidine phosphorylase to a patient. The thymidine phosphorylase is typically administered to the patient at a dose from 5 IU/kg to 1,000 IU/kg. The number of autologous erythrocytes administered to the patient may be from $10 \times 10^{10}$ to $300 \times 10^{10}$, preferably from $75 \times 10^{10}$ to $150 \times 10^{10}$, and more preferably from $100 \times 10^{10}$ to $150 \times 10^{10}$.

In a further aspect, the autologous erythrocytes are administered to the patient at least once a month, at least once every two weeks or at least once a week. The thymidine phosphorylase is preferably administered at a dose of 200 IU/kg once every two weeks.

The invention also provides a composition comprising erythrocytes loaded with a bacterial thymidine phosphorylase. The invention further provides a method of preparing autologous erythrocytes that contain thymidine phosphorylase and are free of animal proteins other than proteins derived from the patient from whom the autologous erythrocytes originate, which method comprises:

(a) subjecting to hypo-osmotic dialysis a suspension of erythrocytes collected from the patient in a solution containing thymidine phosphorylase free of animal proteins, wherein the dialysis causes pores to form in the erythrocytes and thymidine phosphorylase to enter the erythrocytes;

(b) resealing the erythrocytes by exposing them to an iso-osmotic solution.

DESCRIPTION OF THE FIGURES

FIG. 17 shows bodyweights for male and female dogs throughout the acclimatization period and during four weeks of treatment. Results are expressed as mean for each group of 3 dogs.

DESCRIPTION OF THE SEQUENCE LISTING

SEQ ID NO: 1 shows the sequence of *E. coli* thymidine phosphorylase.

DETAILED DESCRIPTION OF THE INVENTION

As used in this specification and the appended claims, the singular forms "a", "an", and "the" include plural referents unless the content clearly dictates otherwise.

All publications cited herein, whether supra or infra, are hereby incorporated by reference in their entirety.

METHODS OF THE INVENTION

The invention provides a method of treating MNGIE in a patient. The method comprises administering autologous erythrocytes to the patient. The autologous erythrocytes are removed from the patient, loaded with thymidine phosphorylase and administered back to the patient. The autologous erythrocytes that are administered back to the patient do not contain any animal proteins other than those derived from the patient.

Erythrocyte encapsulated enzyme replacement therapy has the advantage of prolonging the circulatory half-life of the enzyme and maintaining therapeutic blood levels, thus reducing the dosage and frequency of therapeutic interventions, and negating the need for expensive chemical modification. Furthermore, immunogenic reactions which are often observed in enzyme replacement therapies administered by the conventional route are minimised. Erythrocyte encapsulated enzyme replacement therapy is particularly useful in patients in whom mortality from allogenic haematopoietic stem cell transplantation (HSCT) would be too high, and also for those in whom there is no matched donor. It would also be indicated as a rescue or maintenance therapy for patients with MNGIE prior to the availability of a suitable HSCT donor.

There are also a number of advantages of using autologous erythrocytes that are collected from the patient, loaded with the enzyme and then returned to the patient. For example:

There is no risk of contamination with infectious agents (e.g. viruses and prions) derived from animals.

The risk of iron overload is reduced as the patient is receiving erythrocytes that have previously been collected from them. This means higher doses of erythrocytes can be administered as frequently as is necessary for treatment.

There is a low risk of bacterial contamination as the erythrocytes can be collected from the patient, loaded with the enzyme and returned to the patient in a short space of time. Non-autologous erythrocytes would be stored for much greater lengths of time and there is therefore a higher risk of bacterial contamination.

Encapsulation is more efficient and the cells have a longer lifespan once returned to the body.

The thymidine phosphorylase loaded into the erythrocytes is free of animal proteins, specifically BSA. Conventional protocols for purifying thymidine phosphorylase involve the use of BSA as a stabilizer. The method of producing thymidine phosphorylase of the invention does not involve the use of BSA and also results in low endotoxin levels contaminating the purified enzyme.

Thymidine Phosphorylase (TP)

Figure 1:
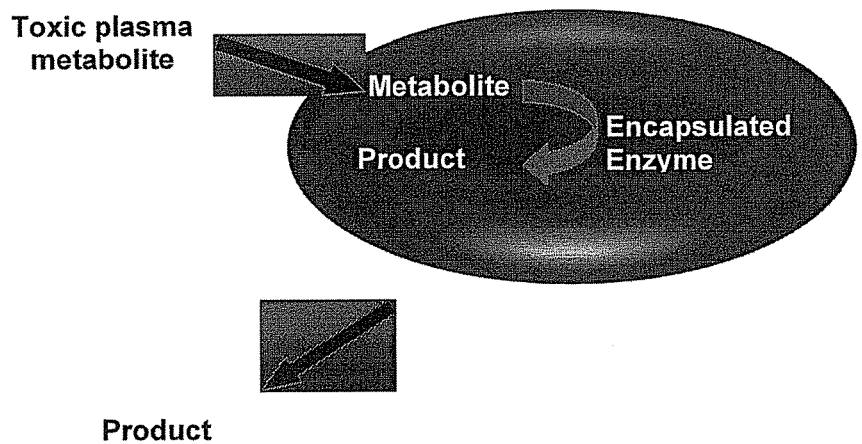
FIG. 1 shows erythrocyte-encapsulated enzyme replacement. The pathologically elevated plasma metabolite crosses the erythrocyte membrane into the cell where the encapsulated enzyme catalyses its metabolism to the normal product. The product is free to diffuse out of the cell into the blood plasma where it will be further metabolized as normal.
Figure 2:
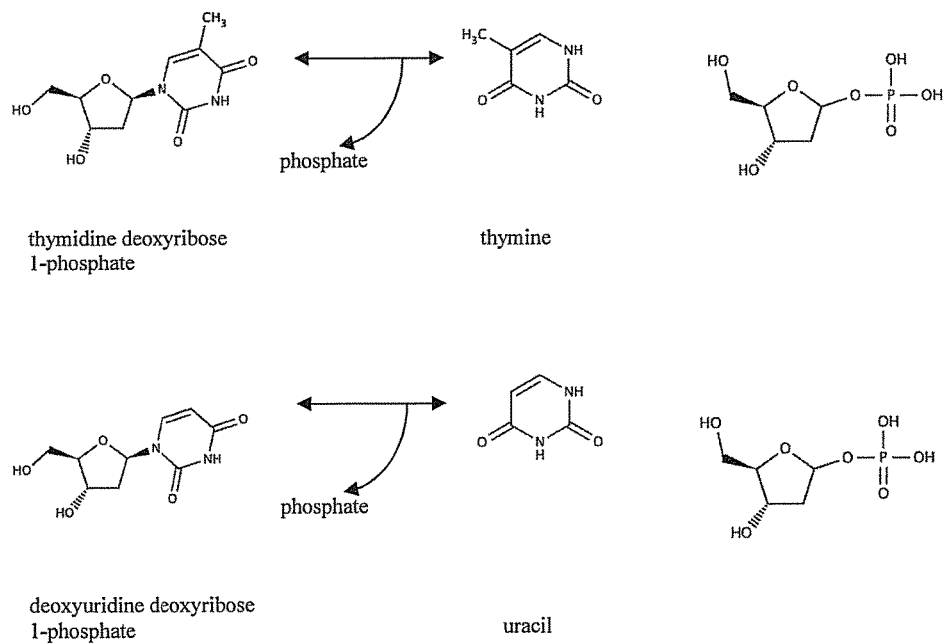
FIG. 2 shows reactions catalysed by thymidine phosphorylase.

The method of the invention involves loading erythrocytes with thymidine phosphorylase. Thymidine phosphorylase (EC 2.4.2.4), CAS Number: 9030-23-3, is an enzyme which catalyzes the reversible phosphorylation of the pyrimidine nucleosides thymidine and deoxyuridine to 2-deoxyribose 1-phosphate and their respective bases, thymine and uracil (FIG. 2). The systematic name of this enzyme class is thymidine:phosphate deoxy-alpha-D-ribosyltransferase.

The enzyme is part of the pyrimidine nucleoside salvage metabolic pathway and allows pyrimidine bases to be recycled for nucleotide biosynthesis, while the pentose 1-phosphates are converted to intermediates of the pentose phosphate shunt and glycolysis.

In humans, thymidine phosphorylase is a 55 kDa subunit homodimer, consisting of 482 amino acids (Nishino et al., 2001) and is normally expressed in platelets, lymph nodes, spleen, bladder, lung, liver, placenta, peripheral lymphocytes, brain and peripheral nerves, but is not expressed in skeletal muscle, kidney, gall bladder, aorta or adipose tissue (Usuki et al., 1990; Eccleston et al., 1995; Matsukawa et al., 1996). Enzyme activities in leuckocytes of healthy subjects are reported to be in the range of 667±205 nmol/h/mg (mean±SD) (Spinazzola et al., 2002).

In the methods of the invention, autologous erythrocytes are loaded with thymidine phosphorylase. The enzyme can be any suitable thymidine phosphorylase. The enzyme is typically a bacterial thymidine phosphorylase. The bacterial thymidine phosphorylase is preferably an *E. coli* thymidine phosphorylase. *E. coli* thymidine phosphorylase is a 47 kDa subunit homodimer consisting of 440 amino acids. *E. coli* thymidine phosphorylase shares 40% sequence identity with the human sequence (Barton et al., 1992).

The bacterial thymidine phosphorylase is more preferably a thymidine phosphorylase comprising the sequence shown in SEQ ID NO: 1 or variant thereof. A variant of SEQ ID NO: 1 is an amino acid sequence which varies from SEQ ID NO: 1 and which retains the ability to phosphorylate thymidine (or to perform the reactions shown in FIG. 2). The ability of the enzyme to phosphorylate thymidine (or to perform the reactions shown in FIG. 2) can be assayed using any method known in the art.

Over the entire length of the sequence of the amino acid sequence of SEQ ID NO: 1, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, at least 97% or at least 99% identical to SEQ ID NO: 1.

Standard methods in the art may be used to determine sequence homology. For example the UWGCG Package provides the BESTFIT program which can be used to calculate homology, for example used on its default settings (Devereux et al, 1984). The PILEUP and BLAST algorithms can be used to calculate homology or line up sequences (such as identifying equivalent residues or corresponding sequences (typically on their default settings)), for example as described in Altschul S. F. (1993) or Altschul et al. (1990). Software for performing BLAST analyses is publicly available through the National Center for Biotechnology Information (http://www.ncbi.nlm.nih.gov/).

Amino acid substitutions may be made to the amino acid sequence of SEQ ID NO: 1, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative substitutions of amino acids are well known in the art.

One or more amino acid residues of the amino acid sequence of SEQ ID NO: 1 may additionally be deleted from the polypeptides described above. Up to 1, 2, 3, 4, 5, 10, 20 or 30 residues may be deleted, or more.

One or more amino acids may be alternatively or additionally be added to the polypeptides described above. An extension may be provided at the amino terminal or carboxy terminus of the amino acid sequence of SEQ ID NO: 1 or polypeptide variant or fragment thereof. The extension may be short, for example from 1 to 10 amino acids in length. Alternatively, the extension may be longer, for example up to 50 or 100 amino acids.

The thymidine phosphorylase is typically a recombinant enzyme which is cloned and produced in over-expressing cells. For example, the *E. coli* enzyme is typically a recombinant enzyme whish is cloned and produced in over-expressing *E. coli*. Methods for cloning and expression of recombinant enzymes are well known in the art.

Purification of Thymidine Phosphorylase

The invention includes a method of producing thymidine phosphorylase that is free of animal protein, such as BSA, and contains a low amount of endotoxin.

The method comprises releasing the thymidine phosphorylase from bacterial cells by contacting the cells with an enzyme that damages the cell wall and that is free of animal protein, optionally lysozyme. The method may further comprises removing endotoxin from the thymidine phosphorylase as extracted from the cells by:

treating the thymidine phosphorylase extract with a detergent, forming a detergent-rich phase and a water-rich phase wherein the endotoxin partitions into the detergent-rich phase, and removing and discarding the detergent-rich phase;

wherein steps (a), (b) and (c) are optionally carried out two or more times (e.g from 2 to 10 times, from 2 to 5 times, typically 3 or 4 times).

The detergent is preferably a non-ionic detergent, most preferably a detergent comprising a hydrophilic polyethylene oxide (PEG) and a hydrophobic hydrocarbon group, most preferably 1,1,3,3-tetramethylbutyl)phenyl-polyethylene glycol (Triton X-100®).

The method may further comprise purifying the thymidine phosphorylase by ion-exchange chromatography.

The method may yet further comprise digesting nucleic acid with DNAse and RNAse.

As discussed above, the enzyme is typically produced in *E. coli*. The thymidine phosphorylase is typically purified from these cells by a method comprising one or more of the following steps:

(i) Harvesting the cells and resuspending the cells in buffer and stirring to form a paste. The harvested cells may be resuspended in any suitable buffer.

(ii) Lysing the cells. Lysis can be achieved with lysozyme.

(iii) Digesting the nucleic acids. The nucleic acids are typically digested with DNAse or RNAse.

(iv) Centrifuging and filtering the supernatant.

(v) Removing the endotoxins by treatment with detergent such as Triton X-114®. This typically involves repeated cycles of adding the Triton X-114®, mixing in the cold, incubating at 37° C. to partition the suspension into a detergent-rich phase and a water-rich phase, centrifuging and collecting the water-rich phase. The concentration of detergent added is preferably less than 5% (w/v), most preferably about 2% (w/v).

(vi) Ion-exchange chromatography to remove the detergent and to elute the enzyme. Any suitable method of ion-exchange column chromatography can be used, for example a Q-Sepharose column. A typical protocol involves loading the phase containing the enzyme onto the column, and washing with appropriate buffers to remove the detergent and to elute the enzyme from the column. The protein may be eluted using a high salt buffer.

(vii) Concentrating and precipitating the eluted thymidine phosphorylase.

(viii) Dialysing.

(ix) Heat treatment followed by centrifugation.

(x) Preparing the final composition. Typically, the thymidine phosphorylase is resuspended in a buffer containing uracil and thimerosal.

(xi) Final filtration.

(xii) The purified protein is usually stored at 2-8° C.

A detailed protocol for purifying thymidine phosphorylase is described in Example 1.

After purification, the concentration of thymidine phosphorylase in the final composition is typically not less than 20 mg/ml (when measured using the Biuret-TCA method). Protein concentrations can be measured using any suitable method.

The activity of the protein in the final composition is at least 900 units/ml, preferably at least 2,000 units/ml, more preferably at least 3,000 units/ml and most preferably at least 4,500 units/ml. A unit refers here to the amount of enzyme that catalyzes the conversion of 1 µM substrate to product in 1 minute at 25° C.

The concentration of endotoxin in the final composition is typically less than 4,000 EU/ml, preferably less than 3,000 EU/ml, more preferably less than 2,000 EU/ml and most preferably less than 1,500 EU/ml. The concentration of endotoxin in the final composition may be less than 1,000 EU/ml or may even be less than 500 EU/ml. One EU (Endotoxin Unit) is equivalent to about 0.1 to 0.2 ng endotoxin. The concentration of endotoxin can be measured using any suitable assay, for example the *Limulus Amebocyte* Lysate assay.

The ratio of enzyme to endotoxin in the final composition (endotoxin units/units of thymidine phosphorylase) is typically less than 5, preferably less than 2, more preferably less than 1 and most preferably less than 0.5.

The concentration of detergent (e.g. Triton X-114®) in the final composition is typically less than 0.01%, preferably less than 0.05% and more preferably less than 0.001%.

The final composition also typically contains less than 10 ppb, preferably less than 1 ppb, more preferably less than 0.1 ppb and most preferably less than 0.01 ppb residual DNA. DNA concentrations can be measured using any suitable means, for example qPCR.

Autologous Erythrocytes Loaded with Thymidine Phosphorylase

The methods of the invention involve loading autologous erythrocytes with the bacterial thymidine phosphorylase. In this approach, erythrocytes are collected from the patient, the enzyme is loaded into the erythrocytes and the erythrocytes loaded with the enzyme are returned back into the patient.

Typically, whole blood is collected from the patient aseptically, preferably into sterile tubes containing low molecular weight heparin and dalteparin sodium (such as 9 units/ml blood).

The erythrocytes may be removed from the patient and loaded with the bacterial thymidine phosphorylase by any suitable means known in the art. The erythrocytes may be loaded with the enzyme by iso-osmotic lysis induced by high voltage electric fields or by hypo-osmotic haemolysis either by direct dilution with a hypo-osmotic solution or by dialysis in which the cells are dialysed against a hypo-osmotic solution. (Ihler et al., 1973; Sprandel et al., 1979).

Figure 3:
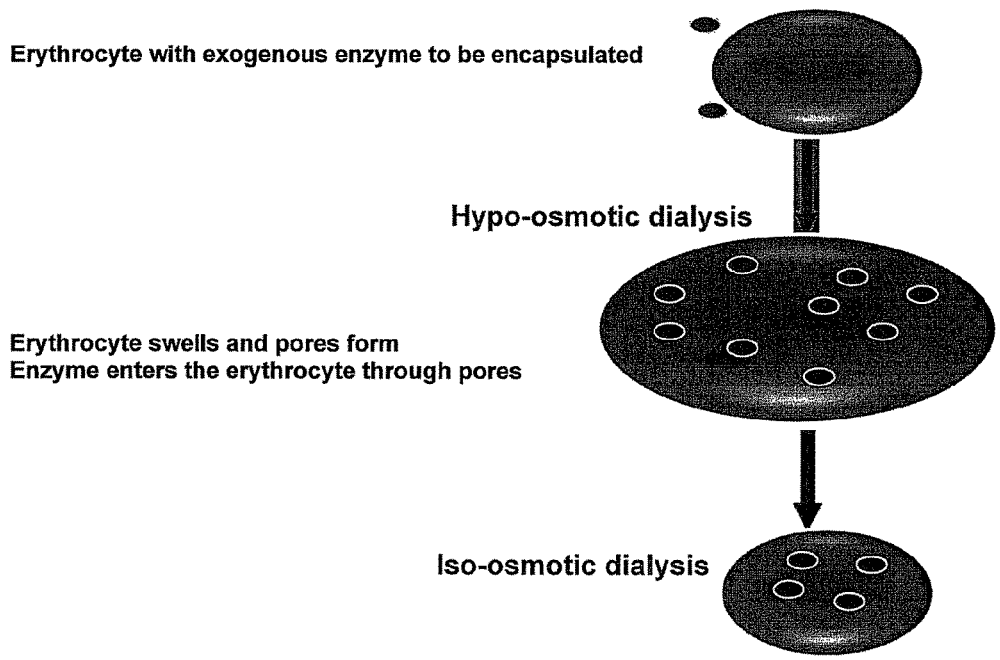
FIG. 3 shows encapsulation of exogenous enzyme using the hypo/iso-osmotic dialysis technique.

The enzyme is preferably loaded into the erythrocytes using hypo-osmotic dialysis. Under hypo-osmotic conditions, the erythrocytes swell due to an influx of water until at a critical size, pores form in the membrane. While permeable, therapeutic drugs and enzymes are able to enter the erythrocytes by diffusion. The permeability is reversed by restoration of iso-osmotic conditions, encapsulating the therapeutic agent within the erythrocytes, which are then returned to the patient (FIG. 3).

Erythrocytes prepared using hypo-osmotic dialysis retain to a greater extent the biochemical and physiological characteristics of the intact erythrocyte.

The hypo-osmotic dialysis procedure is described by Bax et al 1999. Briefly, erythrocytes are washed in phosphate buffered saline containing the therapeutic enzyme. The cells are dialysed against a hypo-osmotic buffer and the erythrocytes are resealed by transferring the dialysis bags into pre-warmed iso-osmotic phosphate buffered saline supplemented with adenosine, glucose and $MgCl_2$. This process is described in more detail in Example 1.

It has been shown that the addition of glucose, magnesium chloride and adenosine to the resealing buffer, and the use of low centrifugation speeds during the washing steps, allows the erythrocytes to maintain normal cellular morphology and retain soluble cytoplasmic proteins and biochemical parameters (Sprandel et al, 1981; Bax et al., 2000).

The enzymes are loaded with an appropriate concentration of therapeutic enzyme. The erythrocyte concentration of enzyme is typically in the range of 10 to 150 IU per $1 \times 10^{10}$ cells, preferably in the range of 20 to 75 IU per $1 \times 10^{10}$ cells and more preferably in the range of 25 to 50 IU per $1 \times 10^{10}$ cells. An IU (International Unit) is here equal to the amount of enzyme required to convert 1 µmol of substrate to product per minute at 37° C.

Administering to the Patient Erythrocytes Loaded with Bacterial Thymidine Phosphorylase In the methods of the invention, autologous erythrocytes loaded with bacterial thymidine phosphorylase are administered back to the patient from which they were originally removed.

After hypo-osmotic dialysis, erythrocytes loaded with the enzyme are then typically resuspended in an equal volume of autologous plasma and returned to the patient by slow intravenous infusion.

The number of autologous erythrocytes administered to the patient is typically from $50 \times 10^{10}$ to t $300 \times 10^{10}$, preferably from $75 \times 10^{10}$ to $200 \times 10^{10}$, and more preferably from $100 \times 10^{10}$ to $200 \times 10^{10}$.

The dose of bacterial thymidine phosphorylase administered to the patient per treatment is typically in the range of 350 IU to 70,000 IU, more preferably 1,000 IU to 20,000 IU and most preferably 2,500 to 10,000 IU.

The erythrocytes loaded with thymidine phosphorylase are typically administered to the patient at a dose of thymidine phosphorylase from 5 to 1,000 IU/kg, 30 to 300 IU/kg, 50 to 200 IU/kg or 75 to 150 IU/kg, preferably at a dose of 200 IU/kg.

The process of administering autologous erythrocytes loaded with bacterial thymidine phosphorylase to a patient is carried out as frequently and as many times as necessary. Doses of the enzyme and the frequency of the treatment will depend on the clinical situation of the patient. Treatment may be carried out at least once a month, preferably at least once every two weeks and more preferably at least once a week. Even more preferably, treatment is carried out once every two weeks. Most preferably, treatment is carried out once every two weeks with a dose of 200 IU/kg thymidine phosphorylase. Treatment is typically carried out over the lifetime of the patient. Treatment may be for a time period of at least 3 months, at least 12 months or at least 24 months.

As a result of treatment, the concentration of thymidine or deoxyuridine in the patient's blood plasma may be reduced to 70% or less of the pre-treatment level at a time point of from 3 to 12 months, preferably 6 to 10 months, after the start of treatment. The concentration of thymidine or deoxyuridine is preferably reduced to 60% or less, 50% or less, 40% or less, 30% or less, 20% or less, 5% or less, 2% or less or 0% of the pre-treatment level. The concentration is typically measured mid-cycle or 5 days after a dose.

The concentration of thymidine or deoxyuridine in the patient's urine may be reduced to less than 70%, less than 50%, less than 30%, less than 20%, less than 10%, less than 5%, less than 2% or 0% of the pre-treatment concentration at a time point of 3 to 12 months, preferably 6 to 10 months, after the start of treatment. The concentration is typically measured mid-cycle or 5 days after a dose.

Composition

The present invention also relates to a composition comprising autologous erythrocytes loaded with a bacterial thymidine phosphorylase. Such bacterial thymidine phosphorylases are described above. The amount of thymidine phosphorylase in the erythrocytes is typically in the range of 350 IU to 10,000 IU.

Method of Preparing Autologous Erythrocytes Loaded with Bacterial Thymidine Phosphorylase The invention also relates to preparing erythrocytes loaded with a bacterial thymidine phosphorylase. The method involves collecting erythrocytes from a patient and subjecting the erythrocytes to a hypo-osmotic dialysis procedure. The hypo-osmotic dialysis procedure is described in detail above.

The following Examples illustrate the invention:

Example 1—Encapsulation and Incubation Procedure

Method 7 volumes of washed and packed erythrocytes were mixed with 3 volumes of cold phosphate buffered saline containing an appropriate concentration of therapeutic enzyme. The suspension was then placed into dialysis bags with a molecular weight cut-off of 12,000 daltons. Cells were dialysed against hypo-osmotic buffer (5 mmol/l $KH_2PO_4$, 5 mmol/l $K_2HPO_4$, pH 7.4) at 4° C. in a specially modified LabHeat refrigerated incubator (BoroLabs, Berkshire, UK) with rotation at 6 rpm for 120 minutes. Erythrocyte resealing was achieved by transferring the dialysis bags to containers of pre-warmed iso-osmotic phosphate buffered saline supplemented with 5 mmol/l adenosine, 5 mmol/l glucose and 5 mmol/l $MgCl_2$, pH 7.4, and rotation continued at 6 rpm for 60 minutes in a LabHeat incubator set at 37° C. The enzyme-loaded erythrocytes were washed three times in 3 volumes of supplemented phosphate buffered saline with centrifugation at 100×g for 20 minutes.

Encapsulation Results

Figure 4:
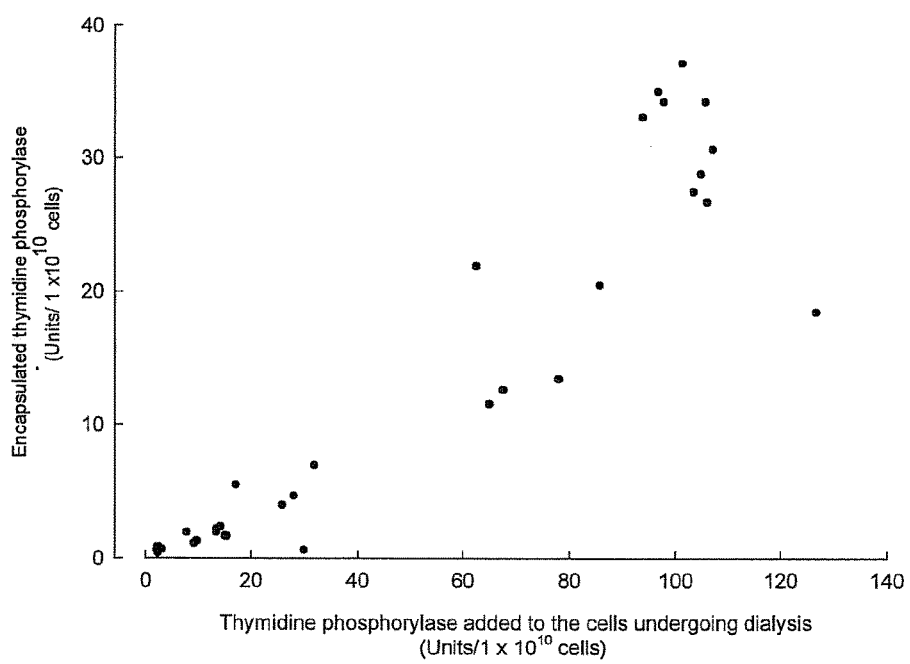
FIG. 4 shows encapsulation of thymidine phosphorylase by human erythrocytes as a function of enzyme activity added to the dialysis process. Each point represents one dialysis experiment. One unit of activity is defined as the amount of enzyme required to convert 1 µmol of thymidine to thymine per minute at 37° C.

It has been shown that catalytically active recombinant thymidine phosphorylase from E. coli can be successfully encapsulated within human erythrocytes. FIG. 4 shows the encapsulation of thymidine phosphorylase by human erythrocytes as a function of enzyme units added to the hypo-osmotic dialysis process. The activity of enzyme encapsulated increased as a function of enzyme activity added to the dialysis, up to a concentration of approximately 100 International Units (IU) per $1\times10^{10}$ cells; the efficiency of entrapment decreased when concentrations greater than this were used. The range of activity that could be encapsulated using this higher enzyme concentration was 24-38 IU per $1\times10^{10}$ cells.

Incubation Experiments

Figure 5:
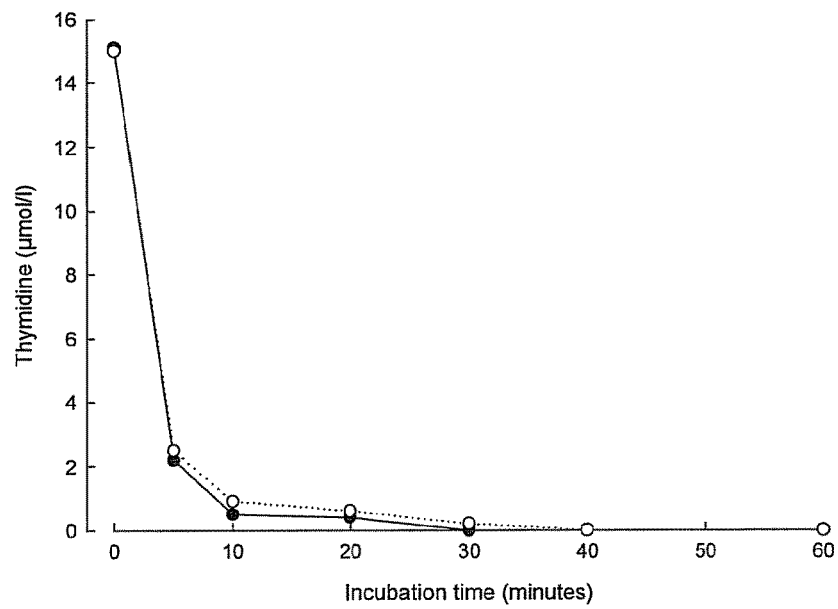
FIG. 5 shows the metabolism of extracellular thymidine by thymidine phosphorylase-loaded erythrocytes as a function of incubation time. Enzyme-loaded erythrocytes were incubated in: • plasma from a patient with MNGIE, and ○ phosphate buffered saline containing 15 µmol/l thymidine.

It has been demonstrated that recombinant thymidine phosphorylase-loaded erythrocytes incubated at a haematocrit of 25% in either phosphate buffered saline containing 15 mmol/l thymidine, or plasma taken from a patient with MNGIE, are able to reduce the extracellular incubation concentrations of thymidine. FIG. 5 shows the concentration of thymidine in the incubation media as a function of incubation time. After 5 minutes of incubation, the encapsulated enzyme had metabolised approximately 87% of the extracellular thymidine in both the phosphate buffered saline and plasma, and by 40 minutes all the thymidine had been metabolised. Thymidine phosphorylase activity was undetectable in the extracellular media. These in vitro studies demonstrate that extracellular thymidine is able to permeate the erythrocyte membrane and undergo metabolism by the encapsulated thymidine phosphorylase, and thus provide the justification for in vivo studies in patients with MNGIE.

Example 2—Treatment of MNGIE

The female patient was 25 years old at the start of this study. She had always been thin and the diagnosis of anorexia nervosa had been considered during adolescence. At the age of 23 years a mild peripheral neuropathy developed to be quickly followed by symptoms of intestinal dysfunction with anorexia, nausea, abdominal pain and bloating. An external ophthalmoplegia was noted soon afterwards. The peripheral neuropathy and intestinal dysmotility had been relentlessly progressive such that the patient required the use of a wheelchair, total parenteral nutrition, and regular pro-kinetic and anti-emetic medications.

The patient is the second youngest of four siblings, one boy and 3 girls, born to parents who were first cousins. The eldest brother died age 17 years with an undiagnosed illness marked by intestinal dysmotility from the age of 2 years, initially vomiting and to a lesser extent diarrhoea. From the age of 12 years there were recurrent episodes of intestinal pseudo-obstruction with on-going anorexia and cahexia. In the few months before death a peripheral polyneuropathy developed. The youngest sister developed a peripheral neuropathy at the age of 18 years that within 10 months was accompanied by intestinal dysfunction with anorexia, vomiting and cahexia. There was rapid deterioration, and death was 22 months after first onset of symptoms.

To date the patient has received 31 treatment cycles over a period of 24 months. Initially the patient received intravenous infusions of bacterial thymidine phosphorylase-loaded erythrocytes once every four weeks, starting at a dose of 6 IU/kg (total dose 200 IU). The thymidine phosphorylase was that of SEQ ID NO: 1. The dose has been gradually escalated to 20 IU/kg once every two weeks, administered as a 30 minute infusion in a hospital setting. It is anticipated that the dose could be increased to 150 IU/kg.

Figure 6:
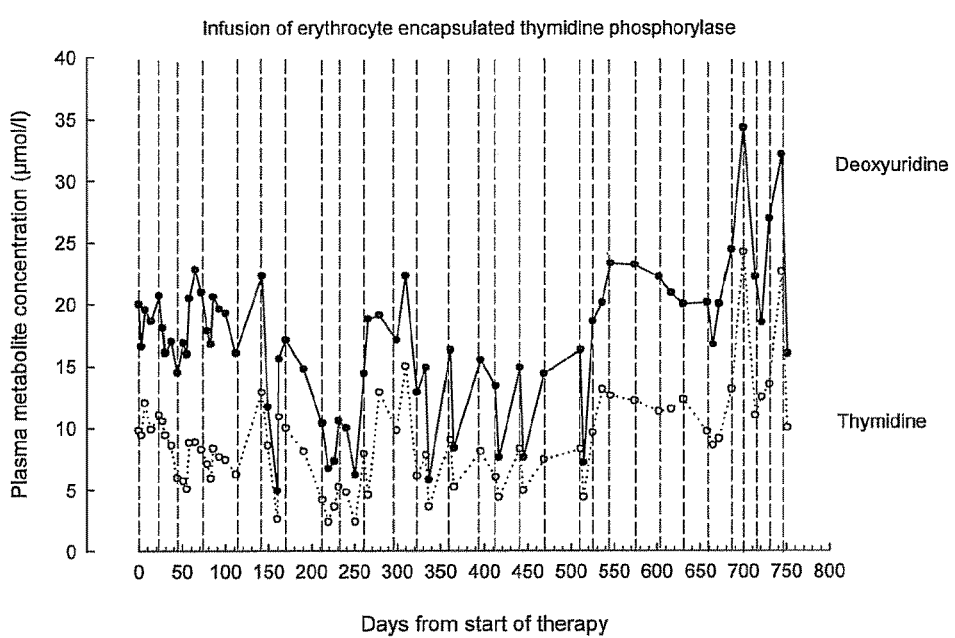
FIG. 6 shows plasma thymidine and deoxyuridine concentrations during escalating doses of erythrocyte-encapsulated enzyme. One unit of activity is defined as the amount of enzyme required to convert 1 µmol of thymidine to thymine per minute at 37° C.

Initial administration of erythrocyte encapsulated enzyme reduced pre-therapy plasma concentrations of thymidine and deoxyuridine from 9.8 µmol/l and 20.0 µmol/l respectively to mid-cycle concentrations of 2.4-5.2 µmol/l for thymidine, and 6.2-10.6 µmol/l for deoxyuridine, by day 250 (FIG. 6). At day 240, total parenteral nutrition was commenced on clinical grounds with the aim of providing total calorie requirement by this route. Over the next 250 days intra-cycle concentrations were maintained at similarly reduced levels, but the end cycle concentrations were higher than previously, but still lower than pre-treatment levels. From day 550, end cycle levels were equal to or higher than pre-treatment levels; this coincided with the development of lipaemia and lipiduria from the total parenteral nutrition. When intra-cycle blood sample were possible, these revealed significant reductions in the plasma metabolite concentrations from end cycle values. The effect of erythrocyte encapsulated enzyme on the plasma metabolites is therefore confounded by the administration of total parenteral nutrition, the lipid component of which is known to be hepato-toxic and metabolised by the mitochondrion, the site of the primary pathology in this condition. Lipid is known to be adsorbed onto the surface of the red cell membrane and this effect on erythrocyte encapsulated therapy is unclear.

Figure 7:
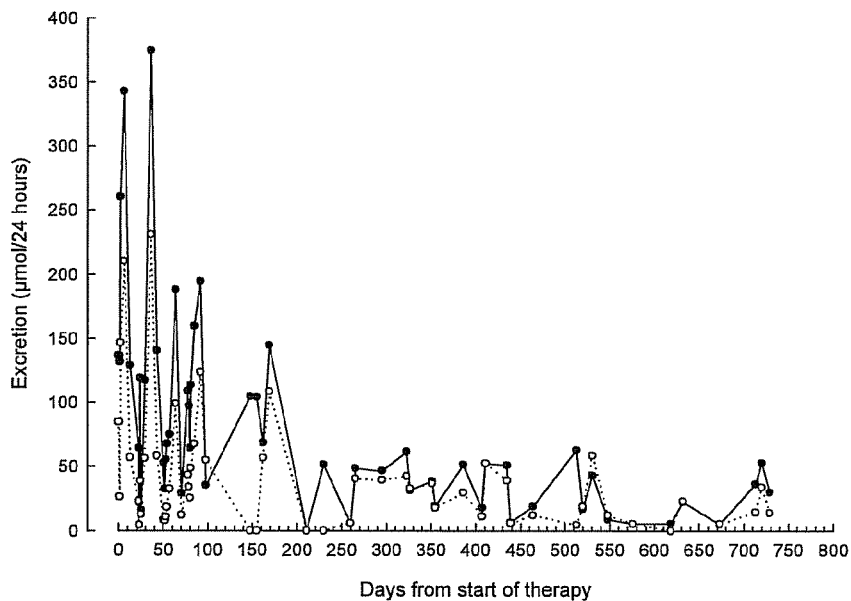
FIG. 7 shows urinary excretion of thymidine (o) and deoxyuridine (●) during escalating doses of erythrocyte encapsulated enzyme.

The excretion of urinary metabolites decreased from pre-treatment values of 85 µmol/24 hours and 137 µmol/24 hours respectively, for thymidine and deoxyuridine, to levels between 0-58 µmol/24 hour for thymidine, and 0.3-63 µmol/24 hours for deoxyuridine from day 210 onwards (FIG. 7).

Clinical benefit is currently being evaluated longitudinally by conducting neurological assessments, liver and renal function tests, quality of life scoring scales, and clinical and disease scoring scales.

Figure 8:
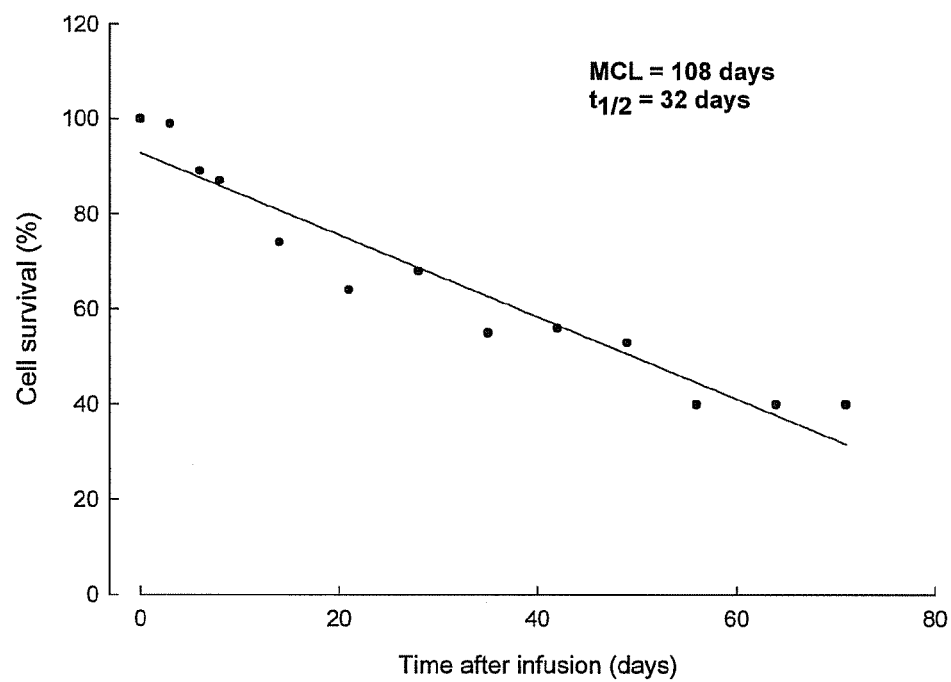
FIG. 8 shows in vivo survival of thymidine phosphorylase-loaded autologous erythrocytes in a patient with MNGIE, as measured by 51Cr-labelling. MCL=mean cell life, t½=half life.

An erythrocyte chromium [$^{51}$Cr]-labelling study of thymidine phosphorylase loaded erythrocytes prepared from this patient demonstrated a normal circulating mean cell life, and half-life of 108 and 32 days, respectively (FIG. 8) demonstrating the viability of the erythrocyte as a vehicle for sustaining therapeutic blood levels of enzyme. No antibodies against thymidine phosphoylase have been detected, as measured by our Enzyme-linked Immunosorbant Assay (ELISA). The patient has tolerated the therapy and, three months after initiating therapy, the patient reported a reduction in the number of nausea and vomiting attacks and gained 4 kg in weight.

Figure 9:
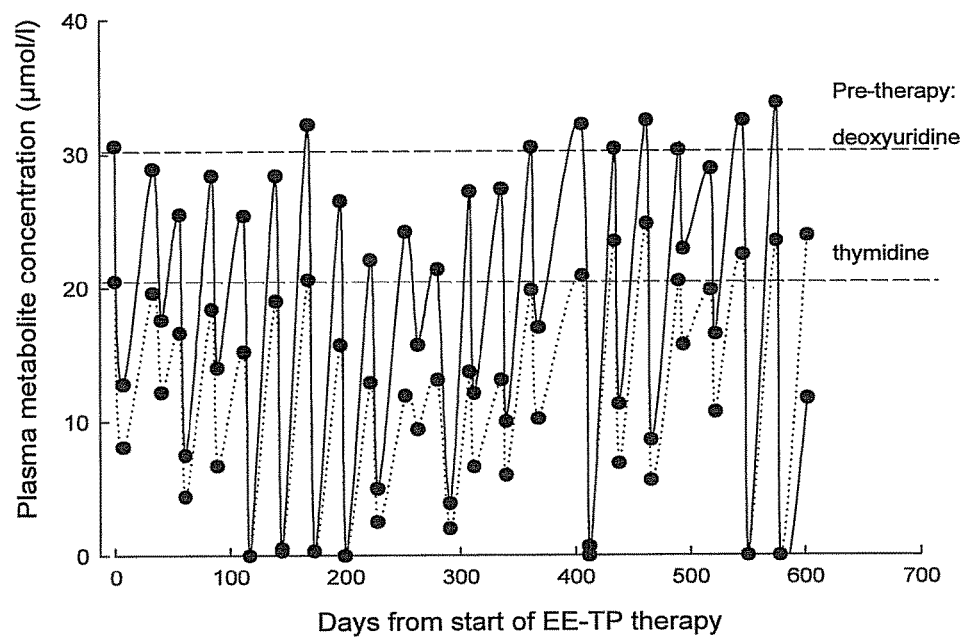
FIG. 9 shows thymidine and deoxyuridine concentrations in plasma during the therapy of the invention.
Figure 10:
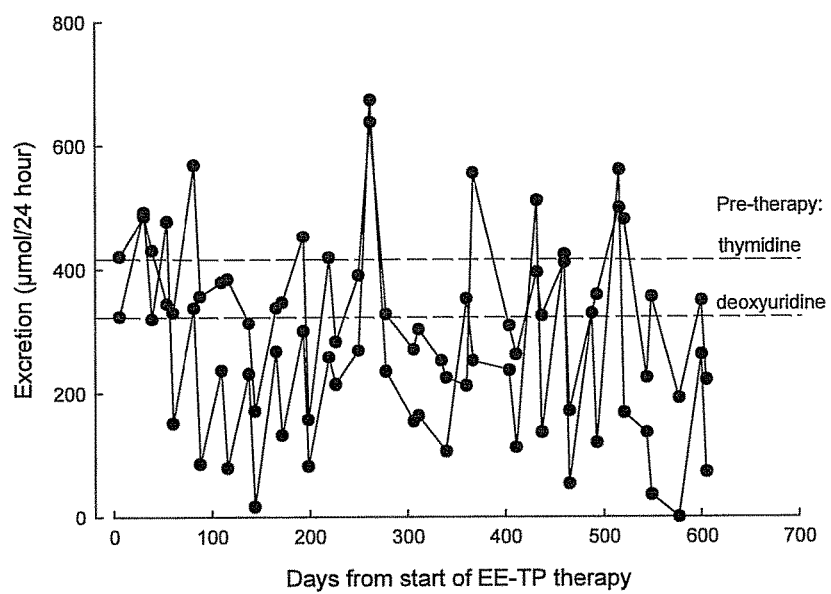
FIG. 10 shows thymidine and deoxyuridine concentrations in urine during the therapy of the invention.
Figure 11:
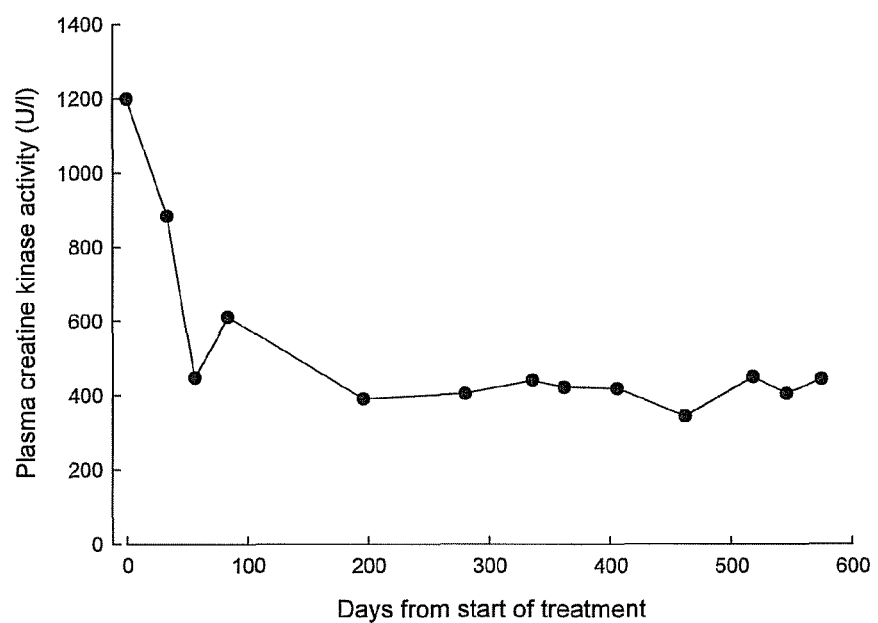
FIG. 11 shows plasma creatine kinase activity during 22 cycles of escalating doses of EE-TP.

Results for another patient are shown in FIGS. 9, 10 and 11. This patient was a male who presented at 26 years of age with peripheral sensorimotor polyneuropathy, external ophthalmoplegia but minimal intestinal dysmotility. EE-TP therapy was initiated 3 months after diagnosis. EE-TP was prepared using the hypo-osmotic dialysis procedure. Treatment cycles were approximately once per month. The patient has received 22 cycles of escalating doses of EE-TP (17 to 44 IU/kg).

Reductions in intra cycle plasma nucleosides, urinary nucleoside excretion and creatine kinase activity were observed and maintained (FIGS. 9, 10 and 11). One unit of TP activity is defined as the amount of enzyme required to convert 1 µmol of thymidine to thymine per minute at 37° C.

After 18 months of therapy, the patient showed improved gait and balance and improved sensory ataxia and fine finger function.

Disease rating scores are shown in Table 1. These scores mostly reflected improvements in foot drop and exercise tolerance.

TABLE 1

Scores from disease rating scales

| Scale | Pre-therapy | 1 year | 1.5 years |
|---|---|---|---|
| SF36: | | | |
| Physical component (population mean 50 ± 10) | 51 | 52 | 55 |
| Mental component (population mean 50 ± 10) | 52 | 51 | 52 |
| Newcastle mitochondrial disease scale (normal = 0): | | | |
| I (general neurological functioning) | 4 | 3 | 3 |
| II (system specific functioning) | 2 | 2 | 2 |
| III (clinical assessment) | 11 | 11 | 11 |
| MRC neurological scores: | | | |
| Motor (normal = 100) | 62 | 68 | 74 |
| Sensory (normal = 0, maximum score = 64) | 21 | 21 | 18 |
| Overall neuropathy limitation scale (0 = no disability, 12 = maximum disability) | 3 | 3 | 3 |

Example 3—Purification of Thymidine Phosphorylase

Thymidine kinase was purified from an *E. coli* cell pellet. The *E. coli* were transfected to over-express thymidine kinase of SEQ ID NO: 1, grown and harvested using standard techniques.

The cell pellet (300 g cells) was resuspended in 750 ml 10 mM Tris, 1.5 mM EDTA pH 7.5 buffer with stirring for 30 minutes. Cells were lysed using 4.5 million units of lysozyme of animal-free origin. The nucleic acids were digested by adding 3,000 units DNAse and 600 units RNAse (also of animal-free origin) with stirring for 60 minutes.

The suspension was centrifuged at 15,000 g for 1 hour. The supernatant was filtered through 5 µm and 0.8 µm filters. The pH was adjusted to 8.0.

Figure 12:
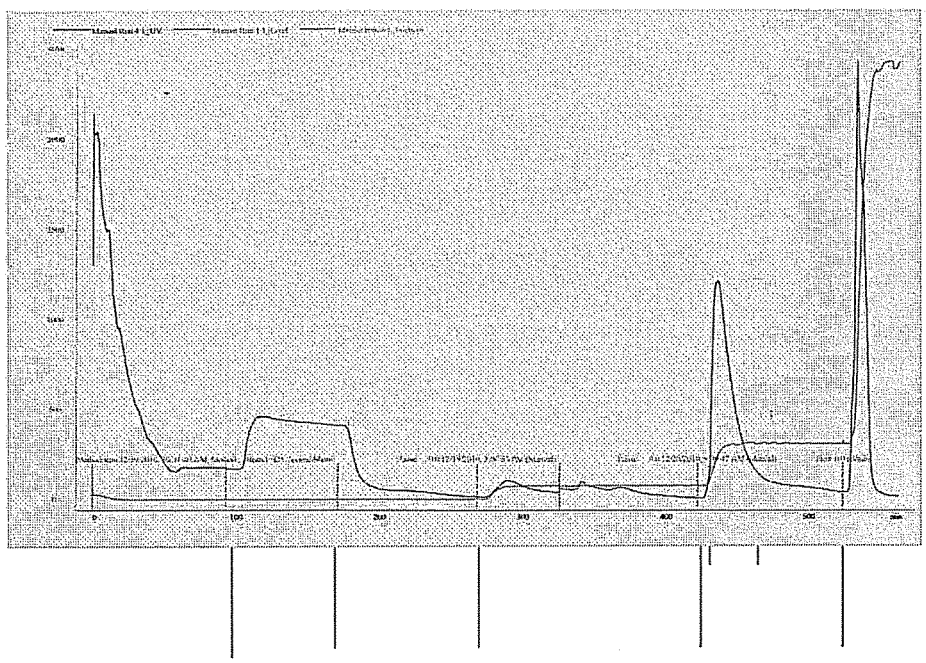
FIG. 12 shows a chromatogram from a Q-Sepharose column. During the washes with Tris buffer, Triton X-100®, 45 mm NaCl and 2 M NaCl, other non-relevant proteins are eluted out of the column as well as the Triton X-114®. The relevant thymidine phosphorylase is eluted with 200 mM NaCl in a distinct peak, which was collected separately (phase II of the 200 mM NaCl elution).

Endotoxin was removed by treatment with Triton X-114®. 20% (W/V) Triton X-114® was added to the supernatant at 1/10 of the volume, followed by mixing in the cold for 30 minutes, incubating at 37° C. for 1 hour and centrifuging for 40 minutes at 20,000 g at 25° C. The upper phase was collected and the cycle repeated an additional three times. The final upper phase was then added to a Q-sepharose column at 5 ml/min. The column was washed with 7 column volumes of 20 mM Tris pH 8; 7 column volumes of 10 mM Tris, 0.1% (w/v) Triton X-100® pH 8; 7 column volumes of 20 mM Tris pH 8; and 8 column volumes of 20 mM Tris, 45 mM NaCl pH 8. The thymidine phosphorylase was then eluted with 7 column volumes of 20 mM Tris, 200 mM NaCl pH 8, and the column was finally washed with 2 M NaCl. The chromatogram of the Q-sepahrose column is shown in FIG. 12.

The concentration of the thymidine phosphorylase was determined by measuring the absorbance at 280 nm, and the protein was concentrated to an $OD_{280}$ 19-25 using spin concentration (10 KD molecular weight cut off). Ammonium sulphate was added to 65% saturation and mixed overnight.

The solution containing the protein was centrifuged at 22,000 g for 40 minutes and the pellet resuspended in the minimum volume of 10 mM potassium phosphate, 2.9 mM uracil pH 6.8. The solution was dialysed against 2×2 L of 10 mM potassium phosphate, 2.9 mM uracil pH 6.8.

Figure 13:
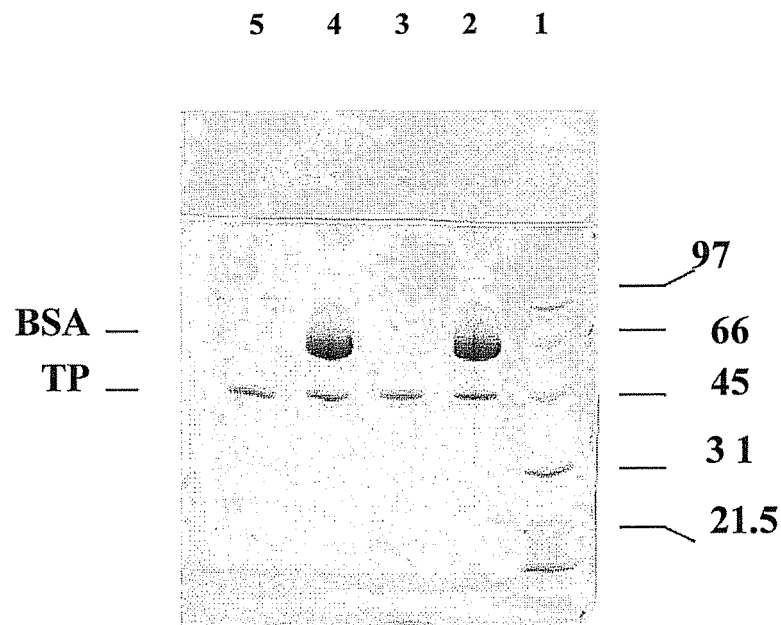
FIG. 13 shows SDS-PAGE on 12.5% Phast of diluted samples of purified thymidine phosphorylase of the invention (pilot batch W1234), and a control (T6632) which contains both thymidine phosphorylase and BSA. The pilot batch, which co-migrated with the TP band of the control, is approximately 5× more concentrated than the control (diluted 1:100 vs 1:20 dilution of the control). The BSA band is missing in the pilot batch since it is not part of the final formulation. 1: Size marker; 2,4: Control T6632, lot 118K8720 diluted 1:20; 3,5: W1234 lot 11101111 diluted 1:100.

The dialyzate was incubated in glass Erlenmeyer in a 40° C. waterbath for 30 mins then cooled to 10° C. before centrifugation at 22,000 g for 60 minutes. The supernatant was collected and 0.25 volumes of 2.5 M potassium phosphate, 10 mM uracil, 0.1% (w/v) thimerosal added and mixed well. The composition was filtered through a 0.22 μm filter and the final product stored at 2-8° C. Endotoxin levels were measured by the Limulus Amebocyte Lysate assay, and Triton X-114® concentrations were determined by HPLC. The final concentration of thymidine phosphorylase was determined by the Biuret-TCA assay, protein purity checked by SDS-PAGE (results shown in FIG. 13) and N-terminal sequencing. The activity of the purified protein determined by the thymidine phosphorylase activity assay. The residual concentration of DNA was checked by qPCR.

The production of a potent IP with low endotoxin level has been accomplished. We were able to reduce the endotoxin level, using Triton X-114, from an original level of millions EU/ml to 1,655 EU/ml without reducing the TP activity and with no traces of Triton X-114. We reduced the ratio EU/TP by 1 order of magnitude, from 5.3 to 0.35 in the final product.

TABLE 2

Analytical Results

| Test | Assay | Results | Proposed specifications |
|---|---|---|---|
| Appearance | Visual inspection | Slightly hazy, light yellow liquid | Slightly hazy, light yellow liquid |
| Protein | Biuret-TCA | 31.3 mg/ml | >20 mg/ml |
| Activity | TP activity assay | 4,686 U/ml | At least 900 units/ml |
| Size | SDS-PAGE | Similar to control TP band | Similar to control TP band |
| Endotoxin | Limulus Amebocyte | 1,655 EU/ml | <4000 EU/ml |
| Triton X-114 | HPLC | <0.001% | NMT 0.01% |
| Purity | N-terminal sequence | Matches TP N-terminal amino acid sequence (NCBI blast) | Matches TP Nterminal amino acid sequence (NCBI blast) of MFLAQEIIRK |
| Residual DNA | qPCR | 0.01 ppb | <10 ppb |
| Bioburden | | 3 CFU/ml | <10 CFU/ml |
| Kanamycin | LC-MS-MS | 0.23 ppm | <10 ppm |

TABLE 3

Volume, TP activity and endotoxin range after each purification step

| | Volume (mL) | TP activity (U/mL) | Total TP activity | Yield of TP activity | Endotoxin EU/ml |
|---|---|---|---|---|---|
| After lysis and filtration | 620 | 1,737 | 1,076,940 | 100% | >3,000,000 |
| After 4 cycles of Triton treatment | 260 | 1,656 | 430,560 | 40% | 3,000-30,000 |
| Eluted protein from column | 410 | 618 | 253,380 | 23% | 30-300 |
| After final formulation | 43 | 4,686 | 206,184 | 19% | 1,655 |

Example 4—Development of an Immunoassay for the Measurement of Anti-Thymidine Phosphorylase Antibodies in Mouse and Dog Sera 1. Materials and Methods Assays were validated according to Food and Drug Administration (FDA) and European Medicines Agency (EMA) guidelines and the study was conducted in compliance with Good Laboratory Practice (GLP) standards (FDA 2001; FDA 2009; EMEA 2006; Miller et al., 2001; Mire-Sluis et al., 2004; Shankar et al., 2008; The Good Laboratory Practice Regulations; OECD Principles of Good Laboratory Practice; EC Commission Directive 2004/10/EC).

1.1 Reagents

Recombinant E. coli thymidine phosphorylase (TP, 26.6 mg/mL) the therapeutic enzyme candidate produced for GLP pre-clinical studies was employed in the development and validation of this immunoassay (Sigma-Aldrich, Israel). Affinity-purified rabbit anti-TP antibody (0.518 mg/mL) was custom produced (Open Biosystems, USA). The wash buffer was phosphate-buffered saline (PBS, Sigma-Aldrich, UK) with 0.05% Tween 20 (Sigma-Aldrich, UK). Blocker A solution consisted of 5% (w/v) Blocker A in MSD phosphate buffer (Meso Scale Discovery, USA). The assay buffer (PBS, 0.05% (v/v) Tween 20, 1% (w/v) Blocker A) consisted of 1 volume of 5% Blocker A solution and 4 volumes of wash buffer. The Read buffer T (4×) was supplied by Meso Scale Discovery, USA and was diluted 1 in 2 with ultra high purity grade water.

1.2 Preparation of Biotinylated and Sulfo-TAG TP Conjugates

The bridging immunoassay format requires TP to be conjugated with biotin and conjugated with sulfo-TAG; biotinylated TP served as the capture antigen and the sulfo-TAG conjugated TP as the detection antigen. TP was conjugated with biotin using EZ-Link sulfo-NHS biotin kit (Pierce Biotechnology, USA). TP was first desalted using a zebra desalt spin column (Pierce Biotechnology, USA) equilibrated with PBS, with centrifugation at 1000 g for 2 minutes, and then diluted with PBS to form a secondary stock solution of 10 mg/mL. A calculated volume of EZ-Link sulfo-NHS biotin was added directly to 500 μL of TP secondary stock solution and incubated for 30 minutes, with mixing at room temperature. Biotin conjugated TP was desalted using a Zebra desalt spin column equilibrated with PBS, with centrifugation at 1000 g for 2 minutes and stored at 4° C. until use.

Conjugation of TP with Sulfo-TAG was performed using Sulfo-TAG NHS ester (Meso Scale Discovery, USA). TP was first desalted as described above and diluted with PBS to form a secondary stock solution of 10 mg/mL. A calculated volume of sulfo-TAG ester was added to 350 μL TP secondary stock solution and incubated with mixing for 2 hours at room temperature. The sulfo-TAG TP conjugate was desalted as described above and stored at 4° C. until use.

1.3 Negative Control Sera Pools

Individual dog (n=11) and mouse (n=15) sera samples were screened by analysis (n=1 in duplicate) against positive control calibration curves for the presence of anti-TP antibodies. Blank sera from individual dogs and mice were pooled to produce negative control dog and mouse sera pools, respectively. These were stored at −20° C. until required for defining the cut-point and preparing Quality Control (QC) samples and calibration curves.

1.4 Positive Control Standards

Primary positive control standard stock of anti-TP antibodies (0.518 mg/mL) was diluted with negative control sera (dog or mouse as appropriate) to form a secondary positive control standard stock of 100 μg/mL and this was further diluted with negative control sera (dog or mouse as appropriate) to form a tertiary positive control standard stock of (25,000 ng/mL). The tertiary standard stock was diluted with negative control sera (dog or mouse as appropriate) to produce working standards over the range 2.50 ng/mL to 7,500 ng/mL. Prior to analysis the positive control standards were diluted 1 in 10 with assay buffer.

1.5 Validation QC Samples

Pooled negative control sera from dog and mouse were spiked with anti-TP antibodies to provide three concentrations relative to the cut point: low (just above cut point), middle (mid assay dynamic range) and high (high assay dynamic range). The negative control sera were used as the negative control QC standards. All QC samples were prepared in 20 μL aliquots and stored at −70° C. Prior to assay the QC samples were diluted 1 in 10 using 10 μL QC sample and 90 μL assay buffer.

1.6 Immunoassay Procedure

Assays were performed using a bridging electrochemiluminescent (ECL) immunoassay. Briefly, 25 μL positive control standard, blank, negative control, QC samples and test samples (with or without thymidine phosphorylase as appropriate) were added to wells of a polypropylene 96-well plate (Fisher Scientific, UK) followed by 50 μL of conjugate Mastermix (0.0625 μg/mL biotin TP/0.0313 μg/mL sulfo-TAG TP, using assay buffer as the diluent). The plates were covered and incubated at room temperature for 2 hours on a microtitre plate shaker set at 600 rpm (Micromix, DPC Ltd, Wales). Following the start of this incubation, 150 μL Blocker A solution were added to each well of a multi-array 96-well standard streptavidin plate (Meso Scale Discovery, USA), which was then covered and incubated at room temperature for 2 hours with shaking at 600 rpm. The multi-array plate was then washed three times with 200 μL wash buffer per well using a microtitre plate washer (Well-wash, Thermo Life Sciences Ltd, UK). The last wash was aspirated and the plate blotted dry by inversion over absorbant paper. Fifty microliters from each well of the polypropylene 96-well plate were transferred to corresponding duplicate wells in the multi-array 96-well standard streptavidin plate. The multi-array plate was then covered, incubated at room temperature for 1 hour, with shaking at 600 rpm, and this was then followed by three washes with 200 μL wash buffer per well using the plate washer. The last wash was aspirated and the plate blotted dry by inversion over absorbant paper. Finally 150 μL Read buffer T (2×) were added to each well and the plate read on a MSD Sector Imager 6000 (Meso Scale Diagnostics, USA).

1.7 Bioanalytical Method Validation Parameters

1.7.1 Reagent Optimisation

Chequer-board and time course assays were performed to optimise the reagent concentrations and incubation conditions. This included the optimisation of the concentrations of biotinylated TP (range 0.0313 to 2.00 μg/mL), sulfo-TAG TP (range 0.0313 to 2.00 μg/mL) and positive control antibody (range 0 to 20,000 ng/mL, see below).

1.7.2 Calibration Standard Curve

Sixteen concentrations of anti-TP antibodies diluted in assay buffer in the range of 0 to 20,000 ng/mL were assessed (n=2, in duplicate) to determine a calibration curve range.

1.7.3. Positive Control Standards Suitability

Using the optimal calibration range determined above, calibration standards were prepared in duplicate from anti-TP antibodies in pooled negative control sera and diluted with buffer at the determined minimal required dilution (MRD, see below). Twenty six positive control calibration curves were analysed for each species during validation. The cumulative accuracy (relative error, % RE) and precision (coefficient of variation, % CV) of the back-calculated concentrations from all validation batches calculated was used to access the appropriateness of the regression model for each species. The same fitting routine was then applied for all assay batches subsequently performed throughout the validation study.

1.7.4. MRD

Standard curves prepared in whole dog and mouse sera were diluted with assay buffer to give the following dilutions of sera: 1 in 100 (1%), 1 in 20 (5%), 1 in 10 (10%), 1 in 2 (50%) and neat (whole serum, 100%). Each calibration curve was analysed against a standard curve prepared in buffer (0% matrix). The MRD was identified as the dilution at which the signal of the individual samples is not significantly different to the buffer signal. The MRD was confirmed during the selectivity experiment, see below.

1.7.5. Selectivity

Selectivity was assessed to demonstrate that the target antibody is measured and that quantitation is not affected by the presence of the biological matrix, metabolites or co-administered drugs. For each species, 10 individual serum samples and the negative control serum were spiked with anti-TP antibodies at low (70 ng/mL) and high (7000 ng/mL) concentrations. Two aliquots of each spiked samples and the matched unspiked sample were prepared. Spiked and matched unspiked samples were incubated for one hour, one aliquot with buffer and one aliquot with free TP (0.125 μg/mL, taking into account the established MRD). Two assay runs were performed, each consisting of 5 samples and the negative control serum, which were either spiked or unspiked and pre-incubated with and without TP, plus a calibration curve.

The percentage inhibition of signal in the presence of free TP provided a preliminary indication of the confirmatory assay cut-point based on the variability of the inhibition of zero, low and high antibody concentrations. This was calculated as follows:

$$\text{Signal inhibition}(\%) = 100 \times [1 - (\text{drug inhibited sample}/\text{uninhibited sample})]$$

1.7.6 Assay Cut-Point and Sensitivity

The cut-point of an assay is the level of response of the assay at or above which the sample is defined to be positive and below which it is defined to be negative. For each species, 15 individual blank serum samples were analysed together with negative control serum which was either unspiked and spiked with low (106 ng/mL), middle (1000 ng/mL) and high (7000 ng/mL) anti-TP antibody concentrations and were pre-incubated in the absence and presence of free TP (0.125 µg/mL), on three separate occasions (n=1 in duplicate) and performed by two analysts.

The assay cut-point data was assessed to determine if a floating cut-point or a fixed cut point was appropriate for the assay methodology used. The screening cut point was calculated using the approach described by Shankar et al. (2008). For each species the data from 15 samples was assessed for normality using the Shapiro-Wilk test (Shapiro and Wilk, 1965). If data was non-normally distributed either log or square root transformations were applied. An assessment for outliers was made by considering the Studentized Deleted Residuals; residuals greater than ±3 standard deviations (SD) were excluded. Once outliers were removed, data was reassessed for normality using the Shapiro-Wilk test; depending on the outcome, the validation cut-point (VCP) was either defined as the 95% Quantile for non-normally distributed data, or the mean+1.645* SD for normally distributed data. The Correction Factor (CF) was defined as either VCP minus the negative control mean, or VCP minus the negative control medium, depending on whether normality was assumed or not. The screening cut-point (SCP) was defined as either the VCP or the negative control+CF, depending on whether the means and variances between runs were similar.

1.7.7. Precision, Accuracy and Assay Drift

Intra-assay precision (variability between replicates of the same sample in an assay) and QC baseline concentrations were determined from replicate analysis of validation QC samples at three concentrations relative to the cut-point low (just above), mid (mid assay dynamic range) and high (high assay dynamic range). The negative control sera samples were used as the negative control QC samples. All were analysed in one run (n=3 in duplicate) concurrently with the positive control standards.

Inter-assay precision (variability over multiple days) and assay plate drift was determined by analysing low, mid, and high validation QC samples assayed on three separate occasions days for the dog and four separate days occasions for the mouse (n=1 in duplicate) with one set of QC samples being analysed directly after the positive control standards and an additional set of QC samples in the last columns of the assay plate. Buffer was added to wells not containing positive control standards or validation QC sample.

Acceptance criteria of the QC samples was based on the following: the Low QC samples must be above the cut-point, the Mid QC sample must be in the middle of the dynamic range (above the Low QC level but below the High QC level) and High QC sample must be at the high end of the dynamic range.

Intra-assay precision was considered acceptable where the mean instrument response (IR) reading and concentration at each QC level were observed within ±20%. Inter-batch accuracy of the mean instrument response and concentration at each level should be within ±20%, of the baseline as determined from the intra-assay QC analysis.

Assay drift was assumed negligible if the IR reading and/or concentrations of the validation QC samples (if appropriate) at the beginning and end of the assay plate were within ±20%, calculated as follows:

Percent difference=100×Front QC IR−Back QC IR/Average of (Front QC IR+Back QC IR)

1.7.8 Stability

The stability of anti-TP antibodies in mouse and dog sera at room temperature and after three freeze-thaw cycles was assessed by the analysis of QC samples at low, middle and high concentrations against freshly prepared positive control standards. For short-term ambient temperature stability, aliquots of each QC were thawed at room temperature for two hours (the expected maximum duration test samples will thawed prior to analysis) before analysis (n=3 in duplicate). For short-term ambient temperature stability of diluted samples, aliquots of each QC were thawed at room temperature, diluted with buffer to the MRD and stored at room temperature for 1 hour (the expected time test samples will be pre-incubated with TP before analysis (n=3 in duplicate) in one assay.

For assessment of the effect of repeated freeze-thaw cycles on the stability of anti-TP antibodies in the biological matrix, three aliquots of each QC concentration (stored at −70° C.) were thawed, unassisted for 2 hours at room temperature. The aliquots were then refrozen for at least 12 hours. On the second day, the samples were removed together with an additional set of frozen QC samples (3 aliquots at each QC concentration) and the thawing-freezing process repeated. On the third day both sets of QC samples were removed together with an additional set of frozen QC samples and then thawed. All three sets of QC samples were then analysed to determine stability after one, two and three cycles (n=3 in duplicate) in one assay.

Stability was verified if the stability analysis meet the criteria of the mean precision (% CV) and the mean RE (%) were within ±20% of the baseline concentrations.

1.7.9 Robustness

Assay robustness was assessed by evaluating small and deliberate perturbations of the assay conditions; the concentrations of validation QC samples at low, middle and high concentrations were analysed with extended incubation timings in one run (n=1 in duplicate) concurrently with positive control standards; the assay time was extended to an additional 15 minutes per hour at each incubation stage. The assay is considered as robust where the final accuracy criteria within ±20% were observed for the incubation timings tested.

1.7.10. Prozone

Assay prozone (hook effects) caused by high anti-TP antibody levels was investigated by serial dilution of a high spiked sample (containing anti-TP antibodies at a concentration 3.5 fold greater than the top standard) with negative control serum. Prozone effects were considered as not present provided the sample values remained above the top positive control standard.

1.8 Data Handling and Statistics

All data acquisition and evaluation were performed using the software package Watson LIMS (Laboratory Information Management System) version 7.2 (Thermo Electron Corporation, UK). All statistics (mean, standard deviation (SD), CV (%) and RE (%) presented are based upon reported numbers from the original database. Data handling for cut point calculation was analysed using SAS 9.1.3 (SAS Institute Inc., 2002).

Results 2.1 Calibration Range and Positive Control Standard Curves

Figure 14:
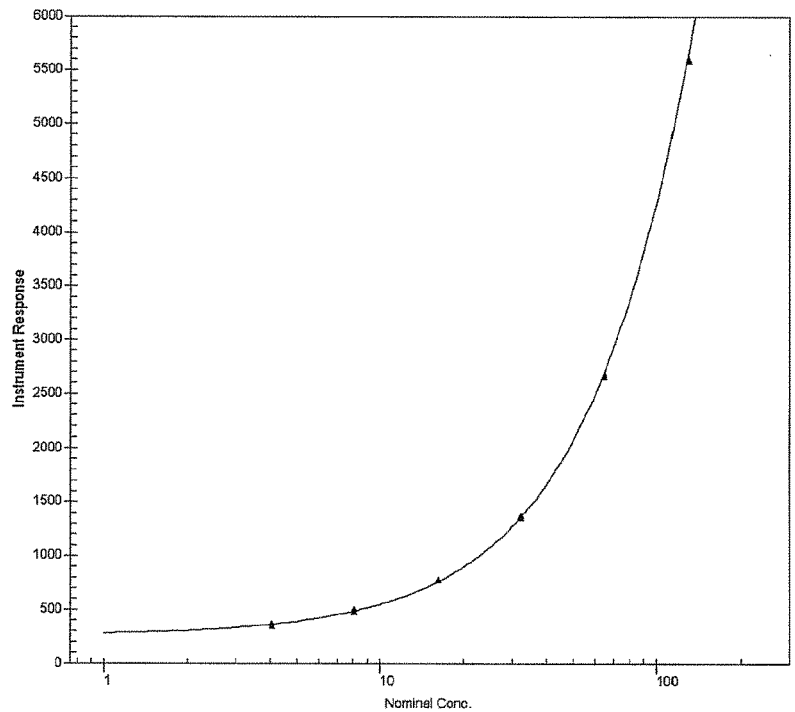
FIG. 14 shows representative positive control curves of instrument response versus concentration of anti-TP antibody in mouse negative serum (A) and dog negative serum (B). Calibration standards for anti-thymidine phosphorylase antibodies (ng/ml). Regression method=5PL (auto estimate)–weighting factor=1/F2. Response=(min-max)/+ (conc/c)slope)**M)+max. Min for (A)=261.6800814. Max for (A)=1020084.70. Slope for (A)=1.14791854. C for (A)=13980.6138. M for (A)=1.14834934. R-squared for (A)=0.9986. Min for (B)=239.881720. Max for (B)=53269.6211. Slope for (B)=1.20789355. C for (B)=10119.0648. M for (B)=17.0358819. R-squared for (B)=0.9991.
Figure 14:
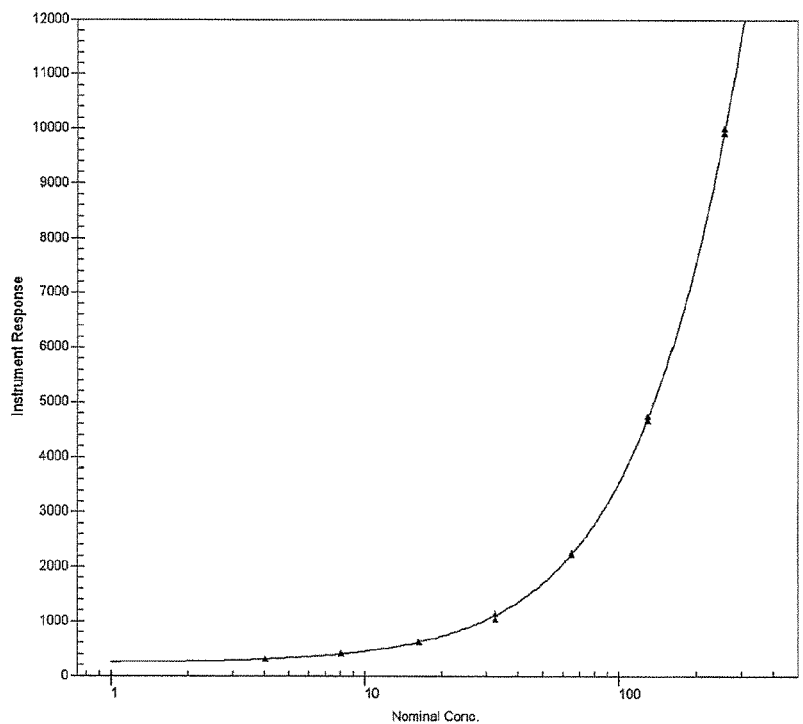

The optimal assay concentrations of biotinylated TP and sulfo-TAG were 0.0625 µg/mL and 0.0313 µg/mL, respectively (data not shown). Following an analysis of the data obtained from the extended concentration range, the calibration range was refined to 8 concentrations over the range 2.50 ng/mL to 7,500 ng/mL for both species, see FIG. 14 for representative positive control standard curves. Raw data was processed in Watson LMS version 7.2, using a 5-parameter logistical (auto estimate, 5PL) algorithm with a weighing factor of 1/F². Calibration curves fitted to the 5PL regression method showed correlation coefficients >0.998 for both species. A summary of the inter-assay cumulative accuracy (% RE) and precision (% CV) of the back calculated concentrations of the calibration standards are shown for both species in Table 4. The cumulative accuracy (% RE) and precision (% CV) of the back calculated values were within 20% of the nominal concentration within the range of 25 ng to 7,500 ng for both species, with 25 ng being the lower limit of quantification (LLOQ) and 7,500 ng as the upper limit of quantification (ULOQ).

2.2 MRD and Selectivity

Figure 15:
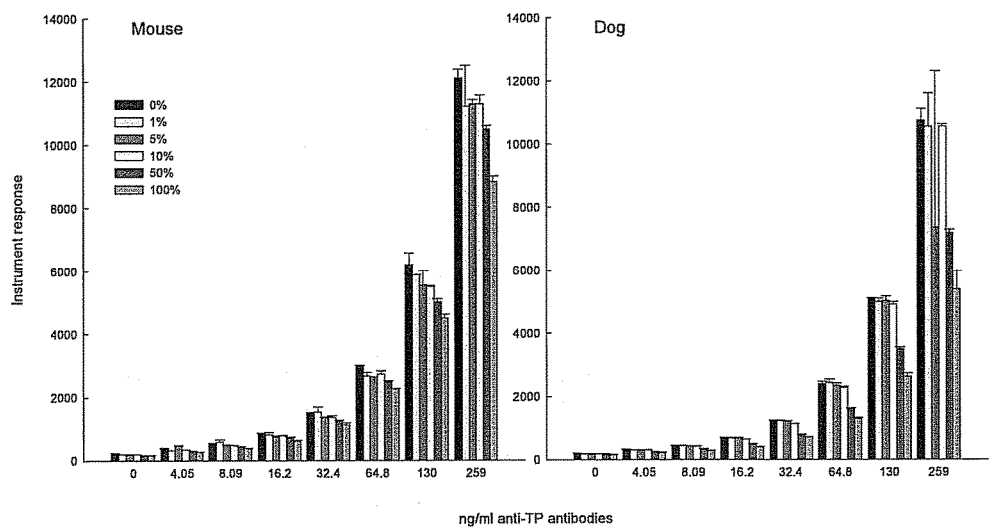
FIG. 15 shows instrument response versus concentration of anti-TP antibodies constructed in different dilutions of mouse (left plot) and dog right plot) sera. Each calibration curve was analysed against a standard curve prepared in buffer (0% matrix).

A minimal serum dilution of 1 in 10 for both species was required in all samples prior to analysis as there were no significant differences observed between the buffer (0% matrix) and serum standard curves at this dilution (FIG. 15).

The mean recoveries for anti-TP antibodies spiked into mouse serum at 70 ng/mL and 7,000 ng/mL were 117.9% and 93.2% respectively, and the variability in recovery amongst individual samples, as determined by the CV were 10.7% and 5.5%, respectively. The mean inhibition for anti-TP antibodies spiked into mouse serum at 70 ng/mL and 7000 ng/mL and pre-incubated with TP against spiked samples pre-incubated in assay buffer were 52.0% and 96.2% respectively. The variability in recovery amongst individual samples, as determined by CV were 9.0% and 0.4% for spikes of 70 ng and 7000 ng, respectively (Table 5).

The effect of serum variability, using batches from ten different animals, from both species, on the reliability of the method was therefore shown to be negligible.

2.3 Assay Cut-Point and Sensitivity

To establish the threshold for a positive result, the signal distribution for individual blank serum samples was determined for both species. The Shapiro-Wilk test was significant for mouse sample data, and was still significant following log and square root transformation. Following an assessment of the untransformed data, mouse serum sample 15 was excluded as the studentised residual was greater than +3. The Shapiro-Wilk test was reapplied and was still significant with no transformation and following log and square root transformation. Hence a non-parametric approach was applied.

Following an assessment of the untransformed data using a box plot, mouse sera samples 14 and 15 were deemed outliers and excluded. The validation cut point for the screening matrices data of the assay was calculated as 412.17 (the 95$^{th}$ percentile of the transformed data for all the results). The low QC concentration was calculated as the mean concentration of cut-point+(2.33×SD)=210.0 ng/mL.

There was evidence of statistically significant differences between the means for plate and day effects (p<0.001), but not for analyst (p=0.368) and therefore a floating screening cut point was required. The correction factor for the screening cut point was estimated to be 201.67 and this was applied to subsequent assays.

The Shapiro-Wilk test was not significant for the dog sample data. Following an assessment of the untransformed data, dog serum sample 1 was excluded as the studentised residual was greater than +3. Once the outlier was excluded, the Shapiro-Wilk test was re-applied and was not significant. The validation cut-point for the screening matrices data of the assay was calculated as 263.64. The low QC concentration was calculated as the mean concentration of cut-point+ (2.33×SD)=44.4 ng/mL.

There was evidence of statistically significant differences between the means for plate and day effects (p<0.001) but not analyst (p=0.247). There was also evidence that the variances were different between groups (p=0.002 Levene's test) and hence a dynamic cut point was required. As Levene's test was significant, each analyst was analysed separately.

For Analyst 1 there was evidence of statistically significance differences between the means for day and plate effects (p≤0.002). There was also evidence that the variances were different between groups (p=0.006 Levene's test) and hence a dynamic cut point was required for Analyst 1. No further calculations were performed for this analyst as they were not required for future studies.

For Analyst 2, there was evidence of statistically significant differences between the means for day and plate effects (p<0.001). There was no evidence that the variances were different between groups (p=0.188 Levene's test) and hence a floating cut point was required for this analyst. The correction factor for the screening cut point was estimated to be 70.38 and this was applied to subsequent assays.

For calculations of screening cut points, visual inspections of the mouse and dog data revealed normal distributions. Following assessments of the transformed data, dog serum sample 11 (analyst 2, plate 1 on day 3) was excluded as the studentised residual was less than −3, and dog serum sample 1 (analyst 1, plate 2 on day 3) was excluded as the studentised residual was greater than +3. None of the mouse data were excluded. There was no evidence of statistically significant differences between the means for the analysts, plates or days effects for both the mouse and dog assays. The fixed specificity cut points were calculated to be 37.12% and 31.41% inhibition in the mouse and dog sera, respectively.

2.4 Precision and Accuracy

Precision of the bioanalytical methods were evaluated by determining the CV of the measured concentrations of anti-TP antibodies following the analysis of validation QC samples. The primary positive control standard stock (0.518 mg/mL) was diluted 1 in 74 with negative control serum (mouse or dog, as appropriate) to form the high QC sample (7000 ng/mL). The mid QC sample (1000 ng/mL) was formed by dilution of the high QC sample with the appropriate negative control serum. The low QC sample (concentrations of 210 ng/mL for mouse and 44.4 ng/mL for dog) was formed by dilution of the mid QC sample with the appropriate negative control serum.

Intra-assay concentration precisions for each species are shown in Table 6. The mean imprecision measurements, as indicated by the CVs, ranged from 1.1% to 8.0% for mouse serum matrix and 1.9% to 2.5% for dog serum matrix.

Inter-assay precision for concentrations are shown in Table 7 for both species. The mean imprecision measurements, as indicated by the CVs, were all within ±20%, and the mean accuracy measurements, as indicated by the RE, ranged between −1.6% to 6.7% for mouse serum matrix and −13.0% to −2.5% for dog serum matrix.

2.5 Assay Drift

Assay drift was not observed for either species. The mean difference in instrument response readings and/or concentrations of the validation QC samples at the beginning and end of the assay plate were within ±20%, when compared to each other (data not shown).

2.6 Stability

Anti-TP antibodies were stable in both mouse and dog sera at ambient room temperature (ca 22° C.) for 2 hours, diluted in buffer at ambient room temperature for 1 hour (Table 7), and following 3 freeze/thaw cycles (Table 8).

2.7 Robustness

The intra-assay accuracy results from the robustness assay were within the acceptance criteria after the assay time was extended to an additional 15 minutes per hour at each incubation stage. The results were also in good agreement with the inter-assay measurements from assays performed without the extended incubation timings. The mean observed concentration values for the validation QC samples expressed as mean RE ranged between −8.7% and 5.1%. Increasing the incubation times by 15 minutes therefore had no marked effect on the assay performance and robustness is verified for the incubation timings tested (Table 9).

2.8 Prozone

For both dog and mouse sera matrices, prozone was not observed in the assay up to a whole serum anti-TP antibody concentration of 25,900 ng/mL some 3.5-fold higher than the highest positive concentration standard (data not shown).

Discussion

The focus of this study was to describe the development and validation of an ECL bridging immunoassay method for the measurement of anti-TP antibodies in dog and mouse sera. An ECL bridging immunoassay format was selected due to the advantages of not being species specific and having the potential to detect all antibody isotypes and classes produced in an immune response. The analytical procedures were developed in line with current recommendations for the design and optimization of immunoassays used in the detection of host antibodies against therapeutic proteins and biotechnology products. Positive control standard suitability, assay cut-point and sensitivity, selectivity and MRD, intra and inter-assay precision and accuracy, robustness, prozone and stability were all investigated. The results demonstrate the assay to be highly accurate, precise, sensitive and robust for the quantification of anti-TP antibodies in mouse and dog sera.

TABLE 4

Summary of accuracy and precision for back-calculated values of positive control standards in negative mouse and dog sera (inter-assay)

| Species | Concentration (ng/ml) | | | | | | | |
|---|---|---|---|---|---|---|---|---|
| | 2.50 | 7.50 | 25.0 | 75.0 | 250 | 750 | 2500 | 7500 |
| Mouse | | | | | | | | |
| Mean | 5.15 | 7.22 | 26.0 | 77.1 | 252 | 726 | 2540 | 7480 |
| SD | 4.25 | 3.0 | 4.3 | 5.4 | 11 | 18 | 80 | 230 |
| CV (%) | 82.4 | 41.6 | 16.5 | 7.0 | 4.5 | 2.5 | 3.2 | 3.0 |
| RE (%) | 106.1 | −3.7 | 3.8 | 2.9 | 0.7 | −3.2 | 1.7 | −0.3 |
| n | 29 | 47 | 49 | 50 | 50 | 50 | 50 | 50 |
| Dog | | | | | | | | |
| Mean | 2.59 | 7.55 | 26.4 | 77.2 | 249 | 733 | 2520 | 7510 |
| SD | 1.57 | 2.66 | 1.7 | 3.4 | 7 | 16 | 70 | 200 |
| CV (%) | 60.4 | 35.2 | 6.3 | 4.4 | 2.6 | 2.1 | 2.7 | 2.6 |
| RE (%) | 3.8 | 0.7 | 5.5 | 3.0 | −0.3 | −2.2 | 0.9 | 0.1 |
| n | 24 | 48 | 52 | 52 | 52 | 52 | 52 | 52 |

TABLE 5

Spike recovery after pre-incubation in the absence and presence of free TP

| Species | Spike (ng/ml) | Response in spiked sample (ng/ml) Mean ± SD* | Recovery (%) Mean ± SD* CV | Response in spiked sample incubated with TP (ng/ml) Mean ± SD* | Inhibition (%) Mean ± SD* CV |
|---|---|---|---|---|---|
| Mouse | 70 | 105.6 ± 35.4 | 117.9 ± 12.7 10.7 | 367.7 ± 98.5 | 52.0 ± 4.7 9.0 |
| | 7000 | 6545.8 ± 356.3 | 93.2 ± 5.1 5.5 | 1477.2 ± 262.7 | 96.2 ± 0.4 0.4 |
| Dog | 70 | 87.9 ± 14.5 | 112.0 ± 15.9 14.2 | 207.7 ± 12.2 | 46.7 ± 3.9 8.4 |
| | 7000 | 7310.0 ± 1011.0 | 104.3 ± 14.4 13.8 | 900.8 ± 109.3 | 96.1 ± 0.2 0.2 |

*n = 12

TABLE 6

Assay precision and accuracy

| Species | Concentration (ng/ml) | Intra-assay Mean ± SD* (ng/ml) | Intra-assay CV (%) | Inter-assay Mean ± SD* (ng/ml) | Inter-assay CV (%) RE (%) |
|---|---|---|---|---|---|
| Mouse | Low QC 210 | 235 ± 3 | 1.1 | 224 ± 19 | 8.4 6.7 |
| | Middle QC 1000 | 1133 ± 91 | 8.0 | 1060 ± 90 | 8.6 6.1 |
| | High QC 7000 | 7710 ± 96 | 1.3 | 6890 ± 360 | 5.2 −1.6 |
| Dog | Low QC 44.4 | 43.1 ± 1.0 | 2.3 | 43.3 ± 5.2 | 12.1 −2.5 |
| | Middle QC 1000 | 871 ± 22 | 2.5 | 870 ± 70 | 8.0 −13.0 |
| | High QC 7000 | 6520 ± 125 | 1.9 | 6660 ± 480 | 7.3 −4.8 |

*n = 3

TABLE 7

Stability of anti-TP antibodies at three concentrations in neat and diluted mouse and dog sera at room temperature

| Species | QC sample (ng/ml) | 0 hours serum | 2 hours serum | 1 hour diluted |
|---|---|---|---|---|
| | | Mean ± SD Concentration (ng/ml)* CV (%) RE (%) | | |
| Mouse | Low QC 210 | 235 ± 3 1.1 11.7 | 249 ± 5 2.1 18.6 | 260 ± 22 8.4 23.8 |
| | Middle QC 1000 | 1130 ± 90 8.0 13.3 | 1100 ± 60 5.0 9.7 | 1200 ± 20 1.7 20.0 |
| | High QC 7000 | 7710 ± 100 1.3 10.1 | 8080 ± 310 3.9 15.5 | 8590 ± 160 1.9 22.8 |
| Dog | Low QC 44.4 | 43.1 ± 1.0 2.3 −2.9 | 43.0 ± 2.2 5.0 −3.2 | 40.0 ± 2.2 5.4 −9.9 |
| | Middle QC 1000 | 871 ± 22 2.5 −12.9 | 8.55 ± 11 1.3 −14.5 | 876 ± 30 3.4 −12.4 |

TABLE 7-continued

Stability of anti-TP antibodies at three concentrations in
neat and diluted mouse and dog sera at room temperature

| Species | QC sample (ng/ml) | 0 hours serum | 2 hours serum | 1 hour diluted |
|---|---|---|---|---|
| | | Mean ± SD Concentration (ng/ml)* CV (%) RE (%) | | |
| | High QC 7000 | 6520 ± 130 1.9 −6.8 | 6630 ± 150 2.3 −6.7 | 6540 ± 90 1.4 −6.6 |

*n = 3

TABLE 8

Stability of anti-TP antibody at three concentrations
in mouse and dog sera after repeated freeze-thaw cycles

| Species | QC sample (ng/ml) | 1 freeze-thaw cycle | 2 freeze-thaw cycles | 3 freeze-thaw cycles |
|---|---|---|---|---|
| | | Mean ± SD Concentration (ng/ml)* CV (%) RE (%) | | |
| Mouse | Low QC 210 | 240 ± 6 2.4 16.0 | 240 ± 4 1.5 14.1 | 230 ± 25 10.8 9.4 |
| | Middle QC 1000 | 1020 ± 130 12.5 2.2 | 1010 ± 20 1.5 1.3 | 1050 ± 20 1.6 5.0 |
| | High QC 7000 | 7520 ± 390 5.2 7.4 | 7770 ± 90 1.1 11.0 | 7940 ± 70 0.9 13.5 |
| Dog | Low QC 44.4 | 43.1 ± 1.0 2.3 −2.9 | 43.0 ± 2.2 5.0 −3.2 | 40.0 ± 2.2 5.4 −9.9 |
| | Middle QC 1000 | 871 ± 22 2.5 −12.9 | 8.55 ± 11 1.3 −14.5 | 876 ± 30 3.4 −12.4 |
| | High QC 7000 | 6520 ± 130 1.9 −6.8 | 6630 ± 150 2.3 −6.7 | 6540 ± 90 1.4 −6.6 |

*n = 3

TABLE 9

Robustness of assay

| Species | QC sample (ng/ml) | Front QC (mean)* | Drift QC (mean)* | Mean ± SD* CV (%) RE (%) |
|---|---|---|---|---|
| Mouse | Low QC 210 | 231 | 205 | 218 ± 18 8.4 3.8 |
| | Middle QC 1000 | 1040 | 1010 | 1025 ± 21 2.1 2.5 |
| | High QC 7000 | 6380 | 6510 | 6445 ± 92 1.4 −7.9 |

TABLE 9-continued

Robustness of assay

| Species | QC sample (ng/ml) | Front QC (mean)* | Drift QC (mean)* | Mean ± SD* CV (%) RE (%) |
|---|---|---|---|---|
| Dog | Low QC 44.4 | 45.7 | 47.6 | 46.7 ± 1.3 2.9 5.1 |
| | Middle QC 1000 | 909 | 917 | 913 ± 6 0.6 −8.7 |
| | High QC 7000 | 6820 | 6740 | 6780 ± 57 0.8 −3.1 |

*n = 2

Example 5—Preclinical Toxicity Evaluation of Erythrocyte-Encapsulated Thymidine Phosphorlyase in BALB/c Mice and Beagle Dogs The objective of the studies reported here was to evaluate the systemic toxic potential of EE-TP in BALB/c mice and Beagle dogs in support of clinical development of EE-TP. The mouse and dog were chosen as the first and second test species respectively because of their acceptance as predictors of toxic change in man and the requirement for a rodent and non-rodent species by regulatory agencies. The BALB/c mouse was used because of previous experience with administration of EE-TP to that strain. The Beagle strain was employed because of the historical control data available and also because the dog also has a sufficient volume of blood to allow the formulation of EE-TP using autologous blood (Chalmers, 1985; Sprandel et al., 1981). The studies were designed to meet the requirements of regulatory guidelines and were conducted in accordance with the requirements of current, internationally recognised Good Laboratory Practice Standards.

A standard toxicological evaluation was performed which included daily clinical signs, weekly body weight and food consumption, and end of study ophthalmic examinations, clinical pathology, organ weights, and complete gross necropsy on all animals and light microscopic examination of a range of tissues.

Materials and Method 1.1 Test and Control Materials

Recombinant *E. coli* thymidine phosphorylase was manufactured for this study by Sigma-Aldrich (Israel) and was supplied formulated in a potassium dihydrogen orthophosphate stabilization buffer with a specific activity of 178 to 211 IU/mg protein. The Master and working cell bank is stored in the Jerusalem Plasmid Bank. The specification and batch analysis release results for the recombinant enzyme employed in these studies are outlined in Table 10. The test material, EE-TP was formulated by encapsulation within dog or mouse erythrocytes as follows:

The dog study followed the proposed clinical regime, in that autologous blood was removed from a subject for processing into test or control material and then administered back to the same subject; one day before each dosing occasion, 50 ml of blood was collected via a suitable vein from the appropriate dog into vacutainers with lithium heparin anticoagulant and transported to St. George's, University of London. EE-TP was formulated by encapsulation of thymidine phosphorylase within erythrocytes using our established reversible hypo-osmotic dialysis process (Chalmers, 1985; Bax et al., 1999). Aseptic techniques and sterile materials were used throughout. Briefly, blood was centrifuged at 1,100×g for 10 minutes, and the plasma and buffy coat removed and retained for later use. Erythrocytes were washed twice in cold (4° C.) phosphate buffered saline (PBS; 2.68 mM KCl, 1.47 mM KH2PO4, 136.89 mM NaCl, 8.10 mM Na2HPO4, pH 7.4) The washed and packed erythrocytes were then mixed with cold PBS containing 200 IU/ml of thymidine phosphorylase to form a suspension with a haematocrit of 70%. The cell suspension was placed in a dialysis bag with a molecular weight cut-off of 12,000 Da and then dialysed against 40 volumes of hypo-osmotic buffer (5 mM KH2PO4, 5 mM K2HPO4, pH 7.4) at 4° C. with rotation at 8 rpm for 90 minutes. The lysed erythrocytes were resealed by dialysis against 40 volumes of PBS supplemented with 5 mM MgCl2, 5 mM adenosine, and 5 mM glucose (SPBS, pH 7.4) at 37° C. with rotation at 8 rpm for 60 minutes. The enzyme-loaded erythrocytes were then washed three times in SPBS, with centrifugation at 100×g for 20 minutes. The cells displayed normocytic and normochromic morphology and were characterized for the following parameters: mean cell volume (MCV), mean corpuscular haemoglobin (MCH), mean corpuscular haemoglobin concentration (MCHC), extracellular haemoglobin concentration (Hb), encapsulated and extracellular thymidine phosphorylase activity (Table 11). The haematological parameters MCV, MCH and MCHC were determined using a Woodley MS4-5 haematology analyser. For the determination of extracellular Hb concentration and thymidine phosphorylase activity, extracellular fractions were obtained by adjusting the haematocrit of the washed and packed cells to 50% with PBS, followed by centrifugation at 1000×g for 10 minutes. Hb was measured by spectrophotometry at 542 nm using Drabkin's Reagent (Sigma-Aldrich, United Kingdom) and thymidine phosphorylase activity was determined as described below. The control material (sham-loaded erythrocytes) was formulated by subjecting erythrocytes to the same reversible hypo-osmotic dialysis process, but in the absence of thymidine phosphorylase. Cell recovery for EE-TP and sham-loaded cells was 62±1.2% and 59.2±1.3%, respectively. Plasma and white cells retained from the first centrifugation step and erythrocytes excess to requirements of the encapsulation procedure were added back to the test or control material to provide an infusion volume of 43-50 ml. This step was included to mimic the regime used in the clinical setting to avoid depletion of important blood constituents and maintain blood volume.

In the mouse study, to avoid complications of oversampling, allogeneic blood (rather than autologous blood) obtained from donor mice from the same strain was used to prepare the test and control material. A pre-determined volume of allogeneic blood in lithium heparin was supplied one day before dosing and processed into test and control material. The same reversible hypo-osmotic dialysis technique as described for the dog erythrocytes was used, except that all washes (both pre and post dialysis) and iso-osmotic resealing were performed using SPBS containing 3 mM glutathione, and the hypo-osmotic and iso-osmotic dialysis steps were conducted against 30 volumes of buffer (Murray et al., 2006). Cell recoveries were 36.7±1.8 (n=12) and 37.8±2.1% (n=9) respectively, for EE-TP and sham-loaded cells. The cells displayed normocytic and normochromic morphology and had the characteristics described in Table 11. After formulation, two volumes of test or control material were suspended in 1 volume of retained plasma.

For both species, within one hour of formulation, the test and control materials were dispatched at ambient temperature to Huntingdon Life Sciences for administration.

The stability of encapsulated thymidine phosphorylase activity was assessed over the proposed maximum time delay between formulation and infusion in the pre-clinical setting by analysis of thymidine phosphorylase activity after 0, 1, 4, 17 and 24 hours of storage at 4° C. and 22° C. One hundred μl aliquots of EE-TP prepared from dog and mouse erythrocytes were stored in closed microtubes at the appropriate temperature and then frozen after the appropriate incubation time until analysis.

1.2 Thymidine Phosphorylase Analysis

Thymidine phosphorylase activity was determined by quantification of the rate of thymine formation using a validated high performance liquid chromatography (HPLC) method (manuscript in preparation). The method is linear over a thymine concentration of 5 to 500 nmol/ml, and has a limit of detection and limit of quantification of 0.60 nmol/ml and 1.80 nmol/ml, respectively. Analyses were performed to verify the activity of cellular and extracellular thymidine phosphorylase activity in EE-TP and to confirm the absence of enzyme activity in the control material. Lysed (thawed from −80° C.) erythrocytes and extracellular fractions were diluted 1:1420 and 1:10, respectively with TRIS buffer (125 mM, pH 7.4). Twenty five μl of the diluted erythrocyte lysate or extracellular fraction was then added to 100 μl phosphate buffer (100 mM, pH 6.5) and 25 μl thymidine standard (10 mM), mixed and incubated at 37° C. for 10 minutes. The reaction was terminated with 25 μl 40% trichloroacetic acid (TCA). Samples were centrifuged at 12,000 rpm for 2 minutes and the supernatant washed twice with water-saturated di-ethyl ether for 2 minutes on a shaker to remove TCA. A sample volume of 10 μl was injected into the HPLC. A pre-packed Spherisorb 5 ODS column (125× 4.6 mm i.d.) was used in an isocratic system at a flow rate of 1.0 ml/min with a run time of 8 minutes. The buffer consisted of ammonium acetate (40 mM) with the ion-pairing agent tetrabutylammonium sulphate (5 mM), adjusted to pH 2.70 with HCl. The HPLC trace was recorded at 254 nm and 0.1 AUFS. Metabolites were identified by comparing spectra with pure standards.

1.3 Animal Husbandry

This aspect of the studies was performed at Huntingdon Life Sciences, UK. All in-life experimental procedures were performed in compliance with the Animals (Scientific Procedures) Act 1986. Animal housing complied with the United Kingdom Home Office Code of Practice for the Housing and Care of Animals used on Scientific Procedures. The study designs were reviewed and approved by the holders of the Home Office Project Licenses at Huntingdon Life Sciences.

Mice.

BALB/c mice were purchased from a commercial breeder and were acclimatized for 18 days. At the start of treatment the mice were 10 weeks old, with bodyweights of 21.5 to 26.7 g for males, and 18.7 to 22.6 g for females. The animals were housed up to three per cage for females and singularly for males. The temperature and relative humidity were maintained within the range of 19 to 23° C. and 40 to 70%, respectively. Artificial lighting was controlled to give a 12 hour light/dark cycle. Food (Rat and Mouse No. 1 Maintenance Diet) and water were given ad libitium.

Dogs.

Pure-bred Beagle dogs of known lineage were obtained from a commercial breeder and were inoculated against canine distemper virus, canine hepatistis virus, canine parainfluenza virus, canine parvovirus, *Leptospira canicola*, *Leptospira icterohaemorrhagiae* (by subcutaneous injection of DHPPi and *Leptospira*) and *Bordetella bronchiseptica* vaccine (Intrac® given intranasally). On arrival, animals also received a veterinary examination and received a course of oral treatment with the anthelmintic 'Drontal Plus®' (praziquantel, pyrantel embonate and febantel. The dogs were allowed to acclimatise to housing conditions for at least four weeks before the start of treatment. At the start of treatment the dogs were approximately 24 to 27 weeks of age and weighed 9.6 to 11.8 kg for males and 7.07 to 10.0 kg for females. The animals were housed in trios of the same sex and dose group, except for the period immediately before each administration. Each individual pen was equipped with under-floor heating and graded whitewood sawdust was used as litter and changed daily. Room temperature was maintained in the range of 15 to 24° C. and air extraction was via a balanced system designed to provide approximately 12 air changes per hour. Lighting was controlled to give a 12 hour light/dark cycle. Each dog was offered 400 g of a standard dry pelleted diet (Teklad 2021 Dog Maintenance Diet) daily. Food was offered midmorning and each dog was allowed access to it for at least one hour, after which time any uneaten food was removed and subsequently weighed and discarded. Water was given ad libitium.

1.4 Administration of Test and Control Materials

For both species an intermittent intravenous bolus injection route of administration was chosen to simulate the conditions of clinical administration. The mice received an intravenous bolus injection at a volume-dose of 4 ml/kg/occasion, using a graduated syringe and needle inserted into the tail vein. In the dogs, venous access was gained via cephalic or saphenous veins, alternated at each administration. A catheter primed with a small volume of saline was then connected to a syringe driver (Harvard Apparatus PHD2000 infusion pump) and the entire volume of blood was administered back to the dog from which it came from at an infusion rate of 10 ml/minute (except for Group 3 males on Day 15, where an infusion rate of 5 ml/minute was used).

The study consisted of one control (Group 1) and two treated groups (Groups 2 and 3) for each species and which were treated as outlined in Table 12. Groups 1 and 3 were treated twice per week. Group 2 was treated once every two weeks, according to the proposed clinical regime, with a proposed maximal dose level of 200 IU/kg. The twice weekly administration to Group 3 was intended to achieve an exposure approximately four times higher than the proposed clinical dose to achieve a satisfactory safety margin for clinical trials.

1.5 Serial Observations

Animals were inspected visually at least twice daily for evidence of ill-health or reaction to treatment. On dosing days detailed observations were recorded at the following times in relation to dose administration: predose, immediately after infusion, between 0.5 and 2 hours after completion of dosing, and as late as possible in the working day. The bodyweight of each animal was recorded weekly (mouse) and twice per week (dog) during the acclimatization period, on the day treatment commenced (Day 1), twice weekly throughout the treatment period, and before necropsy. The weight of food supplied to each cage of mice and each individual dog, the weight that remained, and an estimate of any spilled was recorded during the acclimatization period and throughout the study. For the mouse, the weekly consumption per animal (g/animal/week) was calculated for each cage.

Ophthalmoscopic examinations were conducted predose and prior to each animals scheduled euthanization. Prior to each examination, the pupils of each animal were dilated using tropicamide ophthalmic solution (Mydriacyl). The adnexae, conjunctiva, cornea, sclera, anterior chamber, iris (pupil dilated), lens, vitreous and fundus were examined.

In the dog, electrocardiograph tracings were recorded from all animals on one occasion during the pretreatment period for the three standard limb leads (I, II, II) and the three augmented limb leads (aVR, aVL and aVF). Further tracings were obtained during Week 3, two and 24 hours after infusion for Group 2, and during Week 4, two and 24 hours after infusion for Groups 1 and 3. The traces were examined visually for any abnormalities of the electrical complexes and the heart rate was recorded.

1.6 Clinical Pathology

Clinical pathology samples were collected for the evaluation of haematology and clinical chemistry. In the dog these were obtained via the jugular vein before treatment commenced and during Week 4 before dosing. Additional samples were taken for haematology on Day 14 from all dogs, and on Day 21 from male dogs only. Mouse blood samples were taken at termination only; the animals were held under light general anaesthesia induced by isoflurane and blood samples were withdrawn from the retro-orbital sinus. Haematology parameters were measured in the first five mice per sex per group, and clinical chemistry parameters measured in the second five mice per sex per group.

Haematology parameters were analysed in blood collected into tubes containing EDTA as an anticoagulant using a Bayer Advia 120 haematology analyser and included: haematocrit (Hct), Hb, erythrocyte count (RBC), reticulocyte count, MCH, MCHC, MCV, total white cell count (WBC), differential WBC count (neutrophils, lymphocytes, eosinophils, basophils, monocytes, large unstained cells) and platelet count. In the mouse, bone marrow samples were obtained from the tibia and femur during necropsy for examination of bone marrow haematology. Prepared smears were air drier, fixed in methanol and stained using a romanowsky procedure.

Clinical chemistry parameters were examined in plasma (separated from blood which had been collected into lithium heparin) using a Roche PP Modular Analyser and included: alkaline phosphatase, alanine aminotransferase, aspartate aminotransferase, total bilirubin, urea, creatinine, glucose, total cholesterol, triglycerides, sodium, potassium, chloride, calcium, inorganic phosphorus, total protein and albumin. In the dog electrophoretic protein factions Albumin, α1 globulin, α2 globulin, β globulin, and γ globulin were processed using a Helena SPIFE 3000 with agarose gel and scanning with a densitometer. Albumin/globulin ratio was calculated from total protein concentration and analysed albumin concentration.

Coagulation parameters prothrombin time and activated partial thrombopastin time were measured for the dog in blood collected into citrate using an ACL 9000 Analyser.

Overnight urine produced was collected from all dogs before treatment commenced and during Week 4. Dogs were placed in individual metabolism cages without food or water and urine was collected for approximately 16.5 hours. Samples were examined for appearance, volume, pH, specific gravity, protein, glucose, ketones and bile pigments. A microscopic examination of the urine sediment was performed by centrifugation of an aliquot of urine and staining the resulting deposit with Kova stain before spreading on a microscope slide.

1.7 Anti-Thymidine Phosphorylase Antibodies

Blood samples for analysis of anti-thymidine phosphorylase antibodies were collected from all mice and dogs into standard serum tubes during pretreatment, on Day 17 (male dogs only) and at termination. After separation by centrifugation at 2000 g at 4° C. for 10 minutes the serum was collected into aliquots and frozen at −70° C. until analysis. Samples were analysed for anti-thymidine phosphorylase antibodies using validated GLP electrochemiluminescence detection methods (Example 4).

1.8 Necropsy and Histology

All animals were euthanized either 1 day (dogs) or 2 days (mice) following the administration of the last dose; mice were sacrificed by carbon dioxide asphyxiation, and dogs by an overdose of sodium pentobarbitone solution (200 mg/ml) by intravenous injection and subsequent exsanguination. A full macroscopic examination of the tissues was performed. Any abnormality in the appearance or size of any organ and tissue was recorded and the required tissue samples preserved in the appropriate fixative. Testes were fixed in modified Davidson's fluid and eyes were fixed in Davidson's fluid prior to transfer to 70% industrial methylated spirit. All other tissues were preserved in 10% neutral buffered formalin. Tissues to be examined were dehydrated, embedded in paraffin wax, sectioned at approximately 4 to 5 micron thickness and stained with haematoxylin and eosin. The following tissues were examined microscopically: adrenals, brain, femur with joint, heart, kidneys, liver, lungs, spinal cord, sternum, stomach, thyroid and uterus. For bilateral organs, sections of both organs were prepared. Findings were either reported as present or assigned a severity grade. In the latter case one of the following five grades was used—minimal, slight, moderate, marked or severe.

1.9 Statistical Analyses

Data are expressed as mean±SD or as mean±SEM. For the mouse studies, statistical analyses were carried out separately for males and females. Data relating to food consumption were analysed on a cage basis for females, and individually for males. For all other parameters, the analyses were carried out using the individual animal as the experimental unit. Comparisons were Group 1 versa 2, and Group 1 versa 3. The sequence of statistical tests employed for bodyweight, food consumption, organ weight and clinical pathology data was firstly a parametric analysis if Bartlett's test for variance homogeneity (Bartlett, 1937) was not significant at the 1% level; groups were compared using t-tests, and secondly a non-parametric analysis if Bartlett's test was still significant at the 1% level following both logarithmic and square-root transformations; groups were compared using Wilcoxon rank sum tests (Wilcoxon, 1945). For clinical pathology data, if 75% of the data (across all groups) were the same value, for example c, Fisher's Exact tests (Fisher, 1973) were performed. Treatment groups were compared using pairwise comparisons of each dose group against the control both for values <c versus values ≥c, and for values ≤c versus values >c, as applicable. For organ weight data, analysis of covariance was performed using terminal bodyweight as the covariate (Angervall and Carlstrom, 1963). The treatment comparisons were made on adjusted group means to allow for differences in bodyweight which might influence organ weight. Significant differences between control and treated groups are expressed as $*p<0.05$ and $**p<0.01$. Due to the small numbers on the dog study, statistical analyses were not performed.

Results 2.1 EE-TP Stability and Dose

Figure 16:
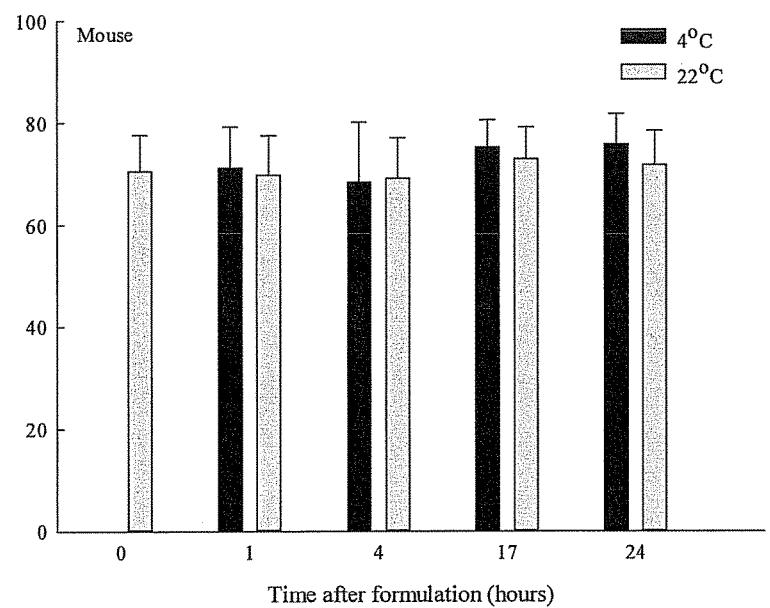
FIG. 16 shows thymidine phosphorylase activity encapsulated in (A) mouse and (B) dog erythrocytes as a function of storage time at 4 and 22° C. Results are expressed as mean±SEM of 4 experiments.

Storage of EE-TP for up to 24 hours at temperatures of 4° C. and 22° C. had no significant effect on erythrocyte associated thymidine phosphorylase activity (FIG. 16). Low concentrations of extracellular Hb and low extracellular activities of thymidine phosphorylase demonstrated that the EE-TP was stable 24 hours after formulation (Table 10). The maximum time delay between EE-TP formulation and infusion in these studies was 5 hours. Table 11 shows the doses administered.

2.2 Clinical Observations

Mouse. One male receiving EE-TP once every 2 weeks (Group 2) died immediately following the final dose on Day 29. The post mortem examination showed no gross findings, however, the histopathological examination revealed a marked presence of thrombi/emboli in the lungs and this was considered to be the reason for death. From Week 4 an ungroomed appearance was observed for the males in all groups (including control), accompanied by piloerection for both test substance treated groups. A hunched posture was noted for males receiving the twice weekly administration. Dark tails, dark patches on tails and/or scabbing were observed for all groups (including control) and were considered to reflect the intravenous route of administration.

There was no apparent effect of treatment on bodyweight, body weight gain or food consumption. Findings from the ophthalmoscopic examinations performed pretreatment and in Week 4 were within normal limits for animals of this age and strain. There was no evidence of a treatment-related effect on any ocular structures.

Dog. There were no unscheduled deaths during the study. Animals dosed once every two weeks (Group 2, dosed on Days 1, 15 and 29) showed no clinical signs on the first administration. However on the second administration (Day 15) transient post dose underactivity was noted in three males and two females. On the third administration (Day 29) transient post dose underactivity was noted for all three males and three females. On Day 29 additional transient clinical signs included: unusual respiration (panting) in one male and one female, loose or liquid faeces in one male and one female, and vomiting in one female. Pale gums were noted occasionally throughout the study for some animals.

Males dosed twice per week (Group 3, dosed on Days 1, 4, 8, 11, 15, 18, 22, 25 and 29) showed no clinical signs on dosing Days 1 and 4. From Day 5 onwards pale gums were noted for all males. However on Day 11 after dosing, one male vomited, a second dog was noted with loose faeces and the third dog was transiently underactive with loose faeces and vomiting. During dosing on Day 15 all three male dogs were underactive during dosing and this continued to be noted for one dog until the end of the working day. Loose faeces were noted for this dog during dosing, and body tremors and vomiting after dosing. As a result of these findings, a decision was made to pre-medicate the male dogs from Day 18 onwards with antihistamine, corticosteroid anti-inflammatory and anti-emetic treatments approximately one hour prior to dosing. As a result, the levels of clinical signs were significantly reduced at dosing Days 18, 22 and 25, with only post dose underactivity noted in two of the dogs. However, on Day 29 the level of underactivity increased for two dogs both during dosing and post dosing.

Females dosed twice per week (Group 3) showed the same range of clinical signs as those seen within the males but in general these signs appeared later in the study. On Day 15 one female was noted as unsteady at the end of dosing and on Day 18 another female was noted as underactive during dosing. Due to these finding both these females received predose medication in future treatments; despite this both animals were noted as underactive following dosing on Day 25, and one was again underactive on Day 29.

Pale gums were noted, but at a lower incidence than seen within the males of this group, but was also observed in one control dog.

There was a higher incidence of bruising and scabbing at the injection sites of males that had received twice weekly treatments in comparison with control. There were no apparent increases in incidence within the females or within dogs that were treated every two weeks.

Group mean bodyweight gain in males and females receiving twice weekly treatments (Group 3) was less than that of the control (Group 1). The mean bodyweight gain in females receiving treatment every second week (Group 2) was also lower than that of the controls (FIG. 17). However this result was due to one female, which was the smallest animal in the study. This difference from the control is therefore not considered to be related to treatment. There was no apparent effect of treatment on food consumption, ophthalmoscopic and electrocardiographic examinations.

2.3 Clinical Chemistry and Haematology

Mouse.

Table 12 shows the results of selected clinical chemistry parameters for mice after receiving treatment for 4 weeks. Higher than control concentrations of cholesterol (1.08-1.15 fold higher) and triglyceride (1.62-2.84 fold higher) were recorded for both male groups treated with EE-TP. In the absence of similar differences in the females or corroborative pathology, these higher concentrations were considered not to be of any toxicological importance. The plasma urea concentration was lower for females treated once every 2 weeks and both sexes treated twice per week compared to the control. This difference reflects the control group urea values being slightly higher than the expected background range (5-95 percentile: females 5.44 to 7.08 mM) and consequently is not considered to be related to EE-TP administration. All other inter-group differences after four weeks of treatment were minor or were confined to one sex and were attributed to normal biological variation. Such changes included the variations observed for creatinine and calcium in males and alkaline phosphatase in females.

No changes were observed in the haematological parameters investigated which were considered to be an effect of EE-TP administration. Anisocytosis was observed for the majority of animals (including control) and was more marked in the males. Higher than control mean corpuscular haemoglobin and mean corpuscular haemoglobin concentration were observed for both groups of treated females and a lower than control haematocrit was observed for females treated once every 2 weeks (Table 13). In the absence of a dose relationship or a similar finding in the males this difference from control was considered unlikely to be an effect of treatment. No abnormal microscopic findings were observed in the bone marrow.

Dog.

No treatment-related changes were observed in the clinical chemistry parameters investigated. All inter-group differences were minor and reflected trends that were present pretreatment or lacked dosage-relationship and are therefore attributed to normal biological variation. No changes were observed in the urinalysis parameters which were considered to be effect of treatment. Urinary chloride and sodium were increased for two males receiving twice weekly treatments when compared with control and pre-treatment values. However, no similar findings were noted in the females (Table 14).

Haematology investigations performed on Days 14 and 21 (males only) and in Week 4 revealed reductions in haematocrit, haemoglobin concentration and erythrocyte count, with an associated increase in reticulocytes within all groups including the controls, in comparison with pre-treatment. There was some variation in the magnitude of response between animals within the same treatment group, the magnitude of these changes were greater midway through the study (Day 14) and lessened, but still not returning to pre-treatment levels by the end of the study; animals treated once every two weeks were less affected than those treated twice weekly; females were less affected than males. All other inter-group differences were minor, reflected trends that were present pre-treatment or lacked dosage-relationship and were therefore attributed to normal biological variation (Table 15). A reduction in platelet count, when compared with the controls, was observed on Day 14 and/or Day 21 (males only) for males and females receiving treatments every two weeks and for males and females receiving twice weekly treatments. During Week 4 similar reductions were observed within these groups, however the magnitude of changes was less, and approximately half the animals treated once every two weeks and one of the animals treated twice per week returned to values similar to pre-treatment (Table 15).

2.4 Anti-Thymidine Phosphorylase Antibodies

Samples taken on Day 29 for all mice and dogs treated with EE-TP were positive for the presence of non-specific antibodies. A higher titre was noted for mice treated twice weekly (Group 3). No antibodies were detected in the control group animals. For the dog a confirmatory assay showed the presence of anti-thymidine phosphorylase-specific antibodies for one male receiving EE-TP once every two weeks (Group 2), and one male receiving EE-TP twice per week (Group 3). For the mouse the presence of anti-thymidine phosphorylase-specific antibodies was detected for 7 of 9 males and 7 of 10 females receiving EE-TP once every two weeks (Group 2) and 4 of 10 males and 1 of 10 females receiving EE-TP twice per week (Group 3).

2.5 Organ Weights and Anatomic Pathology

Mouse.

Figure 18:
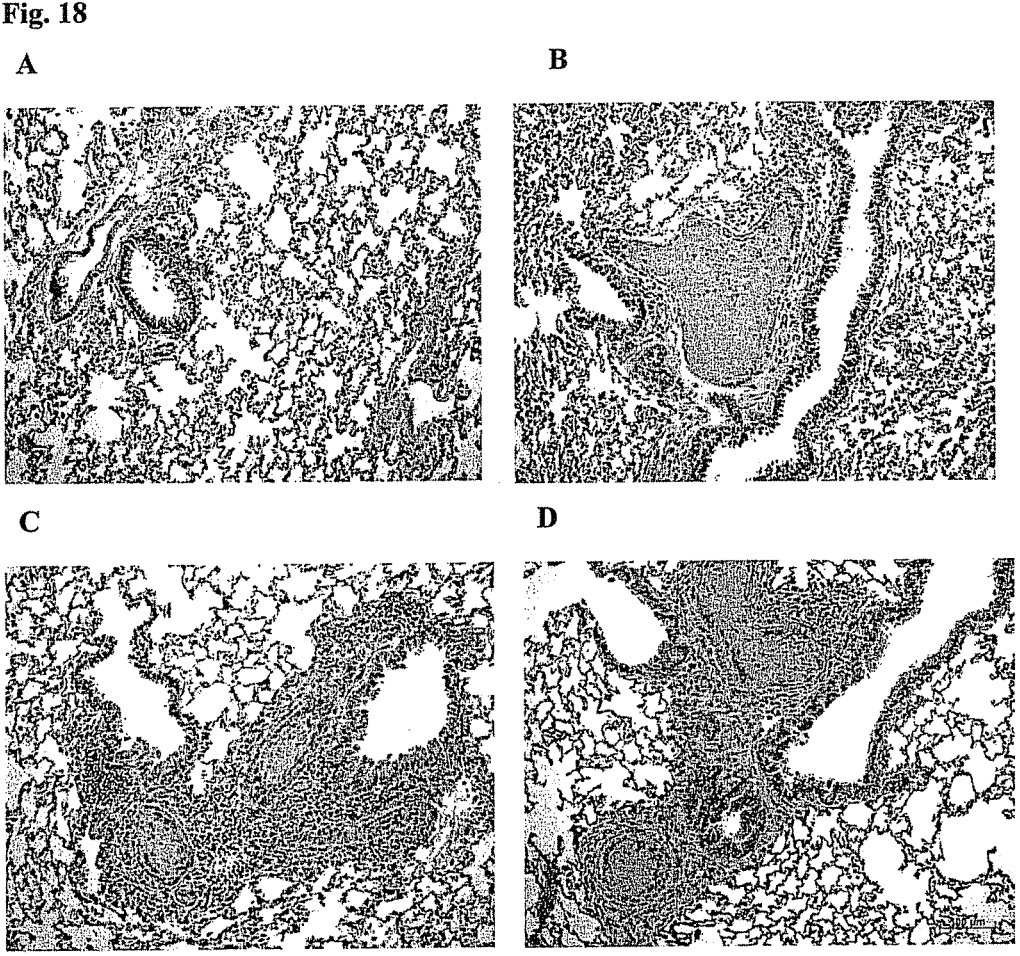
FIG. 18 shows lung sections from (A) control mouse receiving sham-loaded erythrocytes showing normal histology, (B) control mouse receiving sham-loaded erythrocytes showing embolus occluding pulmonary arteriole, (C) mouse treated twice per week with EE-TP showing emboli and perivascular inflammatory cells and (D) mouse treated once every two weeks showing emboli and perivascular inflammatory cells. 10× original magnification for all micrographs, stained with haematoxylin and eosin.

The bodyweight adjusted spleen weights for both sexes treated twice per week were significantly higher than the control group ($p<0.05$ for male, and $p<0.01$ for female). Additionally the absolute spleen weights were higher than the expected background range (5-95 percentile: males 0.089-0.103 g, females 0.085-0.102 g) for all animals in the study (male and female, both treatment groups and control). All other differences from control, including those achieving statistical significance were only observed in a single sex, showed no dose relationship or were considered to be minor. Such differences from control included low brain (treated once every two weeks, $p<0.05$) and thymus (treated once every two weeks, $p<0.05$; treated twice weekly $p<0.01$) weights in males.

acroscopic examination performed after 4 weeks of treatment revealed enlargement of the spleen in a majority of the animals in all groups including the control. Dark areas on the parenteral site (tail vein) were observed in some animals in all groups and were procedural in origin. The incidence and distribution of all other findings were consistent with the common background of BALB/c mice. Changes related to treatment with EE-TP as observed by light microscopy were noted in the lungs. Thrombi/emboli in the lungs were recorded in all groups, including the control group, accompanied by perivascular inflammatory cells in EE-TP treated animals (FIG. 18). There was an increased incidence and severity noted for the treated groups compared with control, however, there was no relationship to the number of doses administered (Table 16). At the parenteral injection site perivascular inflammation/haemorrhage was observed in all groups. This finding correlated with the gross pathology observation of dark tails at necropsy and was related to the intravenous administration procedure and not to EE-TP. No microscopic lesions were observed in the spleen.

Dog.

For dogs receiving twice weekly treatments (Group 3) the thymus weights of all three females and two of the three males were lower than the control weights. The brain weights in all 3 males receiving twice weekly treatments (Group 3) were increased when compared with the controls. However in the absence of similar findings within the females or any associated microscopic findings in the brain, these weight differences are considered not to be related to treatment. Increased liver weights were apparent for all animals receiving twice weekly treatments (Group 3) and for males receiving treatment once every two weeks (Group 2). However, there was no microscopic correlate and therefore these differences are considered not to be related to treatment. An increased group mean spleen weight was also observed for two of the three females receiving twice weekly treatments. No similar change was noted within the males and no microscopic correlate was observed and therefore these differences are considered not to be related to treatment. All other inter-group differences were minor or lacked dosage-relationship and were therefore attributed to normal biological variation (Table 17).

Figure 19:
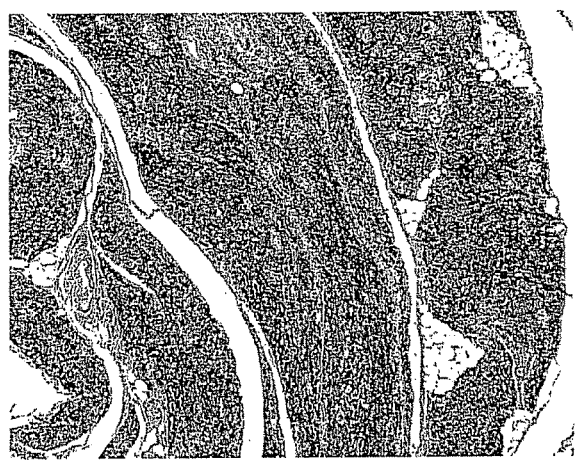
FIG. 19 shows thymus sections from (A) control dog receiving sham-loaded erythrocytes showing normal histology, (B) dog treated twice per week with EE-TP showing moderate atrophy, and (C) dog treated twice per week with EE-TP showing marked atrophy. 4× original magnification for all micrographs, stained with haematoxylin and eosin.
Figure 19:
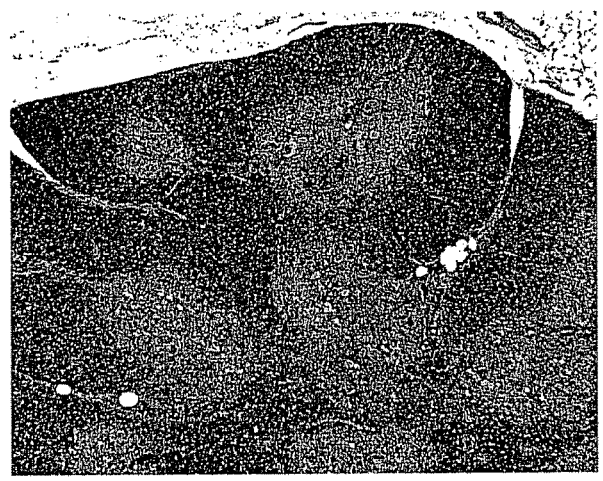
Figure 19:

Macroscopic examination performed after 4 weeks of treatment revealed smaller thymuses in all three females and two of the three males receiving twice weekly treatments (Group 3). Perivascular red areas observed at some parenteral sites were procedural in origin. The incidence and distribution of all the other findings were consistent with the common background. Changes related to treatment with EE-TP seen by light microscopy were in the thymus of animals given the test substance twice weekly. The thymus had slight to marked atrophy in these animals (FIG. 19).

TABLE 10

Specification and batch analysis release results for recombinant thymidine phosphorylase

| Attribute | Acceptance criteria | Batch analysis results |
| --- | --- | --- |
| Appearance | Clear to slightly hazy colourless to yellow liquid | Slightly hazy faint yellow liquid |
| MW size | Main band consistent with reference standard 45 kD | 45 kD |
| | Purity ≥ 95% | ≥99% |

TABLE 10-continued

Specification and batch analysis release results for recombinant thymidine phosphorylase

| Attribute | Acceptance criteria | Batch analysis results |
| --- | --- | --- |
| Endotoxin | NMT 4,000 EU/ml | 90-150 EU/ml |
| Identity | Matches N terminal amino acid sequence (NCBI BLAST) of MFLAQEIIRK | Identical to NCBI BLAST (100% alignment) |
| Residual host cell DNA | NMT 10 ppb | 0.0002 to 0.001 ppb |
| Bioburden | NMT 10 CFU/ml | 0 CFU/ml |
| Kanamycin | NMT 10 ppm | 0.23 ppm |

TABLE 11

Haematological characteristics (Mean ± SEM) of test and control materials

| | Mouse | | Dog | |
| --- | --- | --- | --- | --- |
| Parameter | EE-TP (n = 9) | Sham-loaded (n = 9) | EE-TP (n = 72) | Sham-loaded (n = 54) |
| MCV (fl) | 37.9 ± 0.4 | 37.1 ± 1.0 | 59.2 ± 0.4 | 61.2 ± 0.4 |
| MCH (pg) | 10.2 ± 0.4 | 10.1 ± 0.4 | 18.1 ± 0.2 | 18.8 ± 0.2 |
| MCHC (g/dl) | 27.2 ± 1.0 | 26.8 ± 1.2 | 30.6 ± 0.2 | 30.9 ± 0.2 |
| Extracellular Hb (g/l) post formulation (hour)*: | | | | |
| 0 | 0.2 ± 0.0 | 0.2 ± 0.1 | 0.1 ± 0.1 | 0.1 ± 0.1 |
| 6 | 0.2 ± 0.1 | 0.2 ± 0.1 | 0.1 ± 0.1 | 0.1 ± 0.1 |
| 24 | 0.6 ± 0.2 | 0.6 ± 0.2 | 0.6 ± 0.3 | 0.6 ± 0.2 |
| Encapsulated thymidine phosphorylase (IU/ml) | 123.7 ± 8.5 | NA | 147.9 ± 5.9 | NA |
| Extracellular thymidine phosphorylase (IU/ml) post formulation (hour)*: | | | | |
| 0 | 0.2 ± 0.1 | NA | 0.3 ± 0.0 | NA |
| 6 | 0.3 ± 0.1 | NA | 0.6 ± 0.0 | NA |
| 24 | 1.7 ± 0.1 | NA | 2.4 ± 0.1 | NA |

NA, Not applicable
*n = 4

TABLE 11

Treatment groups in 4 Week mouse and dog studies

| Species | Group | Treatment | Mean Dose (IU/kg/occasion) | Days of dosing | No. of animals Male | No. of animals Female |
| --- | --- | --- | --- | --- | --- | --- |
| Mouse | 1 | Sham loaded erythrocytes | 0 | 1, 4, 8, 11, 5, 18, 22, 25, and 29 | 10 | 10 |
| | 2 | EE-TP | 364 ± 48 | 1, 15, 29 | 10 | 10 |
| | 3 | EE-TP | 330 ± 23 | 1, 4, 8, 11, 15, 18, 22, 25, and 29 | | |

TABLE 11-continued

Treatment groups in 4 Week mouse and dog studies

| Species | Group | Treatment | Mean Dose (IU/kg/occasion) | Days of dosing | No. of animals Male | Female |
|---|---|---|---|---|---|---|
| Dog | 1 | Sham loaded erythrocytes | 0 | 1, 4, 8, 11, 15, 18, 22, 25, and 29 | 3 | 3 |
|  | 2 | EE-TP | 194 ± 15 | 1, 15, 29 | 3 | 3 |
|  | 3 | EE-TP | 200 ± 7 | 1, 4, 8, 11, 15, 18, 22, 25, and 29 | 3 | 3 |

TABLE 12

Selected clinical chemistry parameters (Mean ± SD) for mice treated for 4 weeks

| Parameter/ Sex | Control Twice weekly Group 1 (n = 5) | Once every two weeks Group 2 (n=5) | Twice weekly Group 3 (n = 5) |
|---|---|---|---|
| Cholesterol (mM) | | | |
| Males | 2.73 ± 0.22 | 3.15 ± 0.30* | 2.97 ± 0.29 |
| Females | 2.31 ± 0.04 | 2.24 ± 0.23 | 2.09 ± 0.08* |
| Triglyceride (mM) | | | |
| Males | 0.92 ± 0.12 | 2.62 ± 0.30** | 1.49 ± 0.39** |
| Females | 1.62 ± 0.77 | 2.13 ± 0.26 | 1.43 ± 0.25 |
| Urea (mM) | | | |
| Males | 9.69 ± 1.20 | 8.34 ± 1.51 | 7.95 ± 0.45* |
| Females | 8.36 ± 0.82 | 6.84 ± 0.58** | 6.20 ± 0.84** |
| Creatinine (μM) | | | |
| Males | 6.0 ± 1.5 | 5.0 ± 1.6 | 4.0 ± 1.9* |
| Females | 7.0 ± 1.7 | 8.0 ± 2.2 | 7.0 ± 1.8 |
| Calcium (mM) | | | |
| Males | 2.21 ± 0.06 | 2.14 ± 0.11 | 2.36 ± 0.15** |
| Females | 2.21 ± 0.20 | 2.20 ± 0.29 | 2.32 ± 0.10 |
| Alkaline phosphatase (U/l) | | | |
| Males | 127 ± 11.3 | 131 ± 11.2 | 118 ± 25.9 |
| Females | 159 ± 10.1 | 153 ± 7.8 | 141 ± 17.7* |

Groups compared using student's t-test
*$p < 0.05$ (for comparisons with Group 1)
**$p < 0.01$ (for comparisons with Group 1)

TABLE 13

Selected haematology parameters (Mean ± SD) for mice treated for 4 weeks

| Parameter/ Sex | Control Twice weekly Group 1 (n = 5) | Once every two weeks Group 2 (n = 5) | Twice weekly Group 3 (n = 5) |
|---|---|---|---|
| RBC ($\times 10^{12}$/l) | | | |
| Males | 10.03 ± 0.41 | 9.80 ± 0.55 | 9.83 ± 0.53 |
| Females | 9.79 ± 0.29 | 9.72 ± 0.73 | 9.22 ± 0.32 |
| Hb (g/dl) | | | |
| Males | 15.2 ± 0.66 | 14.7 ± 0.99 | 14.9 ± 0.79 |
| Females | 15.1 ± 0.28 | 15.5 ± 0.99 | 14.6 ± 0.52 |
| Hct (l/l) | | | |
| Males | 0.48 ± 0.03 | 0.48 ± 0.02 | 0.47 ± 0.02 |
| Females | 0.48 ± 0.01 | 0.48 ± 0.03 | 0.45 ± 0.01* |
| MCH (pg) | | | |
| Males | 15.2 ± 0.06 | 15.1 ± 0.96 | 15.1 ± 0.23 |
| Females | 15.4 ± 0.36 | 16.0 ± 0.17** | 15.8 ± 0.16* |
| MCHC (g/dl) | | | |
| Males | 32.0 ± 0.82 | 30.9 ± 2.19 | 31.8 ± 0.77 |
| Females | 31.5 ± 0.77 | 32.3 ± 0.51* | 32.6 ± 0.38* |

Groups compared using student's t-test
*$p < 0.05$ (for comparisons with Group 1)
**$p < 0.01$ (for comparisons with Group 1)

TABLE 14

Urinalysis Parameters (Mean ± SD) for Dog predose and after treatment for 4 Weeks

| Parameter/ Sex | Day | Control Twice weekly Group 1 (n = 3) | Once every two weeks Group 2 (n = 3) | Twice weekly Group 3 (n = 3) |
|---|---|---|---|---|
| pH | | | | |
| Males | Predose | 5.1 ± 0.17 | 5.2 ± 0.06 | 5.2 ± 0.21 |
|  | 28 | 5.0 ± 0.25 | 5.1 ± 0.10 | 6.2 ± 0.46 |
| Females | Predose | 5.3 ± 0.12 | 5.3 ± 0.12 | 5.3 ± 0.06 |
|  | 28 | 5.0 ± 0.12 | 5.1 ± 0.12 | 5.5 ± 0.38 |

TABLE 14-continued

Urinalysis Parameters (Mean ± SD) for Dog predose and after treatment for 4 Weeks

| Parameter/Sex | Day | Treatment | | |
|---|---|---|---|---|
| | | Control Twice weekly Group 1 (n = 3) | Once every two weeks Group 2 (n = 3) | Twice weekly Group 3 (n = 3) |
| Specific gravity (g/l) | | | | |
| Males | Predose | 1034 ± 7.0 | 1031 ± 4.6 | 1035 ± 3.5 |
| | 28 | 1028 ± 12.3 | 1030 ± 2.6 | 1019 ± 4.5 |
| Females | Predose | 1027 ± 5.1 | 1027 ± 9.0 | 1034 ± 3.6 |
| | 28 | 1025 ± 2.3 | 1029 ± 8.1 | 1025 ± 4.6 |
| Protein (g/l) | | | | |
| Males | Predose | 0.10 ± 0.02 | 0.10 ± 0.02 | 0.14 ± 0.09 |
| | 28 | 0.09 ± 0.06 | 0.09 ± 0.02 | 0.04 ± 0.02 |
| Females | Predose | 0.10 ± 0.01 | 0.08 ± 0.04 | 0.11 ± 0.02 |
| | 28 | 0.10 ± 0.05 | 0.09 ± 0.05 | 0.05 ± 0.02 |
| Chloride (mmol) | | | | |
| Males | Predose | 41.67 ± 6.19 | 27.33 ± 9.21 | 28.46 ± 11.10 |
| | 28 | 34.47 ± 6.51 | 36.86 ± 15.65 | 58.99 ± 14.83 |
| Females | Predose | 41.07 ± 5.48 | 27.37 ± 7.59 | 37.95 ± 3.34 |
| | 28 | 32.58 ± 5.41 | 19.52 ± 6.61 | 35.99 ± 17.04 |
| Sodium (mmol) | | | | |
| Males | Predose | 13.44 ± 1.93 | 5.03 ± 2.35 | 6.41 ± 6.05 |
| | 28 | 10.68 ± 4.57 | 11.47 ± 8.82 | 52.90 ± 2.92 |
| Females | Predose | 6.28 ± 1.52 | 4.93 ± 1.97 | 8.38 ± 4.78 |
| | 28 | 4.31 ± 0.86 | 3.75 ± 3.09 | 21.34 ± 23.84 |
| Potassium (mmol) | | | | |
| Males | Predose | 33.67 ± 3.84 | 21.53 ± 4.95 | 22.89 ± 8.75 |
| | 28 | 26.28 ± 4.75 | 27.78 ± 8.31 | 24.67 ± 4.03 |
| Females | Predose | 28.35 ± 3.71 | 22.04 ± 7.01 | 28.96 ± 1.66 |
| | 28 | 23.67 ± 5.25 | 14.72 ± 2.34 | 17.49 ± 2.71 |

TABLE 15

Selected haematology parameters (Mean ± SD) for dogs predose, during and after treatment for 4 weeks

| Parameter/Sex | Day | Treatment | | |
|---|---|---|---|---|
| | | Control Twice weekly Group 1 | Once every two weeks Group 2 | Twice weekly Group 3 |
| RBC ($\times 10^{12}$/l) | | | | |
| Males | Predose | 6.20 ± 0.39 | 5.92 ± 0.32 | 5.68 ± 0.09 |
| | 14 | 5.50 ± 0.18 | 5.51 ± 0.19 | 4.45 ± 0.38 |
| | 21 | 5.40 ± 0.25 | 5.39 ± 0.39 | 4.67 ± 0.22 |
| | 28 | 5.70 ± 0.27 | 6.10 ± 0.47 | 5.10 ± 0.46 |
| Females | Predose | 5.85 ± 0.36 | 6.04 ± 0.17 | 6.19 ± 0.66 |
| | 14 | 5.17 ± 0.51 | 5.83 ± 0.37 | 5.76 ± 0.29 |
| | 28 | 5.15 ± 0.32 | 6.06 ± 0.23 | 5.76 ± 0.61 |
| Hb (g/dl) | | | | |
| Males | Predose | 14.1 ± 0.75 | 13.0 ± 0.31 | 13.0 ± 0.61 |
| | 14 | 12.8 ± 0.26 | 12.4 ± 0.25 | 10.8 ± 1.10 |
| | 21 | 12.3 ± 0.42 | 12.2 ± 1.25 | 11.2 ± 1.00 |
| | 28 | 12.5 ± 0.31 | 13.3 ± 1.05 | 11.7 ± 1.53 |
| Females | Predose | 14.1 ± 1.10 | 14.0 ± 0.30 | 14.2 ± 1.45 |
| | 14 | 12.2 ± 1.39 | 13.5 ± 0.95 | 13.0 ± 0.35 |
| | 28 | 12.2 ± 0.62 | 13.3 ± 0.50 | 12.6 ± 1.48 |
| Hct (l/l) | | | | |
| Males | Predose | 0.43 ± 0.03 | 0.40 ± 0.01 | 0.40 ± 0.02 |
| | 14 | 0.37 ± 0.01 | 0.36 ± 0.01 | 0.31 ± 0.03 |
| | 21 | 0.38 ± 0.02 | 0.37 ± 0.04 | 0.34 ± 0.03 |
| | 28 | 0.40 ± 0.02 | 0.42 ± 0.03 | 0.37 ± 0.43 |
| Females | Predose | 0.42 ± 0.03 | 0.42 ± 0.01 | 0.42 ± 0.04 |
| | 14 | 0.37 ± 0.04 | 0.40 ± 0.02 | 0.40 ± 0.01 |
| | 28 | 0.39 ± 0.02 | 0.42 ± 0.02 | 0.40 ± 0.05 |
| Reticulocyte (%) | | | | |
| Males | Predose | 1.30 ± 0.21 | 0.80 ± 0.27 | 0.90 ± 0.40 |
| | 14 | 2.00 ± 0.20 | 1.00 ± 0.22 | 2.80 ± 0.51 |
| | 21 | 1.80 ± 0.22 | 1.30 ± 0.28 | 2.80 ± 1.14 |
| | 28 | 1.40 ± 0.32 | 1.40 ± 0.34 | 2.40 ± 0.95 |
| Females | Predose | 1.50 ± 0.60 | 1.40 ± 0.16 | 1.50 ± 0.19 |
| | 14 | 2.20 ± 0.39 | 1.40 ± 0.24 | 2.30 ± 0.23 |
| | 28 | 2.00 ± 0.26 | 1.60 ± 0.56 | 2.80 ± 1.39 |
| Platelet count ($\times 10^9$/l) | | | | |
| Males | Predose | 352 ± 30.2 | 376 ± 50.3 | 390 ± 11.5 |
| | 14 | 353 ± 34.4 | 280 ± 63.1 | 122 ± 40.1 |
| | 21 | 361 ± 27.0 | 207 ± 19.3 | 233 ± 14.8 |
| | 28 | 401 ± 19.6 | 310 ± 21.1 | 286 ± 41.0 |
| Females | Predose | 349 ± 18.5 | 354 ± 84.9 | 370 ± 30.0 |
| | 14 | 368 ± 21.1 | 239 ± 66.4 | 290 ± 26.9 |
| | 28 | 359 ± 31.5 | 300 ± 57.5 | 227 ± 115.0 |

TABLE 16

Summary of treatment related findings in the lungs of mice after treatment for 4 weeks

| Sex/Group Dose frequency | Male 1 Twice/week | Male 2 Once/two weeks | Male 3 Twice/week | Female 1 Twice/week | Female 2 Once/two weeks | Female 3 Twice/week |
|---|---|---|---|---|---|---|
| Thrombus/Embolus | | | | | | |
| Minimal | 1 | 3 | 2 | 1 | 3 | 5 |
| Slight | 0 | 2 | 0 | 0 | 2 | 2 |
| Moderate | 0 | 0 | 0 | 0 | 1 | 2 |
| Marked | 0 | 0 | 0 | 0 | 1 | 0 |
| Total | 1 | 5 | 2 | 1 | 7 | 9 |

TABLE 16-continued

Summary of treatment related findings in the lungs of mice after treatment for 4 weeks

| Sex/Group<br>Dose frequency | Male 1<br>Twice/week | Male 2<br>Once/two<br>weeks | Male 3<br>Twice/week | Female 1<br>Twice/week | Female 2<br>Once/two<br>weeks | Female 3<br>Twice/week |
|---|---|---|---|---|---|---|
| Perivascular<br>Inflammatory cells | | | | | | |
| Minimal | 0 | 2 | 1 | 0 | 3 | 6 |
| Slight | 0 | 1 | 0 | 0 | 2 | 1 |
| Moderate | 0 | 0 | 0 | 0 | 1 | 1 |
| Total | 0 | 3 | 1 | 0 | 6 | 8 |
| Number of animals examined | 10 | 9 | 10 | 10 | 10 | 10 |

TABLE 17

Weights of selected organs (Mean ± SD) for dogs receiving treatment for 4 Weeks

| Parameter/<br>Sex | Treatment | | |
|---|---|---|---|
| | Control<br>Twice weekly<br>Group 1 | Once every<br>two weeks<br>Group 2 | Twice<br>weekly<br>Group 3 |
| Thymus (g) | | | |
| Males | 11.91 ± 2.67 | 18.43 ± 13.40 | 4.12 ± 2.56 |
| Females | 19.56 ± 12.15 | 10.97 ± 5.4 | 2.35 ± 0.91 |
| Brain (g) | | | |
| Males | 83.0 ± 5.2 | 82.5 ± 2.4 | 94.5 ± 2.8 |
| Females | 78.3 ± 7.2 | 76.6 ± 9.9 | 73.9 ± 5.3 |
| Liver (g/) | | | |
| Males | 365 ± 7 | 415 ± 36 | 471 ± 21 |
| Females | 324 ± 33 | 311 ± 32 | 379 ± 29 |
| Spleen (g) | | | |
| Males | 94.1 ± 34.1 | 113.6 ± 17.0 | 111.8 ± 29.9 |
| Females | 74.4 ± 19.0 | 62.1 ± 5.1 | 98.3 ± 33.3 |
| Heart (g) | | | |
| Males | 83.1 ± 11.0 | 84.4 ± 9.2 | 84.1 ± 8.5 |
| Females | 79.1 ± 9.1 | 71.5 ± 10.5 | 79.5 ± 8.1 |
| Kidneys (g) | | | |
| Males | 54.3 ± 3.6 | 60.6 ± 4.4 | 59.1 ± 2.5 |
| Females | 47.9 ± 3.4 | 49.9 ± 5.8 | 51.3 ± 4.1 |

Discussion

EE-TP was formulated using a reversible hypo-osmotic dialysis, permitting the administration of 330 to 364 IU/kg/occasion in the mouse and 194 to 200 IU/kg/occasion in the dog. The proposed anticipated clinical dose of thymidine phosphorylase is 200 IU/kg/two weeks, and thus exposures 6.6 fold and 4 fold higher than this dose were administered respectively in the mice and dogs receiving EE-TP twice per week, achieving satisfactory safety margins for clinical trials. The stability data demonstrated that the time delay between EE-TP formulation and infusion had no effect of the encapsulated thymidine phosphorylase activity and thus the dose administered. Extracellular thymidine phosphorylase activity at six hours post formulation represented 0.2% and 0.4% of the total erythrocyte encapsulated enzyme for the mouse and dog erythrocyte, respectively demonstrating the stability of the erythrocyte carrier during the period between EE-TP formulation and infusion. In the clinical setting it is anticipated that EE-TP infusion will take place within 24 hours of formulation.

In the 4 week mouse study, an increased incidence and severity of thrombi/emboli in the lungs was recorded in EE-TP treated animals, compared with the controls. This was associated with the presence of perivascular inflammatory cells which is a normal response to the presence of thrombi/emboli. Thrombi in the lungs resulted in the death of one test substance treated mouse and may also be linked to the clinical signs noted towards the end of the treatment period (ungroomed appearance, piloerection, and hunched posture). The mouse studies employed allogeneic erythrocytes and as this finding was not observed in the dog studies which used autologous erythrocytes, this effect may be related to the intravenous administration of foreign erythrocytes and/or the action of antibodies on the administered erythrocytes. The perivascular recruitment of inflammatory cells may also be a consequence of lung inflammation caused by the local release of thymidine phosphorylase, and would explain the greater incidence and severity of thrombi and emboli in the EE-TP treated animals. There is no evidence of this effect in the lungs of the patient who has received twice monthly infusions of erythrocyte encapsulated adenosine deaminase over a period of 16 years (Bax et al., 2007).

The splenic enlargement and high spleen weights observed in both EE-TP treated and control mice may reflect a pooling of erythrocytes due to administration to animals with a full complement of erythrocytes, or alternatively a sequestration of infused erythrocytes by the spleen for conditioning and later release back into the circulation. The spleen acts as a reservoir for blood and is the most discriminating organ for monitoring the integrity of erythrocytes and removes senescent or abnormal erythrocytes from the circulation (Harris et al., 1957). The absence of microscopic lesions in the spleen would indicate that spleen enlargement was not caused by an excessive destruction of erythrocytes by erythrophagocytosis. Our in vivo studies of human chromium (51 Cr)-labeled erythrocyte carriers demonstrated a sequestration of between 51 and 97% of the cells within the first 144 hours of infusion, as measured by surface counting, and this was followed thereafter by an almost total release of cells back into the circulation suggesting that the erythrocytes were initially retained by the spleen for repair and this mechanism could explain the splenic enlargement observed here (Bax et al., 1999).

Anisocytosis was observed in the majority of treated and control mice and this was probably induced by the dialysis procedure, which in the mouse erythrocyte results in a cell volume reduction of 29 to 39%. This compares to a reduction of 6 to 18% in the human and dog erythrocyte volumes and a subsequent in vivo normalisation of cell size.

Administration of EE-TP to mice once every two weeks or twice weekly resulted in an antibody response, with a greater incidence of anti-thymidine phosphorylase antibodies observed in the group treated once every 2 weeks. These results are consistent with our previous studies in the BALB/c mouse where the administration of antigen-loaded erythrocytes was shown to elicit humoral immune responses (Murray et al., 2006). The source of thymidine phosphorylase employed in these current studies was a recombinant *E. coli* protein sharing a 40% amino acid sequence homology with the human sequence (Barton et al., 1992). Although encapsulation within erythrocytes would be predicted to reduce immunogenicity of the native enzyme, an intravascular release of thymidine phosphorylase from damaged or fragile erythrocytes is likely to elicit an immunogenic reaction. This is of significant interest with regard to the clinical application of EE-TP; despite raising an anti-thymidine phosphorylase antibody response, the erythrocyte carrier can simultaneously protect the encapsulated thymidine phosphorylase from circulating antibodies. In the clinical setting, immunogenic reactions have been reported to occur with most therapeutic proteins, with the incidence ranging between less than 10% of patients, to nearly 100% (Schellekens, 2004). The monitoring of antibodies responses during pre-clinical and clinical safety testing of therapeutic proteins and, in some instances, after marketing approval is thus an important issue.

In the dog, although treatment twice weekly was tolerated for 4 weeks, the observed level of clinical signs during or shortly after dosing from Day 11 onwards were significant, and increased with each subsequent dosing occasion. In the clinical setting, nausea and erythema of the face, neck and in the arm proximal to infusion have previously been observed in patients receiving EE-TP under compassionate use, and these were successfully prevented using antihistamine, corticosteroid anti-inflammatory and anti-emetic drugs prior to treatment. This approach was undertaken for dogs receiving twice weekly treatments from Day 18 onwards for a majority of the animals. As a result of these predose medications the incidence and degree of clinical signs was initially notably reduced, however with each subsequent administration the signs increased again. Dogs treated every second week showed a similar pattern of clinical signs on the second and third administration (Day 15 and 29). The delayed appearance of these clinical signs, their transient nature associated with dosing and their subsequent successful treatment with anti-inflammatory drugs, suggested an immune based response to the administration of EE-TP. As there was no similar finding within the control dogs, it is concluded that thymidine phosphorylase was responsible.

Non-specific antibodies were detected at the end of the study in all dogs given EE-TP and specific anti-thymidine phosphorylase antibodies were detected in only two dogs. It would therefore appear that the clinical signs were associated with the non-specific antibodies or with a cell based immune response, and not with a specific anti-thymidine phosphorylase response. The thymidine phosphorylase preparation contained low levels of process related endotoxins, and although a majority of these would have been removed by the dialysis process employed in the formulation of EE-TP, there is the possibility that the formation of non-specific antibodies was caused by the presence of residual endotoxins.

The Food and Drug Administration (USA) recommends a maximum endotoxin limit of 5 EU/Kg body weight for parentally administered drugs; the endotoxins levels in the thymidine phosphorylase preparation prior to EE-TP formulation were well below this limit (Brito and Singh, 2011). The absence of specific anti-thymidine phosphorylase antibodies in a majority of the dogs would suggest that removal of EE-TP from the circulation and subsequent catabolism by lysosmal enzymes (the normal route for the degradation of senescent erythrocytes) does not lead to antigen presentation, unlike in the mouse (Murray et al., 2006). It also indicates that there was minimal intravascular haemolysis of the enzyme-loaded erythrocytes, which if occurred would have most likely resulted in the production of specific antibodies against the released thymidine phosphorylase.

Haematology investigations performed during and at the end of the treatment period revealed in all dog groups an apparent haemorrhagic-type anaemia (reductions in haematocrit, haemoglobin concentration and erythrocyte count), with a subsequent increase in reticulocytes. This change is most likely to be due to the hypo-osmotic dialysis procedure used to prepare the sham- and thymidine phosphorylase-loaded erythrocytes; there is a cell loss of approximately 38% during the process and a reduction in the cellular haemoglobin concentration. This would explain why dogs treated once every two weeks were less affected than those treated twice weekly. The haematology results from the end of the treatment period indicated that although these changes were still present, the parameters were returning to normal levels. The increase in reticulocyte numbers demonstrated that the bone marrow was responding to the anemia, and for this reason these changes are considered not to be adverse. Pale gums noted during for treated animals may be a result of these haematology changes. The magnitude in the reduction of platelet counts observed in EE-TP treated dogs appeared to be less at the end of the treatment period, also suggesting an adaptive response and for this reason these changes are considered not to be adverse.

Microscopic changes related to test article were seen as slight to markedly atrophic in the thymus of dogs receiving EE-TP every two weeks (Group 3). This finding correlated with the small size of the thymus observed during macroscopic examination as well as weight changes in the females. The thymus is known to be sensitive to acute stress-induced atrophy and these changes are likely to be related to the stress produced by the clinical reaction which in turn may underlie the lower bodyweight gain by this group (Pearse, 2006).

REFERENCES

Aksoy F, Demirel G, Bilgiç T, Güngör I G, Ozçelik A. A previously diagnosed mitochondrial neurogastrointestinal encephalomyopathy patient presenting with perforated ileal diverticulitis. Turkish Journal of Gastroenterology. 2005; 16: 228-231.

Altschul S. A protein alignment scoring system sensitive at all evolutionary distances. J. Mol. Evol. 1993; 36: 290-300

Altschul S, Gish W, Miller W, Myers E, Lipman D. Basic local alignment search tool. J. Mol. Biol. 1990; 215: 403-410

Angervall, L., and Carlström, E. Theoretical criteria for the use of relative organ weights and similar ratios in biology. J. Theoret Biol. 1963; 4; 254-259.

Bariş Z, Eminoğlu T, Dalgiç B, Tümer L, Hasanoğlu A. Mitochondrial neurogastrointestinal encephalomyopathy (MNGIE): case report with a new mutation. European Journal of Pediatrics. 2010; 169:1375-1378.

Bartlett, M S. Properties of sufficiency and statistical tests. P. Roy. Soc. Lond. A Mat. 1937: 160; 268-282.

Barton G J, Ponting C P, Spraggon G, Finnis C, and Sleep D. Human platelet-derived endothelial cell growth factor is homologous to *Escherichia coli* thymidine phosphorylase. Protein Science. 1992; 1: 688-690.

Bax B E, Bain M D, Talbot P J, Parker-Williams E J and Chalmers R A. In vivo survival of human carrier erythrocytes. Clinical Science. 1999; 1096: 171-178.

Bax B E, Bain M D, Fairbanks L D, Webster A D B and Chalmers R A. In vitro and in vivo studies of human carrier erythrocytes loaded with polyethylene glycol-conjugated and native adenosine deaminase. British Journal of Haematology. 2000; 109: 549-554.

Bax B E, Bain M D, Fairbanks L D, Webster A D B, Ind P W, Hershfield M S and Chalmers R A. A nine year evaluation of carrier erythrocyte encapsulated adenosine deaminase therapy in a patient with adult-type adenosine deaminase deficiency. European Journal of Haematology. 2007; 79: 338-348.

Brito, L A, and Singh, M. Acceptable Levels of Endotoxin in Vaccine Formulations During Preclinical Research J. Pharm. Sci. 2011: 100; 34-37.

Cardaioli E, Da Pozzo P, Malfatti E, Battisti C, Gallus G N, Gaudiano C, Macucci M, Malandrini A, Margollicci M, Rubegni A, Dotti M T, Federico A. A second MNGIE patient without typical mitochondrial skeletal muscle involvement. Neurological Sciences. 2010; 31: 491-494.

Celebi N, Sahin A, Canbay O, Uzümcügil F, Aypar U. Abdominal pain related to mitochondrial neurogastrointestinal encephalomyopathy syndrome may benefit from splanchnic nerve blockade. Paediatric Anaesthesia. 2006; 16: 1073-1076.

Chalmers R. Comparison and potential of hypo-osmotic and iso-osmotic erythrocyte ghosts and carrier erythrocytes as drug and enzyme carriers. Bibl. Haematol. 1985: 51; 15-24.

Chinnery P F and Turnbull D M. Epidemiology and Treatment of Mitochondrial Disorders. American Journal of Medical Genetics 2001; 106: 94-101.

Devereux J, Haeberli P and Smithies O. A comprehensive set of sequence analysis programs for the VAX. Nucleic Acids Research. 1984; 12: 387-395

Eccleston P A, Funa K and Heldin C-H. Neurons of the peripheral nervous system express thymidine phosphorylase. Neuroscience Letters. 1995; 192: 137-141.

EC Commission Directive 2004/10/EC of 11 Feb. 2004 (Official Journal No L 50/44).

EMEA, 2006. Committee for Medicinal Products for Human Use (CHMP). The Guideline on Immunogenicity Assessment of Biotechnology-Derived Therapeutic Proteins. (Effective April 2008), EMEA/CHMP/BMWP/14327/2006). Available from: http://www.emea.europa.eu/docs/en_GB/document_library/Scientific_guideline/2009/09/WC500003946.pdf (Accessed May 11, 2012).

FDA, 2001. Centre for Drug Evaluation and Research. Centre for Veterinary Medicine. Guidance for Industry: Bioanalytical Methods Validation. Available from: http://www.fda.gov/downloads/Drugs/GuidanceCompliance-RegulatoryInformation/Guidances/ucm070107.pdf. (Accessed May 11, 2012).

FDA, 2009. Centre for Drug Evaluation and Research. Centre for Biologics Evaluation and Research. Draft Guidance for Industry: Assay Development for Immunogenicity Testing of Therapeutic Proteins. Available from: http://www.fda.gov/downloads/Drugs/GuidanceCompli-anceRegulatoryInformation/Guidances/UCM192750.pdf (Accessed May 11, 2012).

Fisher R A. Statistical Methods for Research Workers, 14th edn., p. 96. Hafner Publishing Company, New York, USA (1973).

Giordano C, Sebastiani M, De Giorgio R, Travaglini C, Tancredi A, Valentino M L, Bellan M, Cossarizza A, Hirano M, d'Amati G, Carelli V. Gastrointestinal dysmotility in mitochondrial neurogastrointestinal encephalomyopathy is caused by mitochondrial DNA depletion. American Journal of Pathology. 2008; 173: 1120-1128.

Halter J, Schüpbach W M, Casali C, Elhasid R, Fay K, Hammans S, Illa I, Kappeler L, Krähenbühl S, Lehmann T, Mandel H, Marti R, Mattle H, Orchard K, Savage D, Sue C M, Valcarcel D, Gratwohl A, Hirano M. Allogeneic hematopoietic SCT as treatment option for patients with mitochondrial neurogastrointestinal encephalomyopathy (MNGIE): a consensus conference proposal for a standardized approach. Bone Marrow Transplantation, 2010; 1-8.

Harris, I M, McAlister, J M and Prankerd, T A J. The relationship of abnormal red cells to the normal spleen. Clin. Sci. 1957: 16; 233-230.

Hirano M, Silvestri G, Blake D M, Lombes A, Minetti C, Bonilla E, Hays A P, Lovelace R E, Butler I, Bertorini T E, Threlkeld A B, Mitsumoto H, Salberg L M, Rowland L P, and DiMauro S. Mitochondrial neurogastrointestinal encephalomyopathy (MNGIE): clinical, biochemical, and genetic features of an autosomal recessive mitochondrial disorder. Neurology. 1994; 44: 721-727.

Hirano M, Nishigaki Y, and Marti R. Mitochondrial Neurogastrointestinal Encephalomyopathy (MNGIE): A disease of two genomes. The Neurologist. 2004; 10: 8-17.

Hirano M, Martí R, Casali C, Tadesse S, Uldrick T, Fine B, Escolar D M, Valentino M L, Nishino I, Hesdorffer C, Schwartz J, Hawks R G, Marton D L, Cairo M S, DiMauro S, Stanzani M, Garvin J H and Savage D G. Allogeneic stem cell transplantation corrects biochemical derangements in MNGIE. Neurology. 2006; 67: 1458-1460.

Hirano M, Casali C, Tadesse S, Stanzani M and Savage D G. Sustained biochemical and clinical improvements two years post-allogeneic stem cell transplantation in a patient with MNGIE. American Academy of Neurology Annual Meeting Abstract 548.002. 2008.

Ihler, G. M., Glew, R. H. and Schnure, F. W. Enzyme loading of erythrocytes. Proceedings of the National Academy of Sciences of the United States of America. 1973; 70: 2663-2666.

la Marca G, Malvagia S, Casetta B, Pasquini E I, Pela L, Hirano M, Donati M A and Zammarchi E. Pre- and post-dialysis quantitative dosage of thymidine in urine and plasma of a MNGIE patient by using HPLC-ESI-MS/MS. Journal of Mass Spectrometry. 2006; 41: 586-592.

Lara M C, Weiss B, Illa I, Madoz P, Massuet L, Andreu A L, Valentino M L, Anikster Y, Hirano M and Marti R. Infusion of platelets transiently reduces nucleoside overload in MNGIE. Neurology. 2006; 67: 1461-1463.

Marti R, Nishigaki Y, and Hirano M. Elevated plasma deoxyuridine in patients with thymidine phosphorylase deficiency. Biochemical and Biophysical Research Communications. 2003; 303: 14-18.

Marti R, Spinazzola A, Tadesse S, Nishino I, Nishigaki Y, and Hirano M. Definitive Diagnosis of Mitochondrial Neurogastrointestinal Encephalomyopathy by Biochemical Assays. Clinical Chemistry. 2004; 50: 120-124.

Matsukawa K, Moriyama A, Kawai Y, Asai K, and Kato T. Tissue distribution of human gliostatin/platelet-derived endothelial cell growth factor (PD-ECGF) and its drug-induced expression. Biochimica et Biophysica Acta. 1996; 1314: 71-82.

Miller K, Bowsher R, Celniker A, Gibbons J, Gupta S, Lee J, Swanson S, Smith W, Weiner R, Workshop on bioanalytical methods validation for macromolecules: summary report, Pharm. Res. 2001:18:1373-1383.

Mire-Sluis A, Barrett Y, Devanarayan V, Koren E, Liu H, Maia M, Parish T, Scott G, Shankar G, Shores E, Swanson S, Taniguchi G, Wierda D, Zuckerman L. Recommendations for the design and optimization of immunoassays used in the detection of host antibodies against biotechnology products, J. Immunol. Meth. 2004: 289; 1-16.

Moran N F, Bain M D, Muqit M and Bax B E. Carrier erythrocyte entrapped thymidine phosphorylase therapy in MNGIE. Neurology. 2008; 71: 686-688.

Murray, A M, Pearson, I F S, Chalmers R A, Bain, M D. and Bax, B E. The mouse immune response to carrier erythrocyte entrapped antigens. Vaccine. 2006: 24; 6129-6139.

Nishigaki Y, Marti R, Copeland W C, and Hirano M. Site-specific somatic mitochondrial DNA point mutations in patients with thymidine phosphorylase deficiency. Journal of Clinical Investigation. 2003; 111: 1913-1921.

Nishigaki Y, Marti R, and Hirano M. ND5 is a hot-spot for multiple atypical mitochondrial DNA deletions in mitochondrial neurogastrointestinal encephalomyopathy. Human Molecular Genetics. 2004; 13: 91-101.

Nishino I, Spinazzola A, and Hirano M. Thymidine phosphorylase gene mutations in MNGIE, a human mitochondrial disorder. Science. 1999; 283: 689-692.

Nishino I, Spinazzola A, Papadimitriou A, Hammnans S, Steiner I, Hahn C. D, Connolly A M, Verloes A, Guimarães J, Maillard I, Hamano H, Donati M A, Semrad C E, Russell J A, Andreu A L, Hadjigeorgiou G M, Vu T H, Tadesse S, Nygaard T G, Nonaka I, Hirano I, Bonilla E, Rowland L P, DiMauro S, and Hirano M. Mitochondrial neurogastrointestinal encephalomyopathy: an autosomal recessive disorder due to thymidine phosphorylase mutations. Annals of Neurology. 2000; 47: 792-800.

Nishino I, Spinazzola A, Hirano M. MNGIE: from nuclear DNA to mitochondrial DNA. Neuromuscular Disorders. 2001; 11: 7-10.

OECD Principles of Good Laboratory Practice (as revised in 1997), ENV/MC/CHEM (98) 17.

Papadimitriou A, Comi G P, Hadjigeorgiou G M, Sordoni A, Sciacco M, Napoli L, Prelle A, Moggio M, Fagiolari G, Bresolin N, Salani S, Anastasopoulos I, Giassakis G, Divari R, and Scarlato G. Partial depletion and multiple deletions of muscle mtDNA in familial MNGIE syndrome. Neurology. 1998; 51: 1086-1092.

Pearse G. Toxicol. Pathol. 2006; 34: 515-547

Said G, Lacroix C, Planté-Bordeneuve V, Messing B, Slama A, Crenn P, Nivelon-Chevallier A, Bedenne L, Soichot P, Manceau E, Rigaud D, Guiochon-Mantel A, Matuchansky C. Clinicopathological aspects of the neuropathy of neurogastrointestinal encephalomyopathy (MNGIE) in four patients including two with a Charcot-Marie-Tooth presentation. Journal of Neurology. 2005; 252: 655-662.

Schellekens, H. Immunogenicity of therapeutic proteins: clinical implications and future prospects. Clin. Ther. 2002: 24; 1720-1740.

Shankar G, Devanarayan V, Amaravadi L, Barrett Y, Bowsher R, Finco-Kent D, Fiscella M, Gorovits B, Kirschner S, Moxness M, Parish T, Quarmby V, Smith H, Smith W, Zuckerman L, Koren E. Recommendations for the validation of immunoassays used for detection of host antibodies against biotechnology products. J. Pharm. Biomed. Anal. 2008; 48; 1267-1281.

Shoffner J M. Mitochondrial Neurogastrointestinal Encephalopathy Disease. In: Pagon R A, Bird T C, Dolan C R, Stephens K, editors. GeneReviews. Seattle (WA): University of Washington, Seattle; 1993-2005 (updated 2010).

Spinazzola A, Martí R, Nishino I, Andreu A L, Naini A, Tadesse S, Pela I, Zammarchi E, Donati M A, Oliver J A, and Hirano, M. Altered thymidine metabolism due to defects of thymidine phosphorylase. Journal of Biological Chemistry. 2002; 277: 4128-4133.

Sprandel U, Clark T B, Hubbard A R, Chalmers R A. Morphology of hemoglobin-containing human erythrocytes "ghosts". Micron. 1981; 12: 29-36.

The Human Gene Mutation Database (HGMD) at the Institute of Medical Genetics in Cardiff http://www.hgmd.cf.ac.uk/ac/all.php Web page accessed Aug. 10, 2010

The UK Good Laboratory Practice Regulations (Statutory Instrument 1999 No. 3106, as amended by Statutory Instrument 2004 No. 994).

Usuki K, Norberg L, Larsson E, Miyazono K, Hellman U, Wernstedt C, Rubin K, and Heldin C-H. Localization of platelet-derived endothelial cell growth factor in human placenta and purification of an alternatively processed form. Cell Regulation. 1990; 1: 577-584.

Valentino M, Martí R, Tadesse S, López L, Manes J, Lyzak J, Hahn A, Carelli V, and Hirano M. Thymidine and deoxyuridine accumulate in tissues of patients with mitochondrial neurogastrointestinal encephalomyopathy (MNGIE). FEBS Letters. 2007; 581: 3410-3414.

Wilcoxon F. Individual comparisons by ranking methods. Biom. Bull. 1945: 1; 80-83.

Sequence Listing

```
                                                        SEQ ID NO: 1
(E. coli thymidine phosphorylase)
        10         20         30         40         50         60
 MFLAQEIIRK KRDGHALSDE EIRFFINGIR DNTISEGQIA ALAMTIFFHD MTMPERVSLT 70         80         90        100        110        120
 MAMRDSGTVL DWKSLHLNGP IVDKHSTGGV GDVTSLMLGP MVAACGGYIP MISGRGLGHT 130        140        150        160        170        180
 GGTLDKLESI PGFDIFPDDN RFREIIKDVG VAIIGQTSSL APADKRFYAT RDITATVDSI 190        200        210        220        230        240
 PLITASILAK KLAEGLDALV MDVKVGSGAF MPTYELSEAL AEAIVGVANG AGVRTTALLT
```

-continued

```
              250         260         270         280         290         300
       DMNQVLASSA GNAVEVREAV QFLTGEYRNP RLFDVTMALC VEMLISGKLA KDDAEARAKL 310         320         330         340         350         360
       QAVLDNGKAA EVFGRMVAAQ KGPTDFVENY AKYLPTAMLT KAVYADTEGF VSEMDTRALG 370         380         390         400         410         420
       MAVVAMGGGR RQASDTIDYS VGFTDMARLG DQVDGQRPLA VIHAKDENNW QEAAKAVKAA 430         440
       IKLADKAPES TPTVYRRISE
```

---

The invention claimed is:

1. A method of treating mitochondrial neurogastrointestinal encephalomyopathy (MNGIE) in a patient, comprising administering to the patient autologous erythrocytes that contain bacterial thymidine phosphorylase and are free of animal proteins other than proteins derived from the patient, said animal proteins comprise BSA, wherein the number of autologous erythrocytes is from $50 \times 10^{10}$ to $92 \times 10^{10}$, wherein the autologous erythrocytes comprise less than 200 EU of endotoxin per mg of bacterial thymidine phosphorylase, wherein the bacterial thymidine phosphorylase is administered to the patient at a concentration of less than 300 IU of bacterial thymidine phosphorylase per $1 \times 10^{10}$ erythrocytes, thereby treating mitochondrial neurogastrointestinal encephalomyopathy (MNGIE) in the patient.

2. The method according to claim 1, wherein the bacterial thymidine phosphorylase is an *E. coli* thymidine phosphorylase and/or, wherein the thymidine phosphorylase comprises the sequence shown in SEQ ID NO: 1 or a variant thereof, wherein the variant is at least 50%, at least 55%, at least 60%, at least 65%, at least 70%, at least 75%, at least 80%, at least 85%, at least 90% or at least 95%, at least 97% or at least 99% identical to the amino acid sequence of SEQ ID NO: 1.

3. The method according to claim 1, wherein the bacterial thymidine phosphorylase is administered to the patient at a dose of from 30 to 300 IU/kg, 50 to 200 IU/kg or 75 to 150 IU/kg.

4. The method of claim 1, wherein the number of autologous erythrocytes administered to the patient is from $50 \times 10^{10}$ to $92 \times 10^{10}$, from $75 \times 10^{10}$ to $92 \times 10^{10}$, or from $80 \times 10^{10}$ to $92 \times 10^{10}$; wherein the autologous erythrocytes are administered to the patient:
   (a) at least once a month;
   (b) at least once every two weeks; or
   (c) at least once a week.

5. The method according to claim 1, wherein the patient is treated for a time period of at least 3 months, at least 6 months, at least 12 months, at least 24 months, or throughout the life of the patient.

6. The method according to claim 1, wherein thymidine or deoxyuridine concentrations in the patient's blood plasma is reduced to 70% or less, 60% or less, 50% or less, 40% or less, 30% or less, 20% or less, 10% or less, 5% or less, 2% or less or 0% of the pre-treatment concentration at a time point from 3 to 12 months, optionally 6 to 10 months, after the start of the treatment; and/or wherein the concentration of thymidine or deoxyuridine in the patient's urine is reduced to less than 70%, less than 50%, less than 20%, less than 10%, less than 5%, less than 2%, or 0% of the pre-treatment concentration at a time point of 3 to 12 months, optionally 6 to 10 months, after the start of the treatment.

7. The method according to claim 1, wherein the autologous erythrocytes containing thymidine phosphorylase are prepared by collecting erythrocytes from the patient, loading the erythrocytes with thymidine phosphorylase, and administering the loaded autologous erythrocytes to the patient.

8. The method according to claim 1, wherein treatment comprises improving symptoms associated with MNGIE.

9. The method according to claim 8, wherein the symptoms are selected from gastrointestinal, muscular or neuronal.

10. The method according to claim 8, wherein the symptoms are selected from gait, balance, sensory, and finger function.

11. The method according to claim 1 wherein the bacterial thymidine phosphorylase is administered to the patient at a dose of about 25 to 100 IU of bacterial thymidine phosphorylase per $1 \times 10^{10}$ erythrocytes.

12. A composition comprising from $50 \times 10^{10}$ to $92 \times 10^{10}$ erythrocytes that contain less than 300 IU of bacterial thymidine phosphorylase per $1 \times 10^{10}$ erythrocytes, and are free of animal proteins other than proteins derived from a patient from whom the autologous erythrocytes originate, wherein the erythrocytes comprise less than 200 EU endotoxin per mg of thymidine phosphorylase, and wherein the erythrocytes are free of BSA.

13. The composition according to claim 12, wherein the bacterial thymidine phosphorylase is an *E. coli* thymidine phosphorylase and/or, wherein the thymidine phosphorylase comprises the sequence shown in SEQ ID NO: 1 or a variant thereof, wherein the variant is at least 50%, at least 55%, at least 60%, at least 65%, at least 70%, at least 75%, at least 80%, at least 85%, at least 90% or at least 95%, at least 97% or at least 99% identical to the amino acid sequence of SEQ ID NO: 1.

14. The composition according to claim 12, wherein the amount of bacterial thymidine phosphorylase in the erythrocytes is from 30 to 300 IU/kg, 50 to 200 IU/kg or 75 to 150 IU/kg.

15. The composition according to claim 12, wherein the number of erythrocytes in the composition is from $75 \times 10^{10}$ to $92 \times 10^{10}$.

16. The composition according to claim 12 wherein the erythrocytes contain about 25 to 100 IU of bacterial thymidine phosphorylase per $1 \times 10^{10}$ erythrocytes.

\* \* \* \* \*